(12) United States Patent
Kim

(10) Patent No.: US 11,773,387 B2
(45) Date of Patent: Oct. 3, 2023

(54) DEVICE AND METHOD FOR INDUCING PLURIPOTENT CELLS USING ENERGY

(71) Applicant: STEMON Inc., Seoul (KR)

(72) Inventor: Soonhag Kim, Gyeonggi-do (KR)

(73) Assignee: STEMON Inc., Seoul (KR)

(*) Notice: Subject to any disclaimer, the term of this patent is extended or adjusted under 35 U.S.C. 154(b) by 315 days.

(21) Appl. No.: 15/532,032

(22) PCT Filed: Dec. 4, 2015

(86) PCT No.: PCT/KR2015/013269
§ 371 (c)(1),
(2) Date: Jul. 14, 2017

(87) PCT Pub. No.: WO2016/089178
PCT Pub. Date: Jun. 9, 2016

(65) Prior Publication Data
US 2017/0327814 A1     Nov. 16, 2017

(30) Foreign Application Priority Data

Dec. 4, 2014 (KR) .................. 10-2014-0173007
Dec. 4, 2015 (KR) .................. 10-2015-0172501

(51) Int. Cl.
| | | |
|---|---|---|
| *C12N 5/074* | (2010.01) | |
| *C12M 1/34* | (2006.01) | |
| *C12N 13/00* | (2006.01) | |
| *C12M 1/00* | (2006.01) | |
| *C12M 1/42* | (2006.01) | |
| *C12M 3/00* | (2006.01) | |

(52) U.S. Cl.
CPC .............. *C12N 13/00* (2013.01); *C12M 1/42* (2013.01); *C12M 3/00* (2013.01); *C12M 31/00* (2013.01); *C12M 41/14* (2013.01); *C12M 41/46* (2013.01); *C12N 5/0696* (2013.01); *C12N 2500/32* (2013.01); *C12N 2500/44* (2013.01); *C12N 2501/115* (2013.01); *C12N 2506/1307* (2013.01); *C12N 2521/10* (2013.01); *C12N 2523/00* (2013.01); *C12N 2529/10* (2013.01)

(58) Field of Classification Search
CPC .. C12N 13/00; C12N 5/0696; C12N 2500/44; C12N 2500/32; C12N 2501/115; C12N 2506/1307; C12N 2521/10; C12N 2523/00; C12N 2529/10; C12M 1/42; C12M 3/00; C12M 31/00; C12M 41/14
See application file for complete search history.

(56) References Cited

U.S. PATENT DOCUMENTS 7,052,720 B1   5/2006   Jones
2007/0065420 A1   3/2007   Johnson

FOREIGN PATENT DOCUMENTS

WO   WO-2013134931 A1 *   9/2013   ........... C12N 5/0062
WO   2013-163296 A1   10/2013

OTHER PUBLICATIONS

Hunter, G et al. A radial mode ultrasonic horn for the inactivation of *Escherichia coli* K12. Ultrasonics Sonochemistry. 2008. 15: 101-109. (Year: 2008).*
Tsen, SD et al. Prospects fora novel ultrashort pulsed laser technology for pathogen inactivation. Journal of Biomedical Science. 2012. 19: 62. 11 pages. (Year: 2012).*
Guannan et al. The effect of forced growth of cells into 3D spheres using lowattachment surfaces on the acquisition of sternness properties, 2013, Biomaterials 34: 3215-3222 (Year: 2013).*
Hua and Thompson, Inactivation of *Escherichia coli* by Sonication at Discrete Ultrasonic Frequencies 2000 Wat. Res. vol. 34, No. 15, pp. 3888-3893 (Year: 2000).*
Christakou, A. E. et al., "Solid Tumor Spheroid Formation by Temperature-Controlled High Voltage Ultrasound in a Multi-Well Microdevice". In: 18th International Conference on Miniaturized Systems for Chemistry and Life Sciences. San Antonio, Texas, USA: MicroTAS 2014, Oct. 26-30, 2014, pp. 573-575.
Liu, Jian et al. "Functional Three-Dimensional HepG2 Aggregate Cultures Generated From an Ultrasound Trap: Comparison With HepG2 Spheroids", Journal of cellular biochemistry, 2007, vol. 102, No. 5. pages 1180-1189.
Lv, Yonggang et al., "Effects of Low-Intensity pulsed Ultrasound on Cell Via-Bility, Proliferation and Neural Differentiation of induced Pluripotent Stem Celis-derived Neural Crest Stem Cells", Biotechnology letters, Sep. 28, 2013, vol. 35, No. 12, pp. 2201-2212.
Abrahamse, Heide, "The Use of Laser Irradiation to Stimulate Adipose derived Stem Cell Proliferation and Differentiation for Use in Autologous Grafts", In: The 7th International Conference on Laser Applications, edited by M. Ablel Harith, South Africa: ICLA, 2009, vol. 1172, pp. 95-100.
International Search Report for International application No. PCT/KR2015/013269, dated Mar. 31, 2016, 7 pages.

* cited by examiner

*Primary Examiner* — Taeyoon Kim
*Assistant Examiner* — Alexandra F Connors
(74) *Attorney, Agent, or Firm* — Cozen O'Connor

(57) ABSTRACT

The present invention relates to a device and a method for inducing pluripotent cells using energy and, more specifically, has an effect of inducing new type pluripotent cells having pluripotent characteristics by applying energy such as ultrasonic waves, lasers or heat treatment to differentiated cells.

3 Claims, 59 Drawing Sheets
Specification includes a Sequence Listing.

(a)

(b)

Con: control HDF; W: water; S: 5 days human Physics cell

[Endoderm/Ectoderm/Neuron]
UD: undifferentiated SOUND cells
D: differentiated SOUND cells

[Mesoderm/Cardiomyocyte]
UD: undifferentiated SOUND cells
D: differentiated SOUND cells

DEVICE AND METHOD FOR INDUCING PLURIPOTENT CELLS USING ENERGY

SEQUENCE STATEMENT

Incorporated by reference herein in its entirety is the Sequence Listing entitled "Sequence Listing ST25," created Jul. 4, 2017, size of 23 kilobytes.

CROSS-REFERENCE TO RELATED APPLICATION

This application claims priority to and is a 35 U.S.C. § national phase application of PCT/KR2015/013269, filed Apr. 12, 2015, now published as International Publication No. WO/2016/089178, the disclosure of which is incorporated herein by reference in its entirety.

BACKGROUND

1. Field of the Invention

The present invention relates to a device and a method for inducing pluripotent cells using energy capable of inducing pluripotent cells having pluripotent characteristics by applying energy such as ultrasound, lasers, heat treatment, etc.

2. Discussion of Related Art

Pluripotency is an ability of cells to differentiate into three germ layer lineages, that is, ectoderm, mesoderm and endoderm. Pluripotent stem cells are clinically important for disease models or transplantation because the stem cells are differentiated into any types of cells or tissues in the body. Therefore, the current major requests in reprogramming or differentiation of embryonic stem cells, induced pluripotent stem cells (iPSC), somatic cells, and patient-derived cells should be simple, fast, efficient, and safe for clinical application with free of the introduction of exogenous genetic materials or chemical or small molecules. Recent studies have demonstrated that the interactions between the environment and genotypes are closely related to the gene expression and phenotypic variation in living organisms. Controlling the environmental stimulation such as structural, mechanical, magnetic, ultrasonic cues can modulate cell fate, proliferation, and cellular uptake efficiency. Although the exact molecular mechanism for these approaches is still unclear, these methods are acceptable as an alternative way to achieve the safety without introduction of genetic materials, chemical compounds and small molecules.

In this regard, the present inventors have developed a new method for inducing novel pluripotent cells having pluripotent characteristics that express undifferentiated markers and three germ layer marker genes that may differentiate into three germ layer, that is, ectoderm, mesoderm and endoderm, called Physics (pluripotent sphere yielded by ultrasonic stimulus) cells, by applying energy with cellular environmental cues under gene- and chemical-free condition.

SUMMARY OF THE INVENTION

Therefore, it is an aspect of the present disclosure to provide a method of inducing a novel type of pluripotent cells having pluripotent characteristics from differentiated cells by applying energy without any introduction of a reprogramming inducing factor into differentiated cells and a chemical, and a device for inducing the pluripotent cells.

To solve the above problems, according to an aspect of the present invention, there is provided a method of reprogramming differentiated cells into pluripotent cells, which includes mixing differentiated cells with a culture medium and forming spheroids by applying energy to the resulting mixture and culturing the mixture for a predetermined time, wherein, the spheroids have pluripotent characteristics.

According to another aspect of the present invention, there is provided a device for inducing pluripotent cells, which includes a culture chamber configured to accommodate differentiated cells and a culture medium; and a device for applying energy to the differentiated cells and the culture medium equipped at one side of the culture chamber, wherein, the differentiated cells and the culture medium are mixed, and spheroids are formed by applying energy to the resulting mixture and culturing the mixture for a predetermined time, and the spheroids have pluripotent characteristics.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Figure 1:
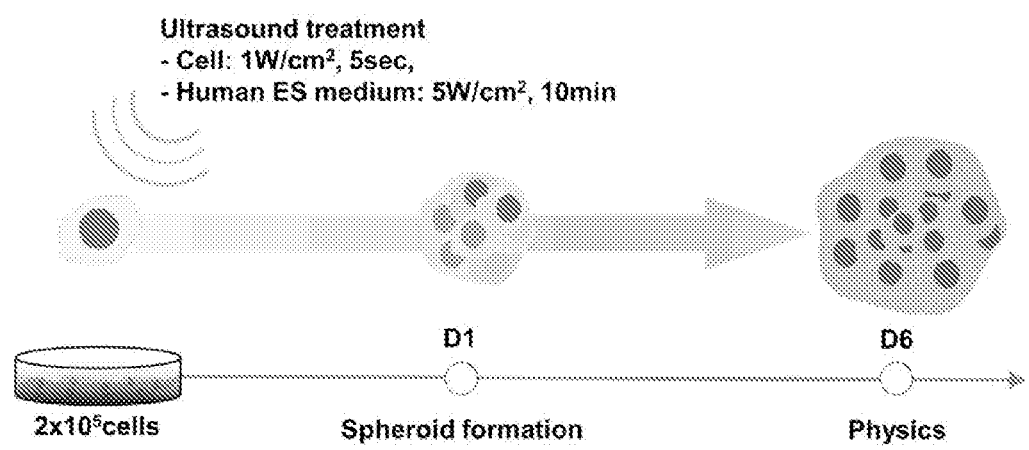
FIG. 1 is a schematic diagram of human Physics cells having pluripotent characteristics according to the present invention.

Hereinafter, configurations of the present invention will be described in detail.

The present invention relates to a method of reprogramming differentiated cells into pluripotent cells, which includes mixing differentiated cells with a culture medium, and forming spheroids by applying energy to the resulting mixture and culturing the mixture for a predetermined time, wherein, the spheroids have pluripotent characteristics.

The present invention is characterized in that a novel type of pluripotent cells, which has pluripotent characteristics and shows a stronger differentiation property than known induced pluripotent stem cells, may be induced from differentiated cells by applying suitable energy without introduction of a reprogramming inducing material such as a reprogramming inducing factor, a chemical compound, etc. into differentiated cells.

The pluripotent cells have a characteristic distinguished from the known induced pluripotent stem cells in that the differentiation of the pluripotent cells is easily induced in response to an external environment, and the pluripotent cells show a property of progenitor cells having a strong differentiation property, compared to that of the stem cells. That is, when embryonic stem cells such as induced pluripotent stem cells are used for cell therapy, the embryonic stem cells somewhat require a preparative step of undergoing a differentiation process, which involves a risk factor for generating cancer, and safety issues are encountered when a viral vector is used to introduce the reprogramming inducing factor. However, the pluripotent cells of the present invention do not have to be cultured by co-culturing different types of cells because the pluripotent cells are induced without separately introducing the reprogramming inducing material such as a reprogramming inducing factor or a chemical compound to mutate a gene, and thus there are no problems regarding cell contamination (a problem arising from mixing pluripotent cells with another type of cells). Also, the pluripotent cells of the present invention have no problem regarding the occurrence of cancer because the pluripotent cells do not form a teratoma similar to cancer cells in an in vivo experiment, and thus safety is secured. That is, the pluripotent cells of the present invention have an advantage in that a time spanning from autologous cell treatment to transplantation may be remarkably shortened due to a simple and short induction process.

According to the present invention, the spheroids may be specifically formed with high yield by applying energy to both of the culture medium and the differentiated cells.

The energy may include one selected from ultrasound, lasers, and heat treatment.

The pluripotent cells of the present invention are characterized by stably expressing any one undifferentiated markers or three germ layers marker genes consisting of the ectoderm, the mesoderm and the endoderm among OCT3/4, SOX2, NANOG, c-MYC, KLF4, TDGF1, SSEA4, TRA-1-60, PAX6, Nestin, Brachyury, SMA, GATA4, and AFP.

As described above, since the pluripotent cells are formed without introducing the reprogramming inducing factor into differentiated cells, the present inventors have contemplated the correlation of the pluripotent cells with an exosome. That is, the ultrasound, the lasers or the heat treatment induces a rise in temperature due to energy application, generation of reactive oxygen species (ROS), vibration of microbubbles generated by ultrasound, and occurrence of liquid flow, that is, induces generation of microstreams along a cell membrane to cause fine damage to the cell membrane due to such an effect, thereby inducing formation of holes to increase the absorption of foreign substances. This is proven by analyzing a change in intracellular $Ca^{2+}$ concentration and confirming whether $H_2O_2$ is generated in the cells. That is, the analysis of the change in intracellular $Ca^{2+}$ concentration reflects that the $Ca^{2+}$ concentration in the cells (cytosols) instantly increases when the cell membrane is damaged or the fluidity of the membrane increases, thereby verifying an increase in fluidity of the cell membrane. According to one exemplary embodiment of the present invention, it can be seen that the $Ca^{2+}$ concentration rapidly increases immediately after the ultrasound treatment, and then gradually decreases to a level of the control in which the cells are not treated with ultrasound, indicating that the cell membrane is recovered after the damage to the cell membrane is induced. In the experiment confirming whether $H_2O_2$ is generated in the cells, it can also be seen that the cell membrane is recovered after the damage to the cell membrane is induced as an amount of the generated $H_2O_2$ increases immediately after the initial ultrasound treatment and then gradually decreases to a level of the control in a pattern similar to that of the $Ca^{2+}$ concentration. Also, since ATP is used as a signal responding to various types of cellular stress, the ATP concentration in the pluripotent cells is analyzed after the ultrasound treatment. As a result, the ATP is released at a higher level, compared to the untreated control. Further, the expression of an ionotropic P2X receptor and a metabotropic P2Y receptor by the ATP release is also activated in the pluripotent cells, compare to the control.

Meanwhile, exosomes are known to contain genetic elements (DNA, mRNA, microRNA, proteins, etc.) in an inside thereof. In this case, as the exosomes flowing out of a cell membrane, due to the damage to the cell membrane, enter other surrounding cells, the genetic elements present inside the exosomes may be transferred. Therefore, as the expression of undifferentiated markers which have been poorly expressed in the cells or whose expression has been maintained in a suppressed state is induced and promoted in response to the stimuli caused by the ultrasound treatment, and cell membranes are damaged at the same time, the exosomes present inside the cells including the undifferentiated markers whose expression is induced and promoted are released from the cells to enter the surrounding cells. In this case, it is assumed that, since cell membranes of the surrounding cells are also partially damaged, the exosomes enter the cells with high efficiency due to the increased fluidity of the cell membranes, compared to when the cell membranes are in a normal state. It is contemplated that genetic elements on the undifferentiated markers whose expression is induced and promoted, which are present inside such exosomes, is transported to make pluripotent cells. According to one exemplary embodiment of the present invention, a culture medium is recovered during the induction of the pluripotent cells, and the exosomes in the medium are extracted to determine whether a pluripotent cell-related undifferentiated marker is present inside the exosomes. As a result, it was revealed that known undifferentiated markers are expressed at a high level. Therefore, the present inventors have contemplated these facts to support this hypothesis. Also, it was revealed that the karyotype is normal without any mutation even when treated with such ultrasound, lasers or heat treatment.

Such a hypothesis suggests that the pluripotent cells may be prepared by inducing the release of the exosomes when the cell membranes are damaged.

In this specification, the term "pluripotent cell" refers to a cell that retains pluripotency after energy, that is, ultrasound, lasers or heat treatment in a strict sense, is applied to the cells. In this specification, the pluripotency refers to a state in which an undifferentiated marker expressed in embryonic stem cells is stably expressed. Further, the pluripotency refers to a state in which three germ layer markers for the endoderm, the ectoderm and the mesoderm are expressed. The term "pluripotent cells" may be used interchangeably with "Physics (pluripotent sphere yielded by ultrasonic stimulus) cells" or "Physics spheroids." A method of reprogramming the differentiated cells into pluripotent cells of the present invention will be described in detail with reference to FIG. 1.

First of all, a cell culture medium and differentiated cells are mixed, and energy is applied to the resulting mixture.

Prior to applying the energy to the mixture, the energy may be applied to the cell culture medium to enhance efficiency of reprogramming into the pluripotent cell.

The energy may include any one among ultrasound, lasers or heat treatment.

The ultrasound treatment of the culture medium may be performed by treating the culture medium with ultrasound having an output intensity of 1 $W/cm^2$ to 20 $W/cm^2$ for 1 to 20 minutes, specifically, with ultrasound having an output intensity of 2 $W/cm^2$ to 10 $W/cm^2$ for 5 to 15 minutes, more specifically, with ultrasound having an output intensity of 3 $W/cm^2$ to 7 $W/cm^2$ for 7 to 13 minutes.

The treatment of the culture medium with the lasers may be performed by treating the culture medium with pulsed laser beams having a wavelength band of 300 to 900 nm for 1 second to 20 seconds, more specifically, with the pulsed laser beams having this wavelength band for 3 seconds to 10 seconds, even more specifically, with the pulsed laser beams having this wavelength band for 4 seconds to 6 seconds. A wavelength of 400 nm, 808 nm, or 880 nm may, for example, be used as the wavelength band.

The heat treatment of the culture medium may be performed for 5 minutes to 20 minutes under the condition of a temperature of 40 to 50° C.

An embryonic stem cell culture medium, a stem cell differentiation-inducing medium, and the like may be used as the culture medium.

Mammal-derived fibroblast cells; cancer cells including cervical cancer cells (HeLa cells); or organ tissue cells including pulmonary epithelial cells (L132 cells) may be used as the differentiated cells.

When energy is applied to the differentiated cells, the differentiated cells are desirably exposed to a certain intensity of the energy. Cell viability may be reduced when the intensity falls out of this intensity range.

Therefore, the ultrasound treatment of the mixture of the culture medium and the differentiated cells may be performed at an output intensity of 0.5 $W/cm^2$ to 3 $W/cm^2$ for 1 to 5 seconds, more specifically, at an output intensity of 0.7 $W/cm^2$ to 2 $W/cm^2$ for 1 to 5 seconds, even more specifically, at an output intensity of 0.8 $W/cm^2$ to 1.5 $W/cm^2$ for 1 to 5 seconds.

The treatment of the mixture of the culture medium and the differentiated cells with the lasers may be performed by irradiating the mixture with pulsed laser beams having a wavelength band of 300 to 900 nm for 1 second to 20 seconds, more specifically, with the pulsed laser beams having this wavelength band for 3 seconds to 10 seconds, even more specifically, with the pulsed laser beams having this wavelength band for 4 seconds to 6 seconds. A wavelength of 400 nm, 808 nm, or 880 nm may, for example, be used as the wavelength band.

The heat treatment of the mixture of the culture medium and the differentiated cells may be performed by exposing the mixture to heat for 1 minute to 10 minutes under the condition of a temperature of 40 to 50° C., and then exposing the mixture to heat for 5 to 10 seconds under the condition of a temperature of 0° C. to 4° C.

Next, the mixture to which the energy is applied is cultured for a predetermined time to form spheroids having pluripotency.

The culture of the mixture to which the energy is applied may be performed for a period of time in which the spheroids stably expressing an undifferentiated marker are formed by a suspension culture method or a monolayer culture method, that is, for 3 days to 10 days. However, the culture time may be suitably adjusted at a level of ordinary skill in the art because the formation of the spheroids having pluripotency varies depending on the culture method, the types of cells or culture media.

According to one exemplary embodiment of the present invention, the suspension culture is more efficient in forming the spheroids, compared to the monolayer culture. Also, the number and size of the spheroids in the suspension culture are larger than those in the monolayer culture, and the suspension culture exhibits a uniform size distribution.

According to one exemplary embodiment of the present invention, when human dermal fibroblast cells treated with the ultrasound or lasers are suspension-cultured, the expression of the undifferentiated markers is increased or stabilized from approximately day 3, indicating that the reprogramming starts from this point of time. Also, the expression of the undifferentiated markers is increased or stabilized from approximately day 8 upon the suspension culture of heat-treated human dermal fibroblast cells, indicating that the reprogramming starts from this point of time.

From the fact that the undifferentiated markers, for example, OCT3/4, SOX2, NANOG, c-MYC, KLF4, TDGF1, SSEA4, TRA-1-60, and the like are expressed, it can be seen that the spheroids have pluripotency. The presence of the undifferentiated markers may be analyzed using RT-PCR or an immunocytochemistry, but the present invention is not limited thereto.

Also, the pluripotent cells of the present invention have a characteristic of expressing three germ layer markers, that is, ectoderm (PAX6 and Nestin), mesoderm (Brachyury and SMA), endoderm (GATA4 and AFP) markers at a high level.

In addition, the pluripotent cells of the present invention have a characteristic of having a proliferative capacity since the pluripotent cells express Ki-67 which is a proliferation marker protein.

Further, it can be seen that, when the aforementioned reprogrammed pluripotent cells are co-cultured with feeder cells, the proliferation of the pluripotent cells increases, and differentiate into the ectoderm/endoderm/mesoderm and nerve cells/myocardial cells after the pluripotent cells are cultured in a differentiation-inducing medium.

Also, the present invention provides a device for inducing pluripotent cells, which includes:
a culture chamber configured to accommodate cells and a culture medium; and
a device for applying energy to the differentiated cells and the culture medium equipped at one side of the culture chamber, wherein, the differentiated cells and the culture medium are mixed, and spheroids are formed by applying energy to the resulting mixture and culturing the mixture for a predetermined time, and the spheroids have pluripotent characteristics.

The culture chamber refers to an incubator generally used to culture cells. For example, the culture chamber is provided with a temperature control unit and a carbon dioxide control unit. In this case, the cell culture conditions in the culture chamber may be properly adjusted at a level of ordinary skill in the art, depending on a purpose and the type of cells.

Also, because the suspension or monolayer culture methods may be used to reprogram the differentiated cells into the pluripotent cells, the culture chamber may have a structure in which such a culture is possible. For example, the culture chamber may be a culture chamber provided with an agitator for suspension culture.

The device for applying energy may include an ultrasound generation device configured to radiate ultrasound, a laser generation device configured to radiate lasers, or a temperature control device.

Known ultrasound generation devices that generate ultrasound having a frequency of 10 kHz to 100 MHz may be used as the ultrasound generation device without limitation.

Laser devices that generate pulsed laser beams having a wavelength band of 300 to 900 nm and an output of 1 to 15 W, a pulse duration time of 1 ms to 900 ms and a frequency of 1 to 100 Hz may be used as the laser generation device, but the present invention is not limited thereto.

Known temperature control devices capable of regulating a temperature in a range of −40° C. to 99.9° C. may be used as the temperature control device, but the present invention is not limited thereto.

The device for inducing pluripotent cells according to the present invention may be used to reprogram the differentiated cells into the pluripotent cells by treating the mixture of the culture medium and the differentiated cells with ultrasound, lasers or heat treatment using the ultrasound generation device, the laser generation device or the temperature control device and culturing the mixture for a predetermined time to form spheroids having pluripotency. In this case, the culture medium may be previously treated with the ultrasound, lasers or heat treatment prior to mixing the culture medium with the differentiated cells so as to enhance reprogramming efficiency.

Hereinafter, the present invention will be described in detail with reference to examples thereof. However, it should be understood that the following examples are just preferred examples for the purpose of illustration only and are not intended to limit or define the scope of the invention.

<Example 1> Generation of Physics Cells

FIG. 1 is a schematic diagram for forming Physics (pluripotent sphere yielded by ultrasonic stimulus) cells according to the present invention. Human dermal fibroblast cells (HDFa, Cat. No. C-013-5C, GIBCO (Invitrogen cell culture)) ($1 \times 10^6$) were mixed with an embryonic stem (ES) medium, which had been treated with ultrasound at an intensity of 5 W/cm² for 10 minutes, and the resulting mixture including the cells was treated with ultrasound at an intensity of 1 W/cm² for 5 seconds. The viable cells were selected, and $2 \times 10^5$ HDFs were then suspension-cultured for 6 days in a human ES cell culture medium in a 35-mm Petri dish for bacterial culture.

The spheroids were formed from the first day of culture, and the undifferentiated markers were expressed from day 3 onward.

<Experimental Example 1> Establishment of Optimal Experiment Conditions for Forming Spheroids Because the human dermal fibroblast cells formed spheroids when treated with ultrasound, experiments were performed under different ultrasound treatment conditions using different cell culture methods to establish the optimal conditions used to improve spheroid-forming efficiency.

As the cell culture method, suspension culture, in which cells were cultured in a cell culture dish whose surface was not coated (i.e., a Petri dish for bacterial culture), and monolayer culture, in which cells were cultured in a cell culture dish whose surface was coated so that the cells were easily attached to the surface of the dish (i.e., a tissue culture dish), were used.

Also, after classification into an untreated group (Null) as a control, a group in which a medium was treated with ultrasound (an ultrasound-treated medium (UM) treated at an ultrasound intensity of 5 W/cm² for 10 minutes), a group in which cells were treated with ultrasound (ultrasound treated cells (UC) treated at an ultrasound intensity of 1 W/cm² for 5 seconds), and a group in which both the cells and the medium were treated with ultrasound (UM plus UC (UCUM)), morphological changes of the cells in different culture time were observed, and spheroid-forming efficiency was determined by counting the spheroids to analyze changes in the number and size of the spheroids in different culture time. The cells used for experiments were human dermal fibroblast cells.

First, HDFs (1×10⁶) were directly exposed to ultrasound at ultrasound intensities (0, 0.5, 1, 3, 5, and 10 W/cm² for 5 seconds) to establish the ultrasound intensity conditions. Then, the viable cells were selected, and 2×10⁵ HDFs were then cultured for 6 days in a human ES cell culture medium in a 35-mm Petri dish for bacterial culture.

TABLE 1

Compositions of ES media

| Reagent names | Volume | Final concentration | Note |
|---|---|---|---|
| DMEM/F-12 | 500 mL | 500 mL | |
| Serum Replacement (KnockOut ™ Serum Replacement) | 100 mL | 20% | |
| Non-essential amino acids (NEAAs) | 5 mL | 1% | |
| Penicillin & Streptomycin (P/S) | 5 mL | 1% | |
| β-Mercaptoethanol | 0.9 mL | 0.1 mM | |
| Glutamin (L-Glutamine, 200 mM solution) | 2.5 mL | 1 mM | |
| Basic human fibroblast growth factor 2 (FGF) (Recombinant Human FGF-Basic) | 2 mg | 4 ng/mL | Added after ultrasound treatment |

Figure 2A:
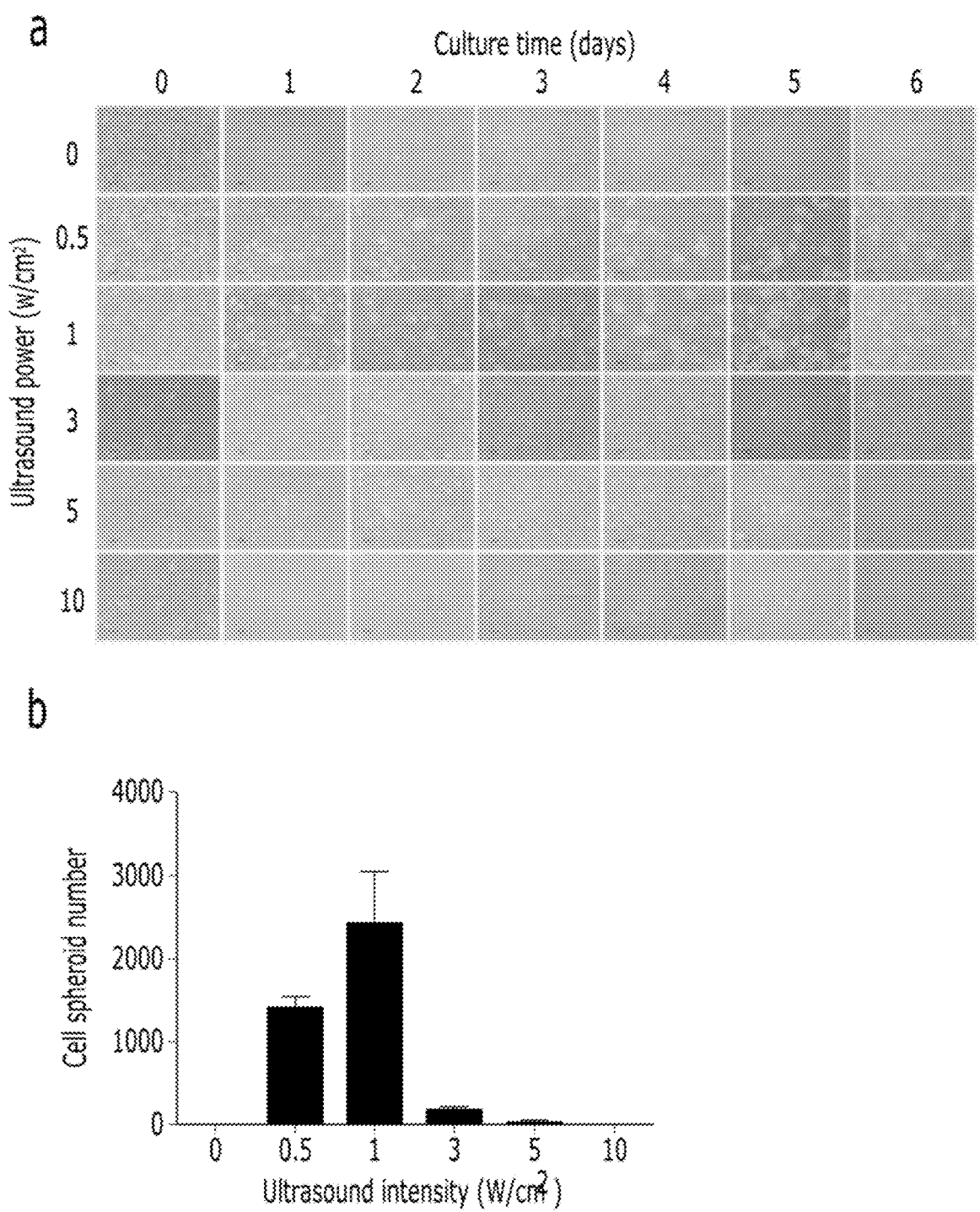
FIG. 2A is a diagram showing an effect of ultrasound intensity on human dermal fibroblasts (HDFs): a) shows the comparison of morphological changes of HDFs under different ultrasound intensity, and b) shows the number of multicellular spheroids formed under different ultrasound intensity.
Figure 2B:
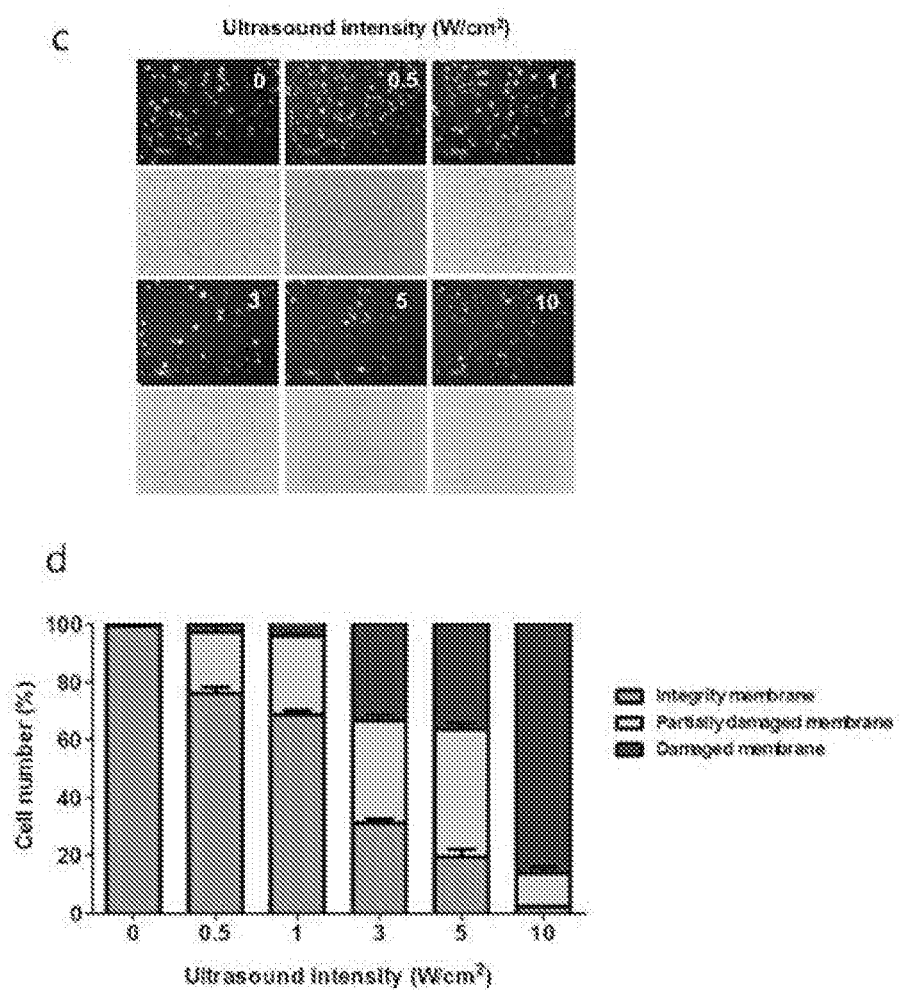
FIG. 2B is a diagram showing an effect of ultrasound intensity on the human dermal fibroblasts (HDFs): c) shows results of live/dead cell assay of ultrasound-treated HDFs, and d) shows percentages of viable and damaged cells in c).

As shown in (a) of FIG. 2A, most ultrasound-treated HDFs spontaneously aggregated at an ultrasound intensity of 0.5, 1 and 3 W/cm² to form multicellular spheroids. In the case of the control, the HDFs were attached to a surface of the dish, but the apoptosis of the HDFs treated with ultrasound having an intensity of 5 and 10 W/cm² increased without forming the spheroids.

(b) of FIG. 2A shows the number of the multicellular spheroids formed under different the ultrasound intensity as shown in (a) of FIG. 2A.

From the results of live/dead cell analysis and image analysis at an ultrasound intensity of 1 W/cm², it was revealed that 25% of the cells were partially damaged, and more than 95% or more of the cells were viable, as shown in FIGS. 2C and 2D. However, the HDFs were severely damaged at an ultrasound intensity of more than 1 W/cm², leading to apoptosis.

Therefore, the HDFs were cultured in a human ES cell culture medium at differing exposure times (0, 1, 2, 5, 10, 20, and 40 seconds) over 3 days under the condition of a fixed ultrasound intensity of 1 W/cm² in a 35-mm Petri dish for bacterial culture.

Figure 3A:
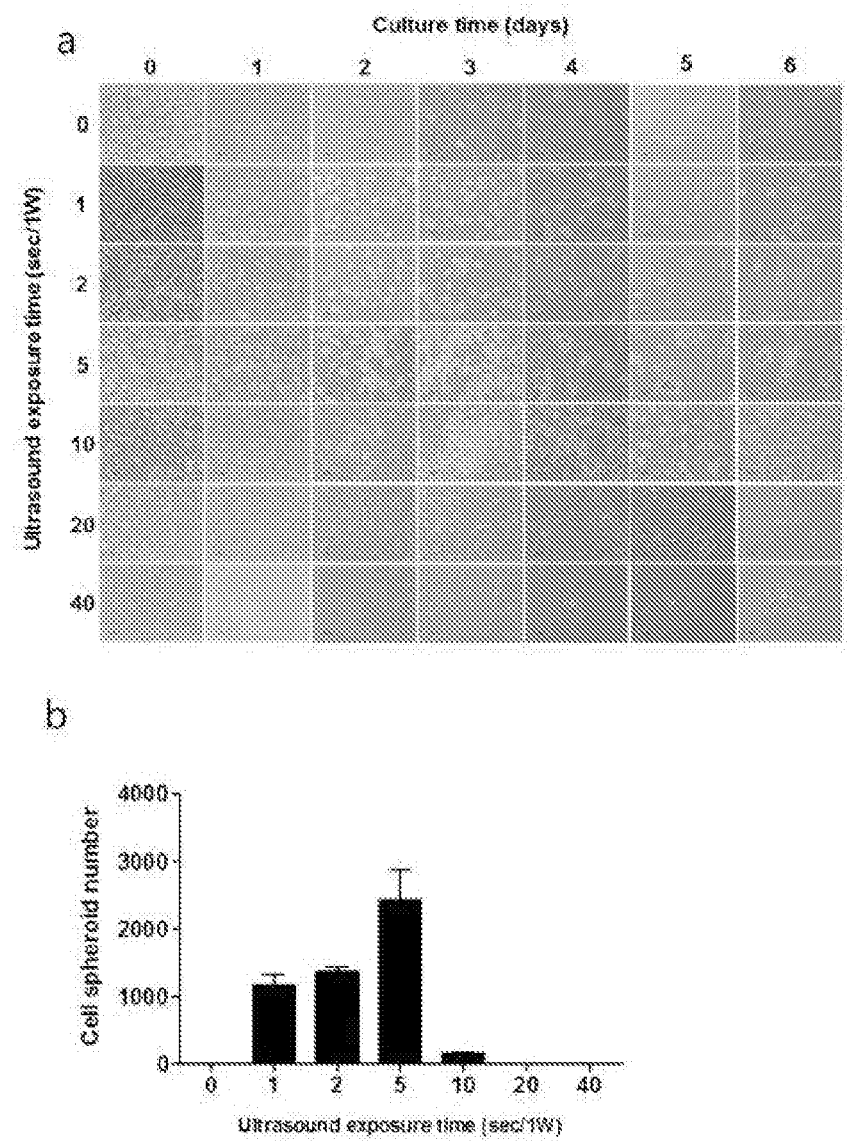
FIG. 3A is a diagram showing an effect of ultrasound exposure time under a fixed intensity of 1 W/cm$^2$: a) shows the comparison of morphological changes of HDFs under different ultrasound exposure time, and b) shows the number of multicellular spheroids formed under different ultrasound exposure time.
Figure 3B:
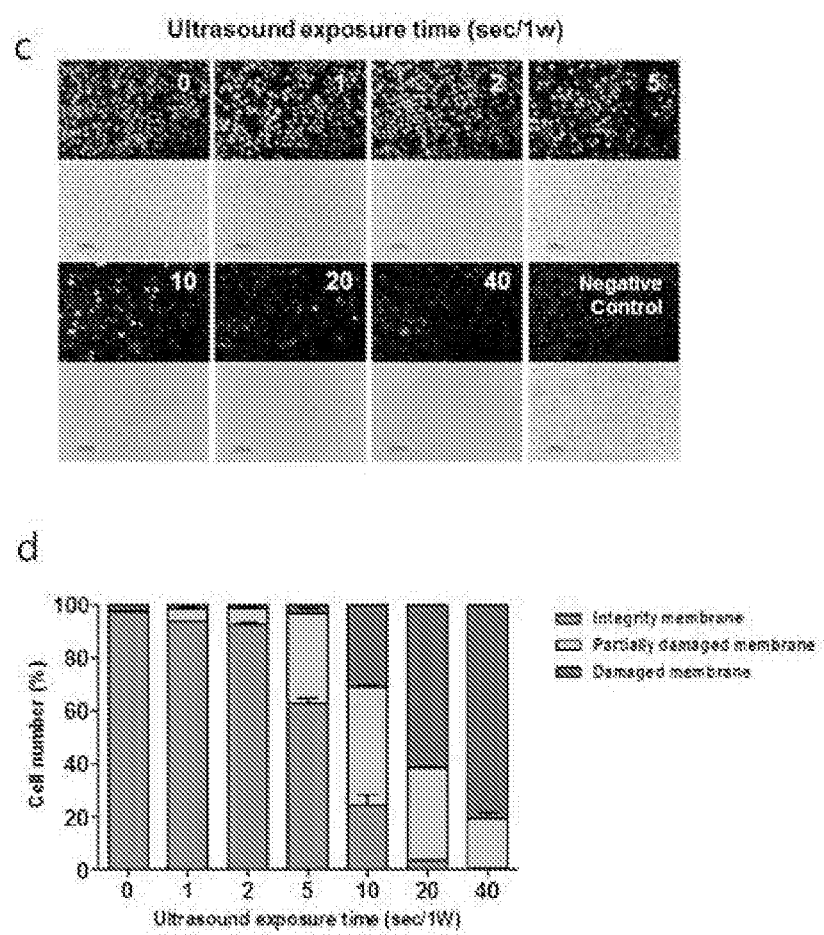
FIG. 3B is a diagram showing an effect of ultrasound exposure time under a fixed intensity of 1 W/cm$^2$: c) shows results of live/dead cell assay of ultrasound-treated HDFs, and d) shows percentages of viable and damaged cells in c).

As shown in (a) through (d) of FIGS. 3A and 3B, when the cells were exposed to ultrasound for 5 seconds, the number of formed spheroids was higher, compared to the other exposure times. However, when the cells were exposed for 10 seconds or more, apoptosis dramatically increased, it seems that the apoptosis was due to damage to the cell membranes.

Next, an ES cell culture medium was treated with ultrasound at varying exposure intensities (0, 1, 5, and 10 W/cm²) for 10 minutes. 2×10⁵ HDFs (1 W/cm² for 5 seconds) exposed to ultrasound were cultured in such media for 3 days in 35-mm Petri dishes for bacterial culture.

Figure 4:
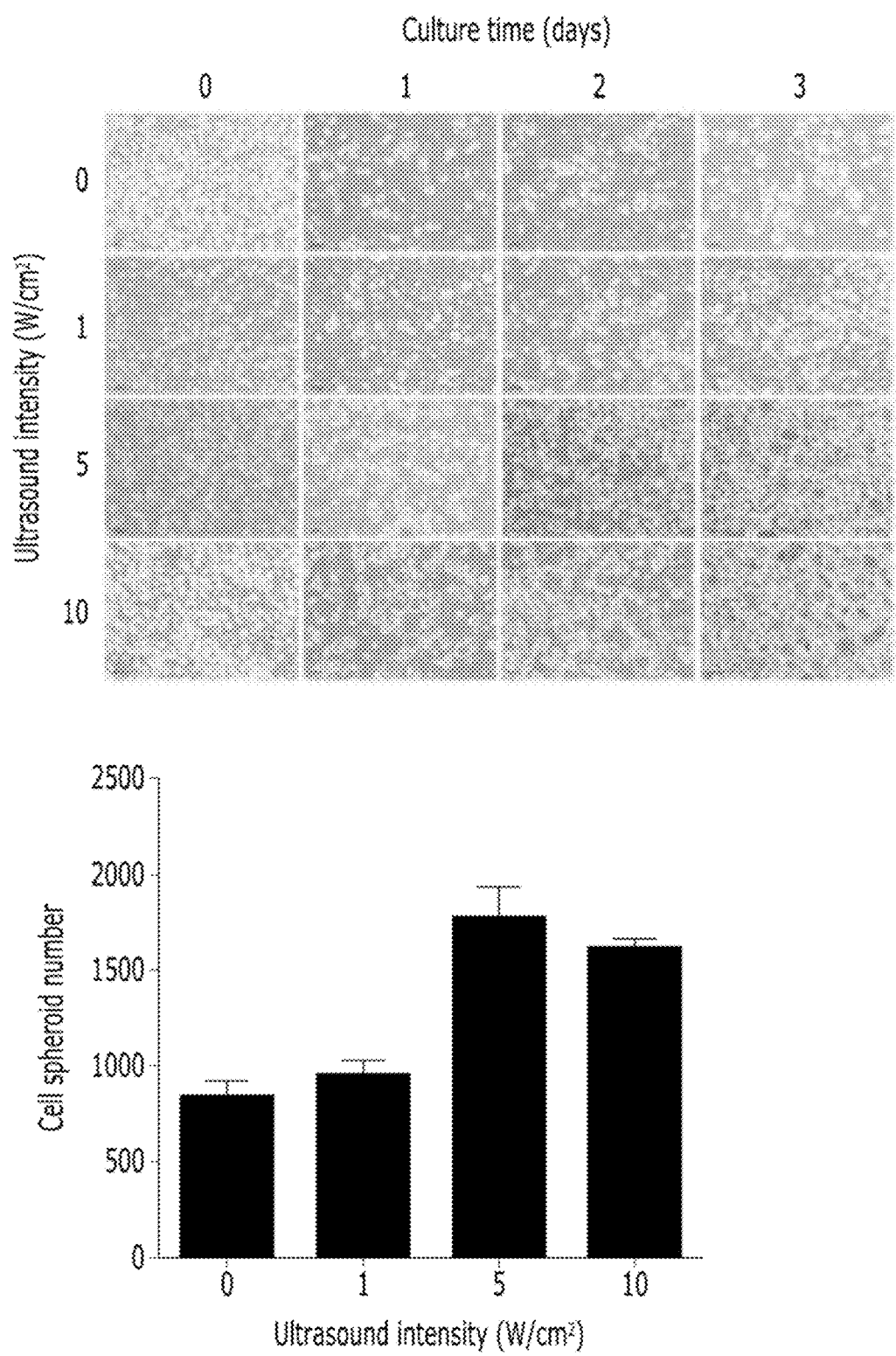
FIG. 4 is a diagram showing an effect of ultrasound intensity on human ESC culture media: the upper panel shows the comparison of morphological changes of ultrasound-treated HDFs growing in an ultrasound-treated medium, and the lower panel shows the number of multicellular spheroids formed in the medium.

As shown in FIG. 4, approximately twice as many spheroids were formed in the culture medium treated with ultrasound at the intensity of 5 W/cm², compared to treatment at the intensity of 1 W/cm².

Figure 5:
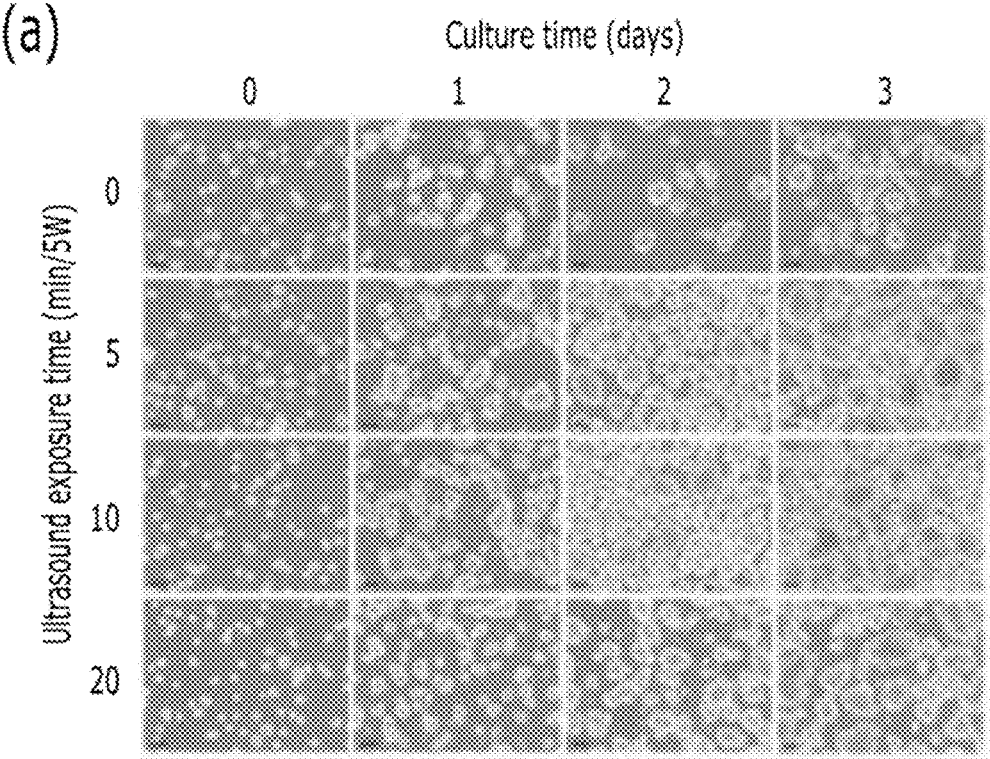
FIG. 5 is a diagram showing an effect of ultrasound exposure time under a fixed intensity of 5 W/cm$^2$: a) shows the comparison of morphological changes of ultrasound-treated HDFs growing in an ultrasound-treated medium, and b) shows the number of multicellular spheroids formed in a).
Figure 5:
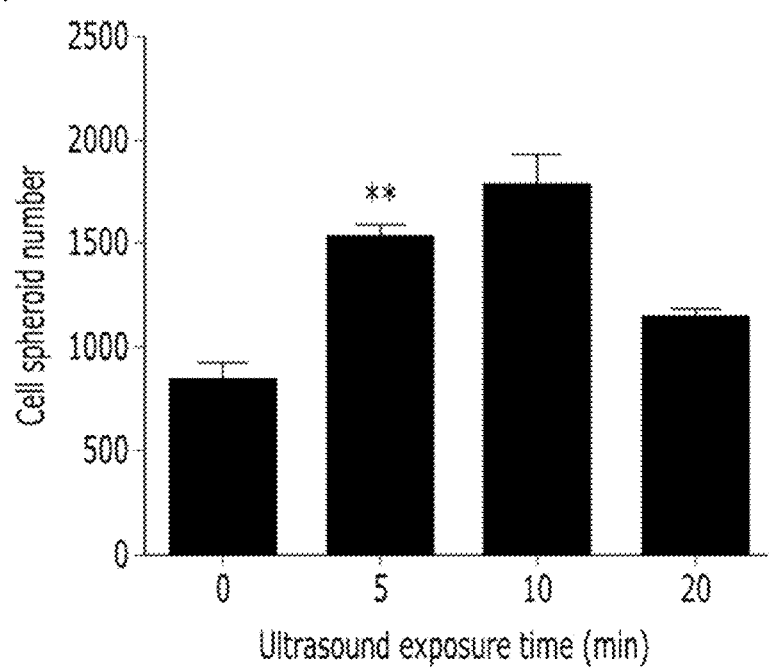

Changes in exposure time (0, 5, 10, and 20 minutes) did not have a significant influence on spheroid-forming efficiency. In general, a shorter exposure time led to a uniform size range and an increased number of the spheroids (FIG. 5).

Subsequently, to examine a spheroid-forming effect under different culture conditions, an ESC culture medium was treated with ultrasound (5 W/cm² for 10 minutes), and HDFs (1×10⁶) were treated with ultrasound (1 W/cm² for 5 seconds). The live HDFs (×10) were selected, and then suspension-cultured in a Petri dish for bacterial culture or monolayer-cultured in a tissue culture dish.

Figure 6:
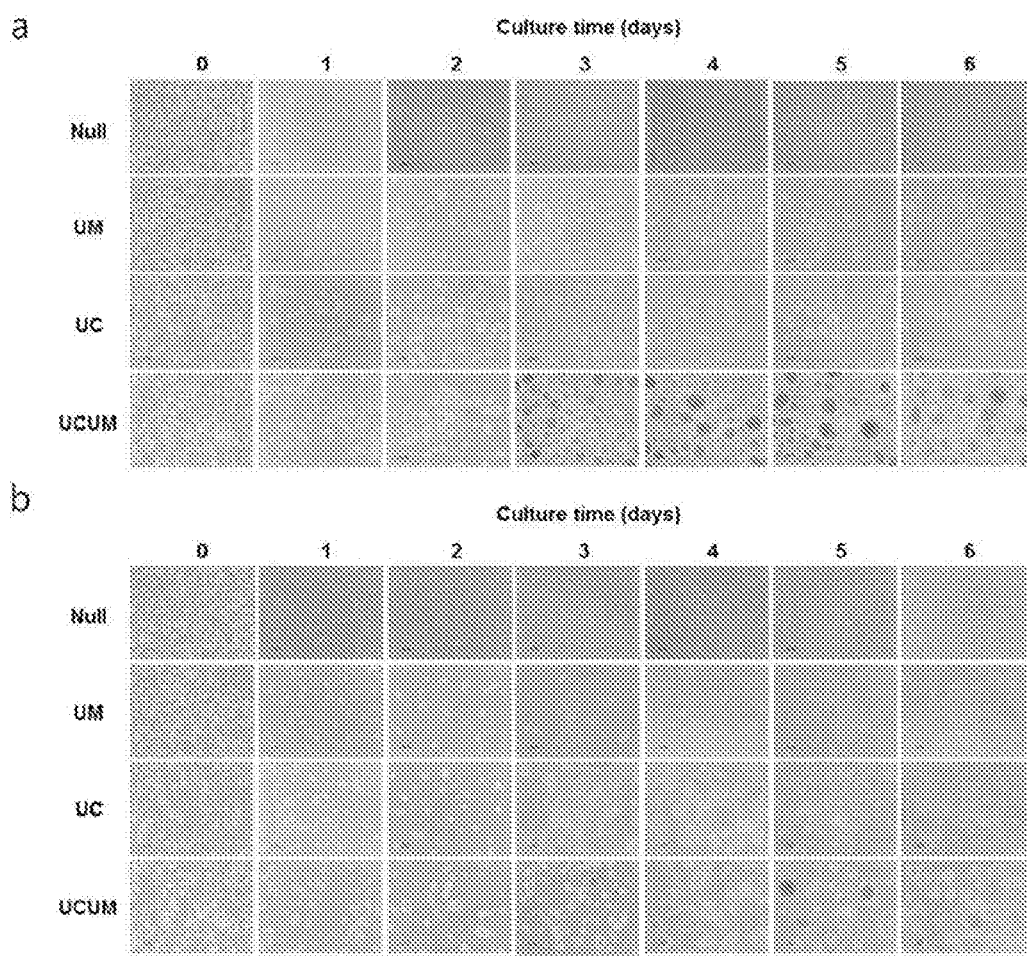
FIG. 6 is a diagram showing effects of an ultrasound treatment condition and a culture condition for forming multicellular spheroids: a) shows suspension culture results, and b) shows monolayer culture results.

As shown in FIG. 6, the suspension-cultured ultrasound-treated HDFs had a higher spheroid-forming efficiency, compared to the monolayer-cultured HDFs. Also, when the stimulus such as ultrasound was applied to both the cells and the culture medium, the HDFs showed a higher spheroid-forming efficiency.

To observe a size distribution of the multicellular spheroids formed under different the ultrasound stimuli under the suspension or monolayer culture conditions, the ultrasound-treated HDFs or untreated HDFs were cultured in an ES cell culture medium treated with ultrasound or an untreated ES cell culture medium in a Petri dish for bacterial culture or a tissue culture dish.

Figure 7A:
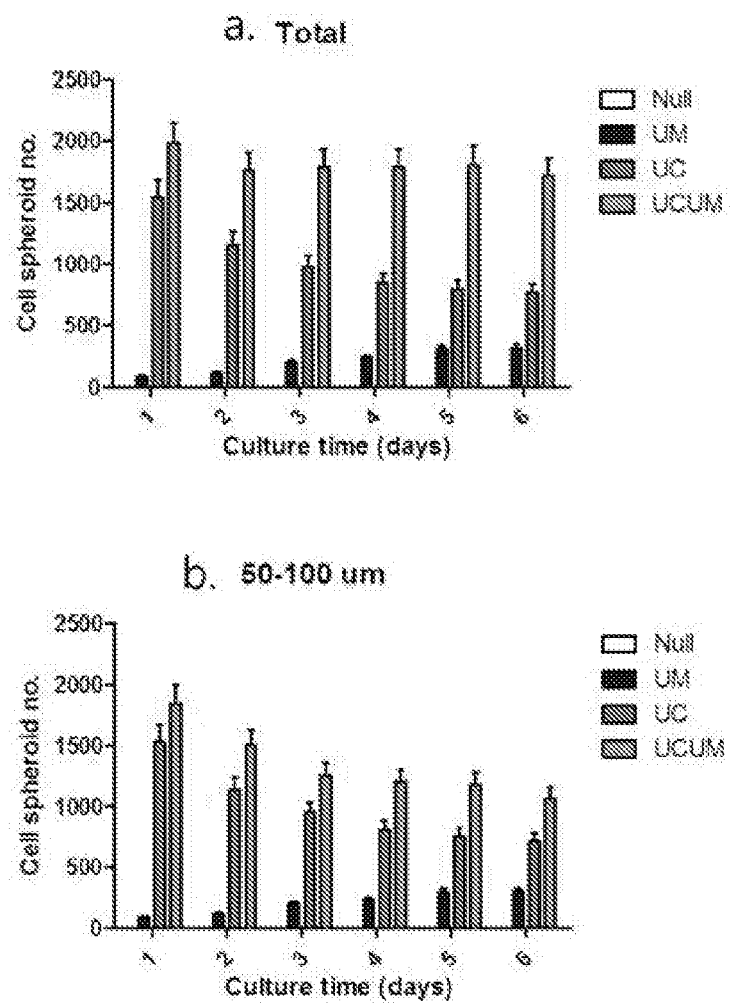
FIG. 7A shows size distributions of multicellular spheroids formed under a suspension culture condition under different ultrasound stimuli (UC, UM, and UCUM): a) shows the distribution of the spheroids by total size, and b) shows the distribution of the spheroid having a size of 50 to 100 μm.
Figure 7B:
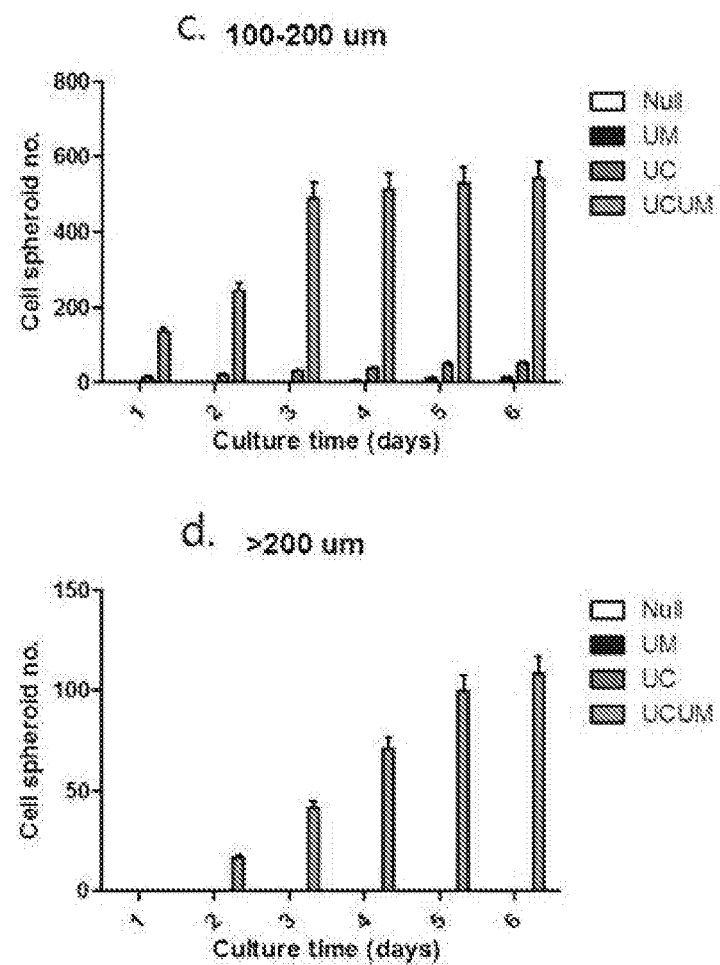
FIG. 7B shows size distributions of the multicellular spheroids formed under the suspension culture condition under different the ultrasound stimuli (UC, UM, and UCUM): c) shows the distribution of the spheroids having a size of 100 to 200 μm, and d) shows the distribution of the spheroids having a size of more than 200 μm.
Figure 8A:
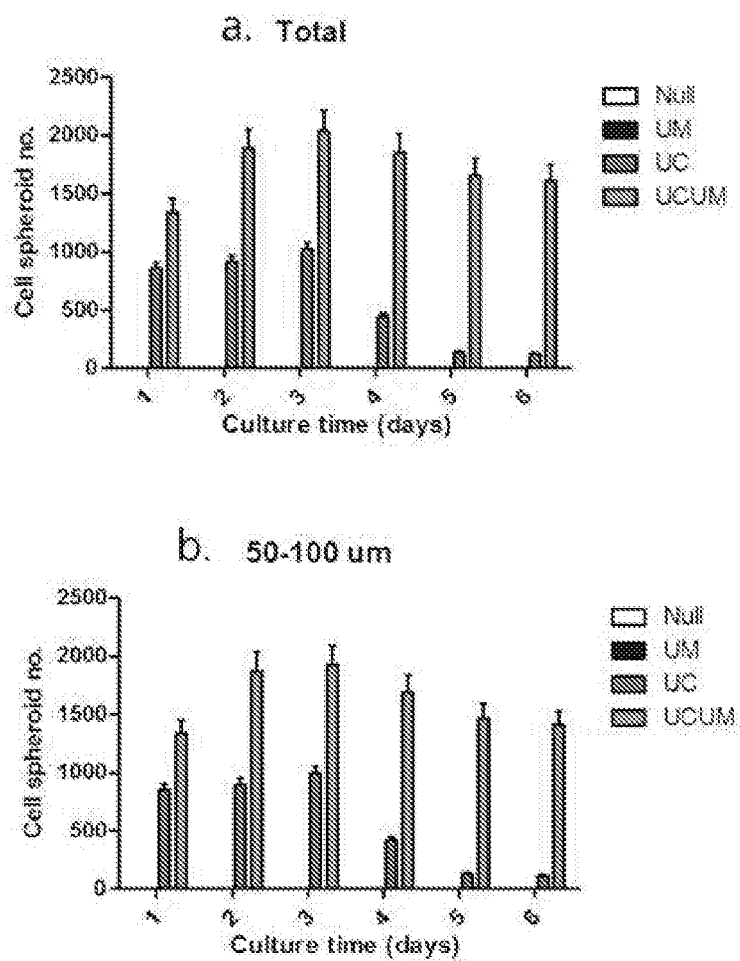
FIG. 8A shows size distributions of the multicellular spheroids formed under a monolayer culture condition under different the ultrasound stimuli (UC, UM, and UCUM): a) shows the distribution of the spheroids by total size, and b) shows the distribution of the spheroid having a size of 50 to 100 μm.
Figure 8B:
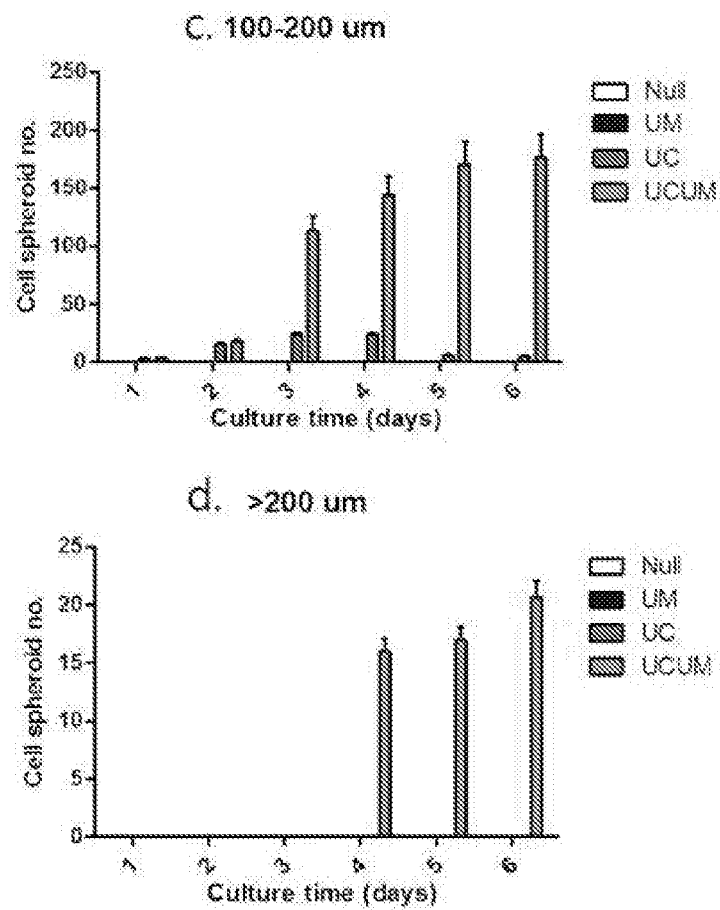
FIG. 8B shows size distributions of the multicellular spheroids formed under the monolayer culture condition under different the ultrasound stimuli (UC, UM, and UCUM): c) shows the distribution of the spheroids having a size of 100 to 200 μm, and d) shows the distribution of the spheroids having a size of more than 200 μm.

As shown in FIGS. 7 and 8, the higher spheroid-forming efficiency was observed in both of the culture dishes when both the HDFs and the culture medium were treated with ultrasound (UCUM).

Also, the suspension culture condition exhibited a higher efficiency, and the spheroids were larger in number and size (a diameter of 200 μm or more), and exhibited a uniform size distribution, compared to the monolayer culture condition.

The ultrasound-treated HDFs (UC) grown in the untreated ES cell culture medium formed spheroids. However, the number and size (up to 200 μm) of the spheroids were very small, compared to the UCUM condition. When the normal HDFs (UM) were cultured in the ultrasound-treated ES cell culture medium, a small amount of spheroids having a smaller size (100 μm or less) were formed. There was a very low spheroid-forming efficiency when culturing under the UC and UM conditions for monolayer culture in the tissue culture dish. Most of the HDFs were attached to a surface of the culture dish, and the number of the spheroids was very small.

Then, to examine expression of representative undifferentiated genes according to the culture time of the multicellular spheroids formed under different the ultrasound stimulus under the suspension or monolayer culture conditions, the cells of the control and the ultrasound-treated groups (Null, UM, UC, and UCUM) were recovered in different culture time (days 1, 2, 3, 4, 5 and 6) according to the method of Example 1, and mRNA was extracted using a Dynabeads mRNA direct kit (Ambion). Then, SuperScript-II (Invitrogen) cDNA was synthesized, PCR-amplified using primers as listed in Table 2, and then subjected to electrophoresis for the purpose of analysis.

Figure 9A:
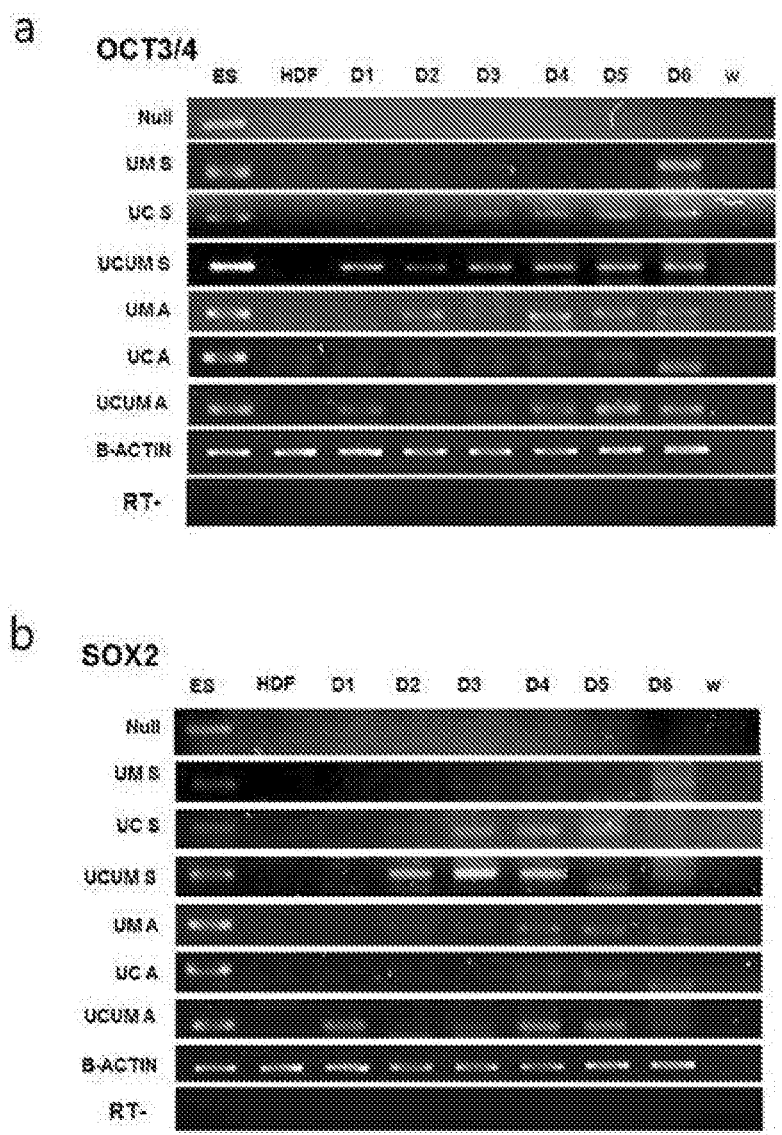
FIG. 9A shows RT-PCR analysis results of comparing expression levels of a pluripotent marker gene, OCT3/4 (a) and SOX2 (b) in human Physics cells between the suspension culture condition and the monolayer culture condition.
Figure 9B:
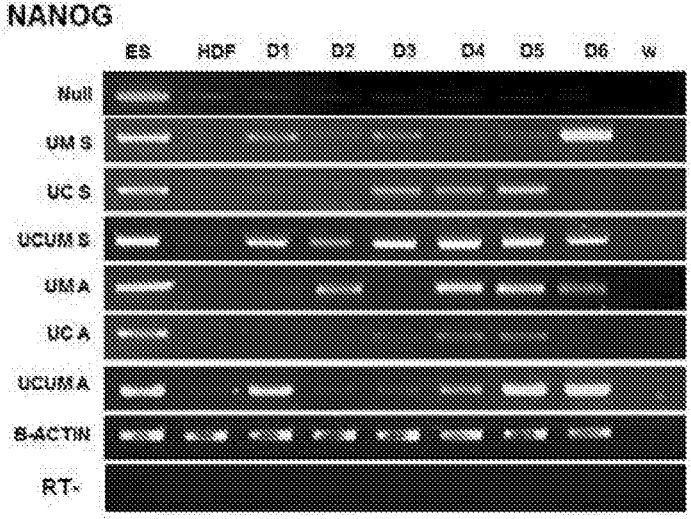
FIG. 9B shows RT-PCR analysis results of comparing expression levels of the pluripotent marker gene, NANOG (c) and TDGF1 (d) in the human Physics cells between the suspension culture condition and the monolayer culture condition.
Figure 9B:
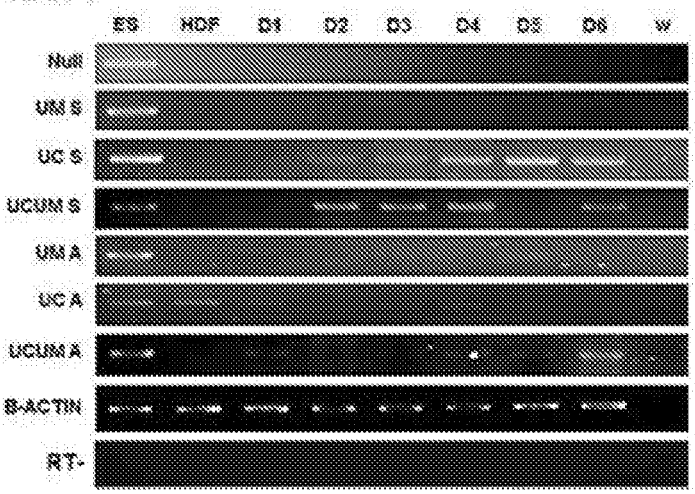

From the analysis results using RT-PCR, the undifferentiated marker genes were stably expressed when both the HDFs and the culture medium were treated with ultrasound, as shown in FIG. 9. In particular, when the HDFs were suspension-cultured, the undifferentiated marker genes were expressed at a higher level, compared to the monolayer-cultured cells.

To determine a difference in formation of the spheroids having an undifferentiation property under culture environments, expression levels of the undifferentiated marker OCT3/4 under the suspension or monolayer culture conditions were compared. For this purpose, the cells cultured for a culture time (0, 1, 2, 3, 4, 5 and 6 days) after the ultrasound treatment were fixed with 4% paraformaldehyde for 30 minutes, and then exposed to a PBS buffer supplemented with 0.1% Triton X100 for 40 minutes to improve a penetration ability of antibodies. Thereafter, the cells were blocked with a PBS buffer supplemented with 5% non-goat serum at room temperature for 30 minutes to prevent a non-specific protein reaction. Then, the cells were washed, and a primary antibody (OCT4; 1:200, Abcam) was added. The resulting mixture was reacted overnight at 4° C., and washed three times with a PBS buffer supplemented with 0.03% Triton X100. Then, a secondary antibody (IgG anti-rabbit conjugate Alexa 488) was diluted 1:1000 with a D-PBS buffer, and the cells were stained at room temperature for 2 hours. The stained cells were washed 4 times with a PBS buffer supplemented with 0.03% Triton X100, a DAPI-added mounting solution was sprayed on a slide so that the slide was covered with a cover slip, and edges of the slide were sealed with nail polish. Then, the cells were observed under a confocal laser microscope.

Figure 10A:
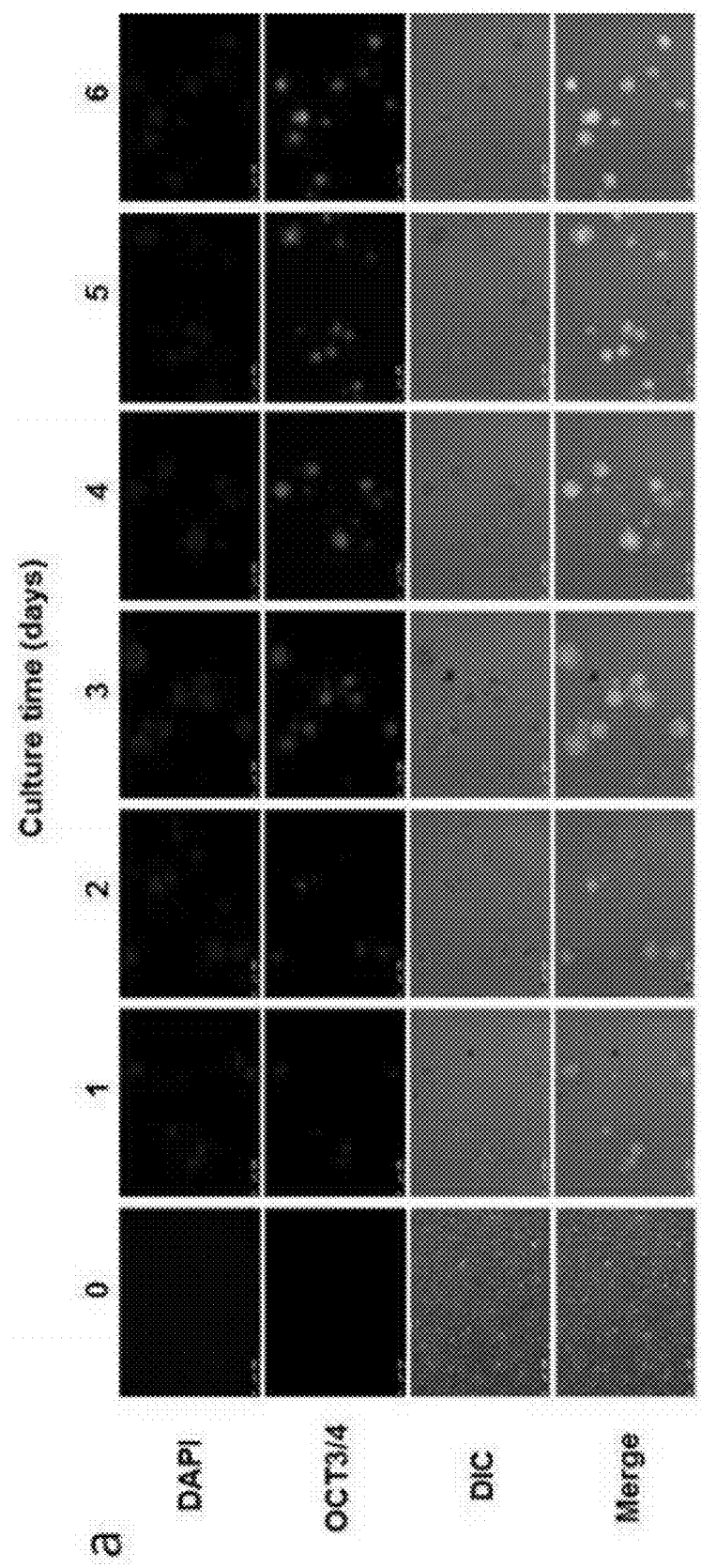
FIG. 10A is a confocal laser microscope image of OCT3/4 whose expression level is analyzed during suspension culturing.
Figure 10B:
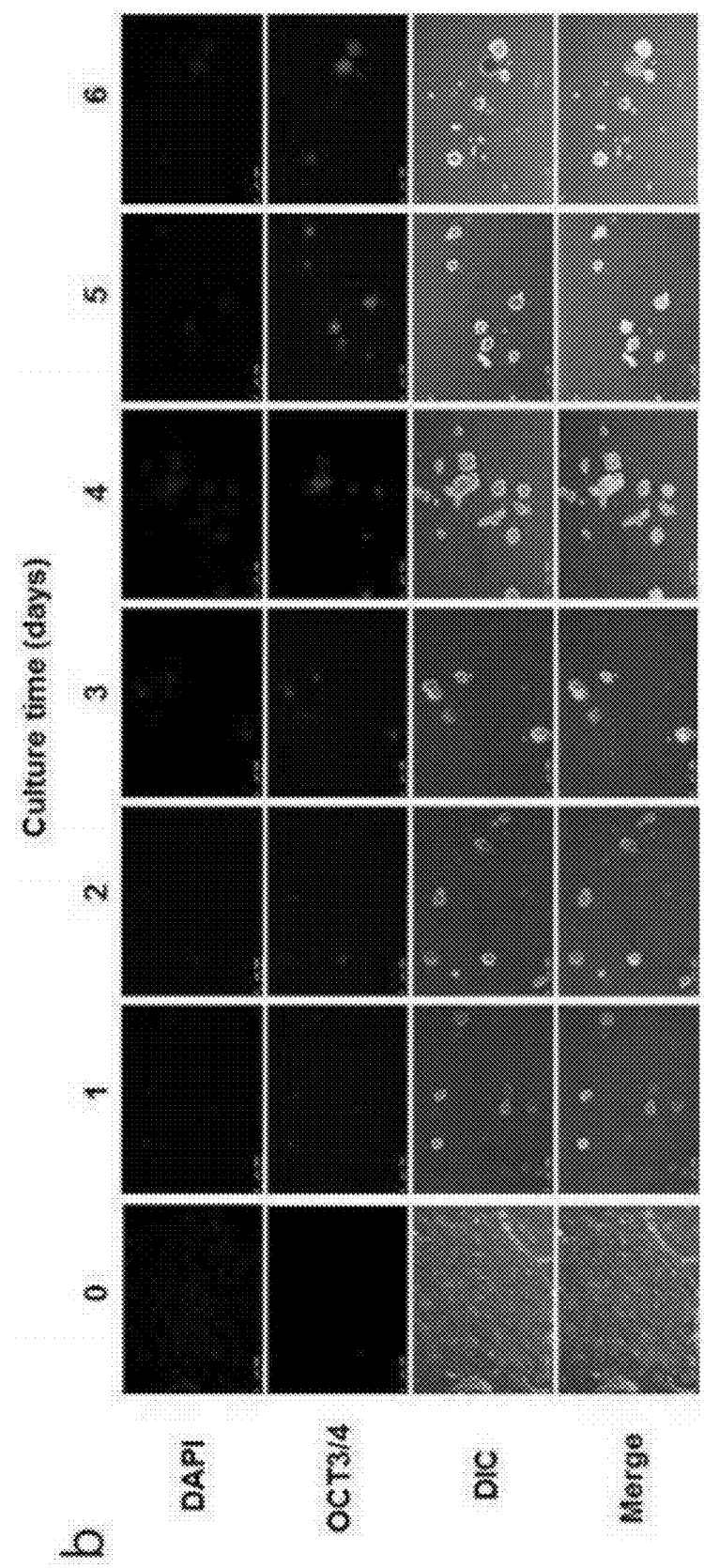
FIG. 10B is a confocal laser microscope image of the OCT3/4 whose expression level is analyzed during monolayer culturing.

As shown in FIG. 10, interestingly, the OCT3/4 expression was detected immediately one day after ultrasound treatment under the UCUM conditions. The OCT3/4 expression gradually increased, and a level of the OCT3/4 expression was higher under the suspension culture condition, compared to the monolayer culture condition.

Figure 11:
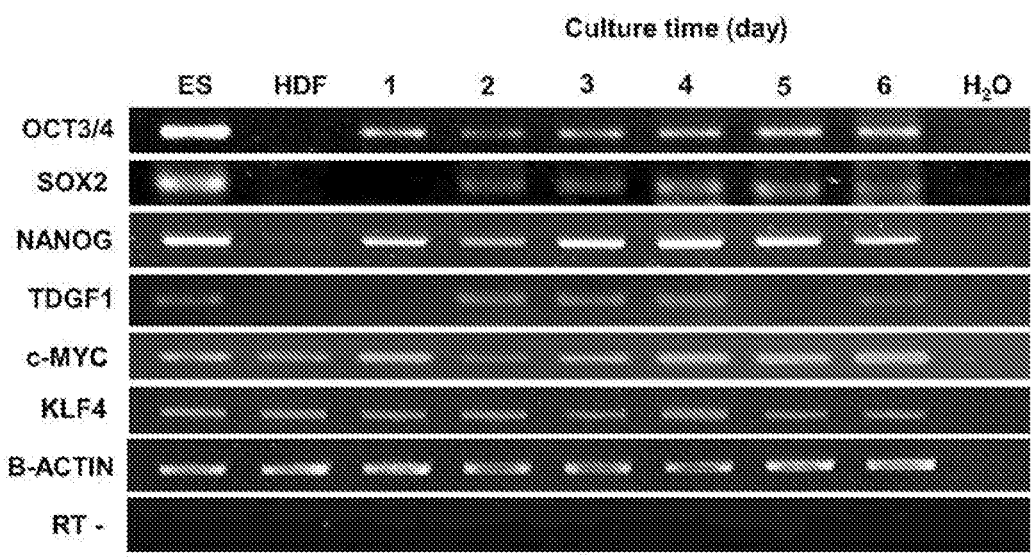
FIG. 11 shows RT-PCR analysis results of expression of pluripotent marker genes for a culture time of 6 days.
Figure 12:
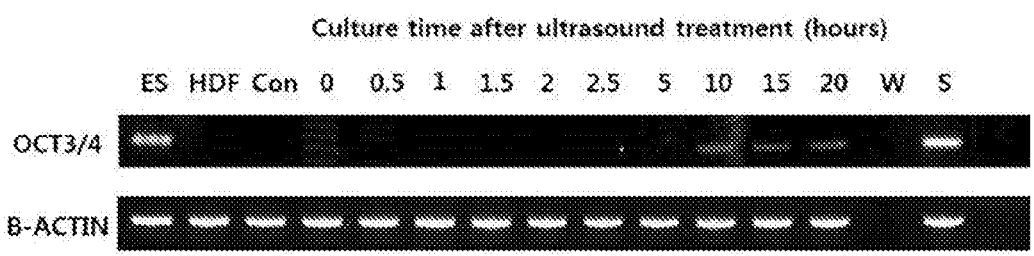
FIG. 12 shows RT-PCR analysis results of determining an expression stage of OCT3/4 in ultrasound-treated HDF spheroids in different culture time.

Subsequently, six undifferentiated marker genes, that is, OCT3/4, SOX2, NANOG, TDGF1, c-MYC and KLF4 were analyzed by RT-PCR for 6 days of suspension culture in which the spheroids were cultured under the UCUM condition. As a result, as shown in FIG. 11, the expression of the OCT3/4 and NANOG genes increased on day one after treatment, and the expression of the other genes also had increased as culture time passed. The expression of all the marker genes was observed on day 2, and the stable expression of the marker genes was observed after 3 days. The OCT3/4 expression was first observed 10 hours after ultrasound treatment (FIG. 12).

Figure 13:
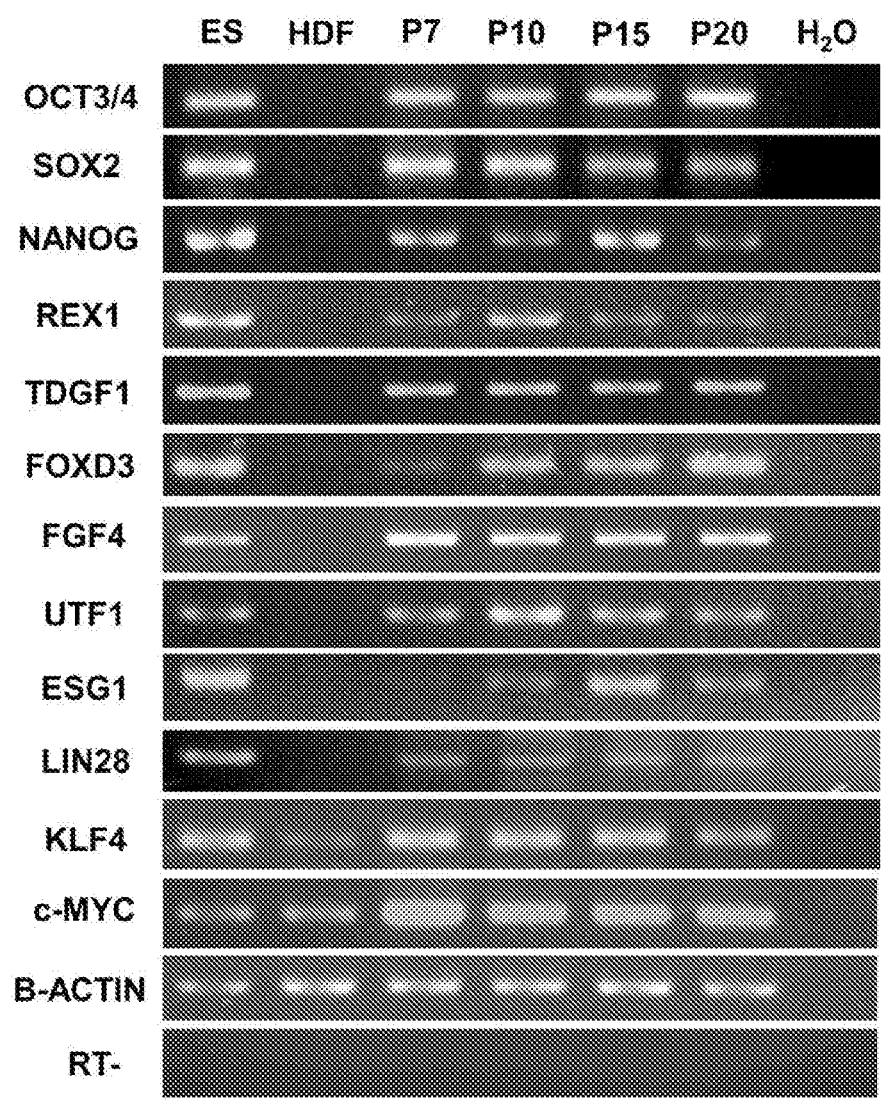
FIG. 13 shows results of determining the expression of representative undifferentiated markers in ES cells, HDFs and human Physics cells.

To check the undifferentiation capacity of the Physics cells, four randomly selected spheroids were subjected to RT-PCR. As a result, expression of the pluripotent marker genes including OCT3/4, SOX2, NANOG, REX1, TDGF1, FOXD3, FGF4, UTF1, ESG1, LIN28a, KLF4, and c-MYC was confirmed, and compared to the human H9 ESC and normal HDFs (FIG. 13). An experiment was performed as follows: The Physics cells cultured for 5 days were collected, and mRNA was extracted using a Dynabeads mRNA direct kit (Ambion). Thereafter, SuperScript-II (Invitrogen) cDNA was synthesized, PCR-amplified using the primers as listed in Table 2, and then subjected to electrophoresis

TABLE 2

| Gene names | Primer sequences (5' → 3') | |
|---|---|---|
| OCT3/4 | F GACAGGGGGAGGGGAGGAGCTAGG | SEQ ID NO.: 1 |
| | R CTTCCCTCCAACCAGTTGCCCCAAAC | SEQ ID NO.: 2 |
| SOX-2 | F GGGAAATGGGAGGGGTGCAAAAGAGG | SEQ ID NO.: 3 |
| | R TTGCGTGAGTGTGGATGGGATTGGTG | SEQ ID NO.: 4 |
| NANOG | F CAGCCCCGATTCTTCCACCAGTCCC | SEQ ID NO.: 5 |
| | R CGGAAGATTCCCAGTCGGGTTCACC | SEQ ID NO.: 6 |
| c-Myc | F AAACACAAACTTGAACAGCTAC | SEQ ID NO.: 7 |
| | R ATTTGAGGCAGTTTACATTATGG | SEQ ID NO.: 8 |
| KLF4 | F CCCACATGAAGCGACTTCCC | SEQ ID NO.: 9 |
| | R CAGGTCCAGGAGATCGTTGAA | SEQ ID NO.: 10 |
| UTF1 | F CCGTCGCTGAACACCGCCCTGCTG | SEQ ID NO.: 11 |
| | R CGCGCTGCCCAGAATGAAGCCCAC | SEQ ID NO.: 12 |
| LIN28 | F AGCGCAGATCAAAAGGAGACA | SEQ ID NO.: 13 |
| | R CCTCTCGAAAGTAGGTTGGCT | SEQ ID NO.: 14 |
| REX1 | F CAGATCCTAAACAGCTCGCAGAAT | SEQ ID NO.: 15 |
| | R GCGTACGCAAATTAAAGTCCAGA | SEQ ID NO.: 16 |
| FGF4 | F CTACAACGCCTACGAGTCCTACA | SEQ ID NO.: 17 |
| | R GTTGCACCAGAAAAGTCAGAGTTG | SEQ ID NO.: 18 |
| FOXD3 | F AAGCTGGTCGAGCAAACTCA | SEQ ID NO.: 19 |
| | R CTCCCATCCCCACGGTACTA | SEQ ID NO.: 20 |
| ESG1 | F ATATCCCGCCGTGGGTGAAAGTTC | SEQ ID NO.: 21 |
| | R ACTCAGCCATGGACTGGAGCATCC | SEQ ID NO.: 22 |
| TDGF1 | F CTGCTGCCTGAATGGGGAACCTGC | SEQ ID NO.: 23 |
| | R GCCACGAGGTGCTCATCCAT-CACAAGG | SEQ ID NO.: 24 |
| B-ACTN | F CATGTACGTTGCTATCCAGGC | SEQ ID NO.: 25 |
| | R CTCCTTAATGTCACGCACGAT | SEQ ID NO.: 26 |

Figure 14:
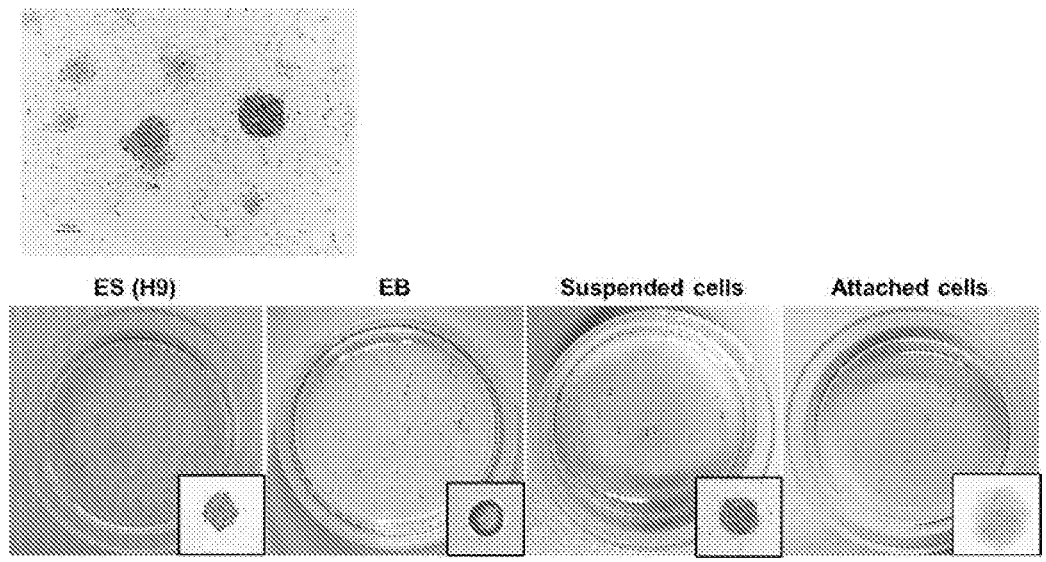
FIG. 14 shows alkaline phosphatase staining results for characterizing a pluripotent state of the multicellular spheroids.

From the alkaline phosphatase (AP) staining results, it was confirmed that the multicellular spheroids had pluripotent characteristics. The suspension-cultured spheroids had a more distinct red color than the monolayer-cultured spheroids (FIG. 14).

Figure 15:
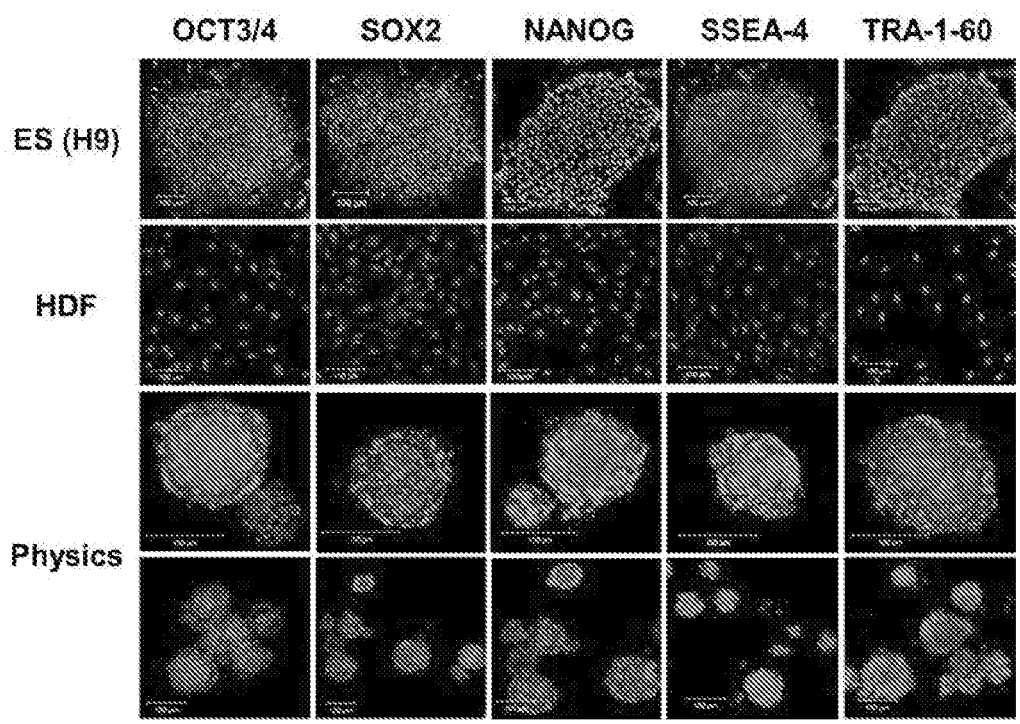
FIG. 15 shows immunocytochemical results of expression of pluripotent markers.
Figure 16A:
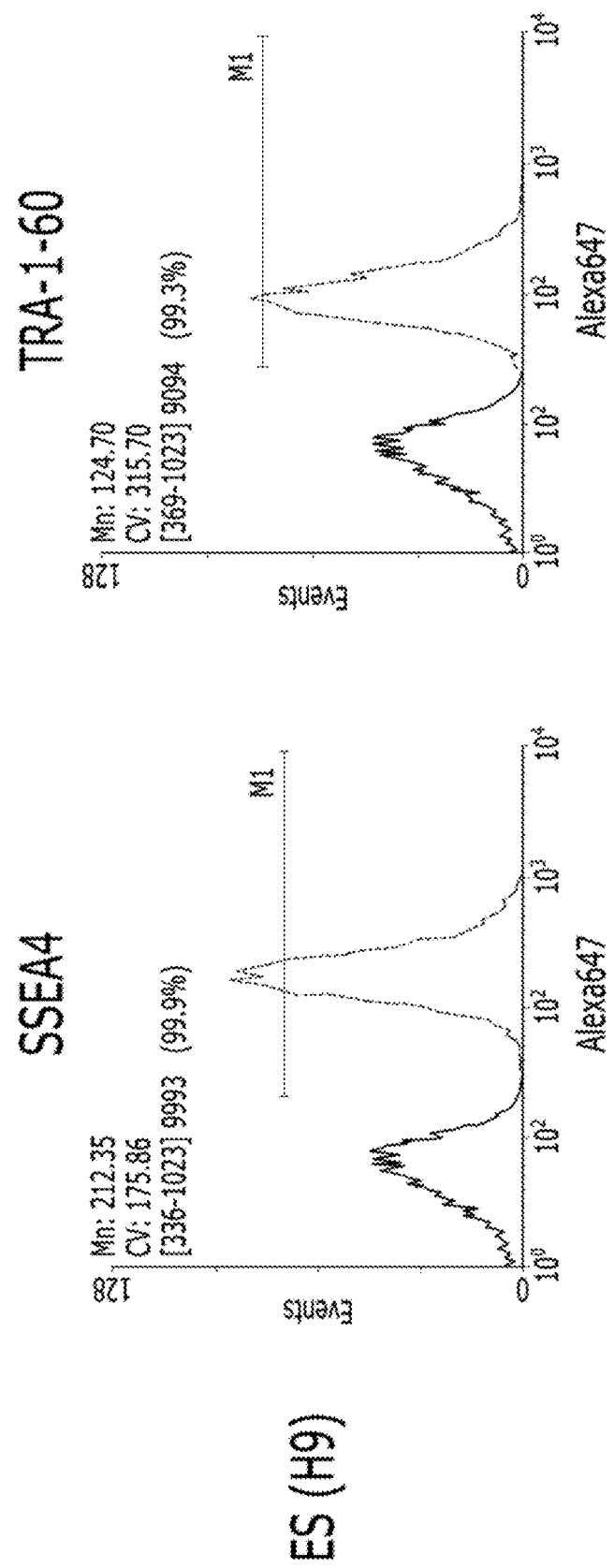
FIG. 16A shows FACS analysis results of a human ES (H9) cell surface marker.
Figure 16B:
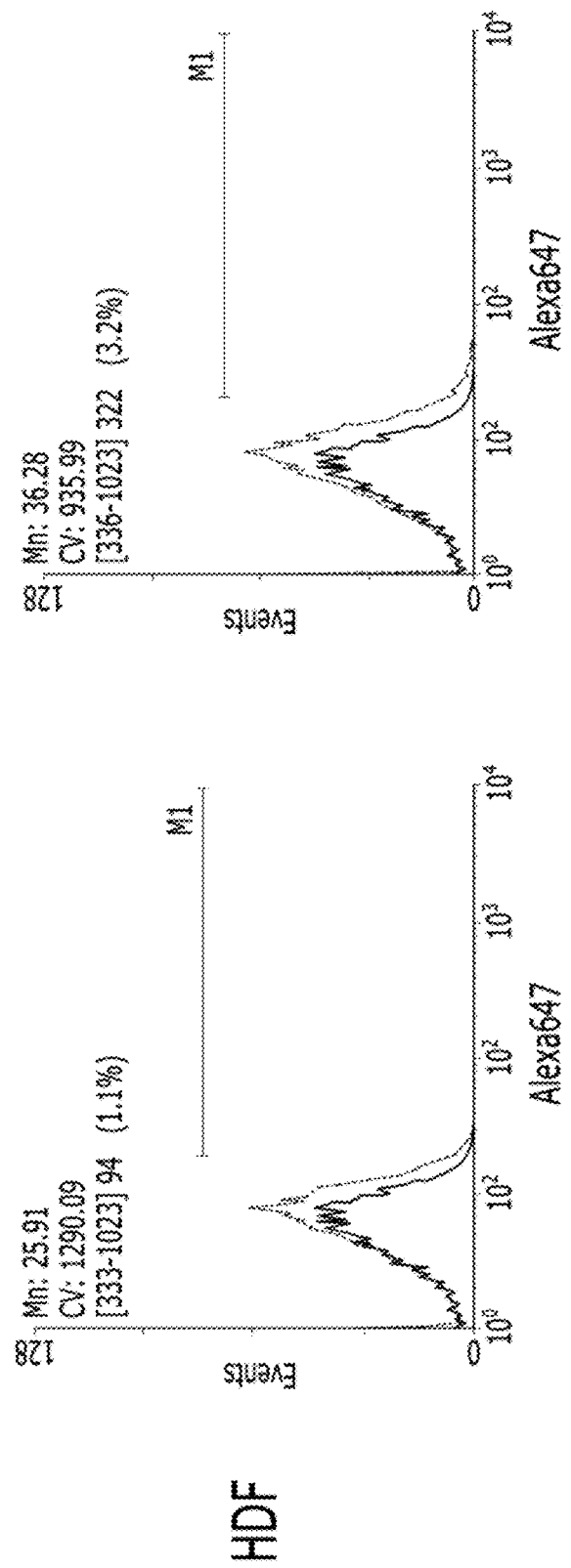
FIG. 16B shows FACS analysis results of a human HDF cell surface marker.
Figure 16C:
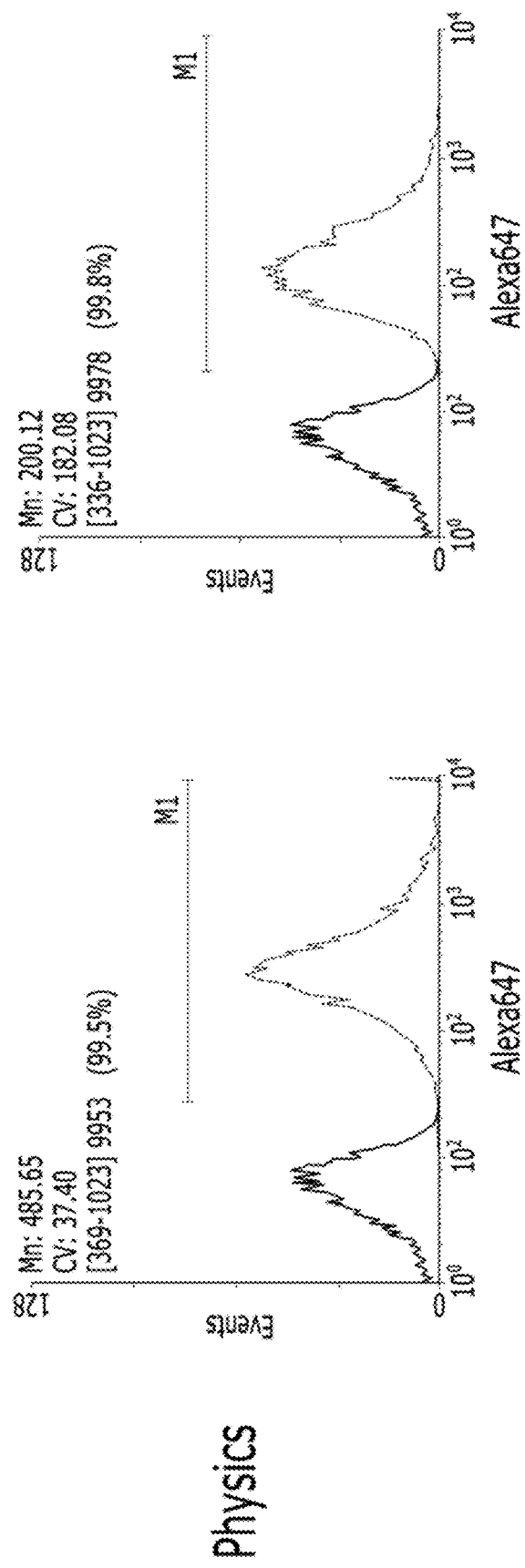
FIG. 16C shows FACS analysis results of a human Physics cell surface marker.

The expression of OCT3/4, SOX2, NANOG, SSEA-4 and TRA-1-60 was similar to that of the H9 human ES cells (FIG. 15). Also, the pluripotent characteristics of the multicellular spheroids were determined through flow cytometry (FIG. 16). More than 99.5% of SSEA4 and TRA-60 were expressed in the spheroids, and an expression level of each of the SSEA4 and TRA-60 was similar to that of the H9 human ES cells.

Figure 17:
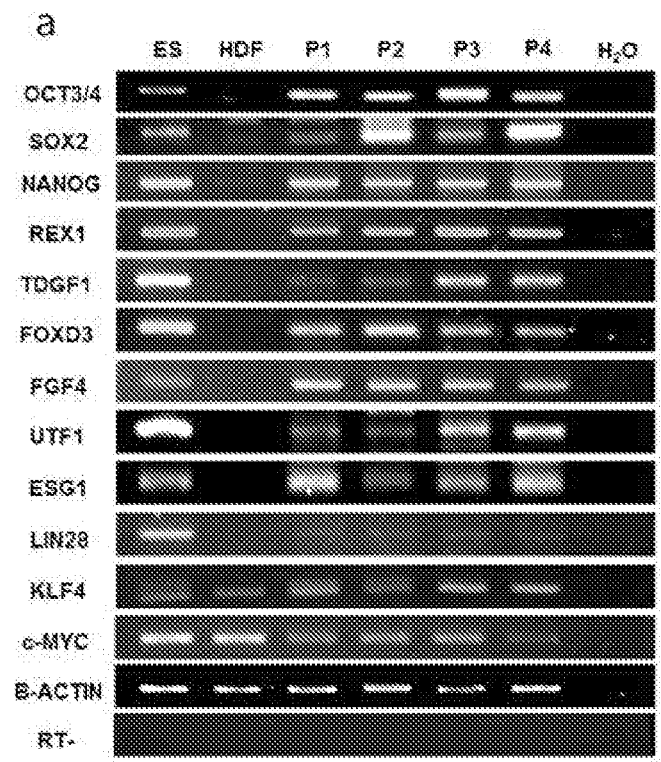
FIG. 17 show results of analyzing (a) gene expression of the pluripotent markers using RT-PCR and (b) protein expression of the pluripotent markers using an immunocytochemical method when feeder cells and Physics cells are co-cultured.
Figure 17:
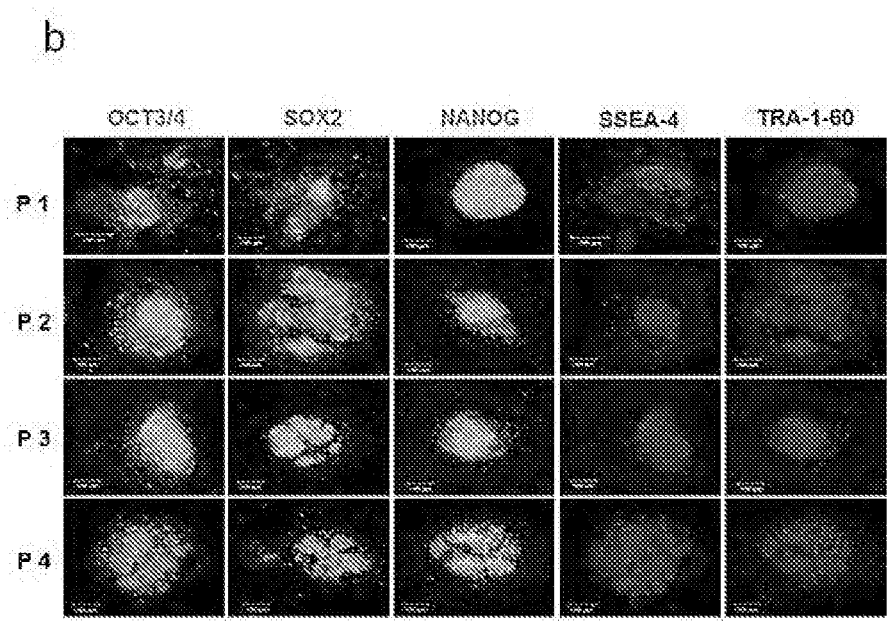

Also, when the spheroids were transferred and co-cultured with mouse embryonic fibroblast (MEF) feeder cells in a gelatin-coated tissue culture plate, cell spreading and growth were observed. Also, the expression of the pluripotent marker genes was sustained (FIG. 17).

In addition, to further check the expression of the undifferentiated markers, a DNA methylation assay was performed. It can be seen that, when a promoter region in which the gene expression is initiated is methylated, the gene expression is not initiated in this region. This means that, when the promoter region is demethylated, that is, a methyl group is removed from DNA, a gene is expressed from the promoter region. Therefore, to check whether the OCT3/4 and NANOG genes were expressed as the main genes of the undifferentiated stem cells, it was determined whether the promoter regions of the two genes were methylated.

For this purpose, DNA was extracted from the Physics spheroids using proteinase K and phenol, and the methylation of OCT3/4 and NANOG DNAs in the Physics spheroids was analyzed using an EZ DNA methylation kit (Zymo Research). Primers for DNA amplification used for analysis are as follows.

1) Primers for amplification of human NANOG:

```
Forward primer:
5'-TAGGAGTAGAGTGTAGAGGAGAATGAGTTA-3'

Reverse primer:
5'-ATCTATCCCTCCTCCCAAATAATC-3'
```

Size of amplified product: 377 bp, $T_m$: 55° C., and CpGs in the product: 6

2) Primers for amplification of human OCT4:

```
Forward primer:
5'-TTTTTTTAAATTAGAAATTTTAATTATTTG-3'

Reverse primer:
5/-AATTACAAAAACCATACCTACAACC-3'
```

Size of amplified product: 417 bp, $T_m$: 55° C., and CpGs in the product: 4

Figure 18:
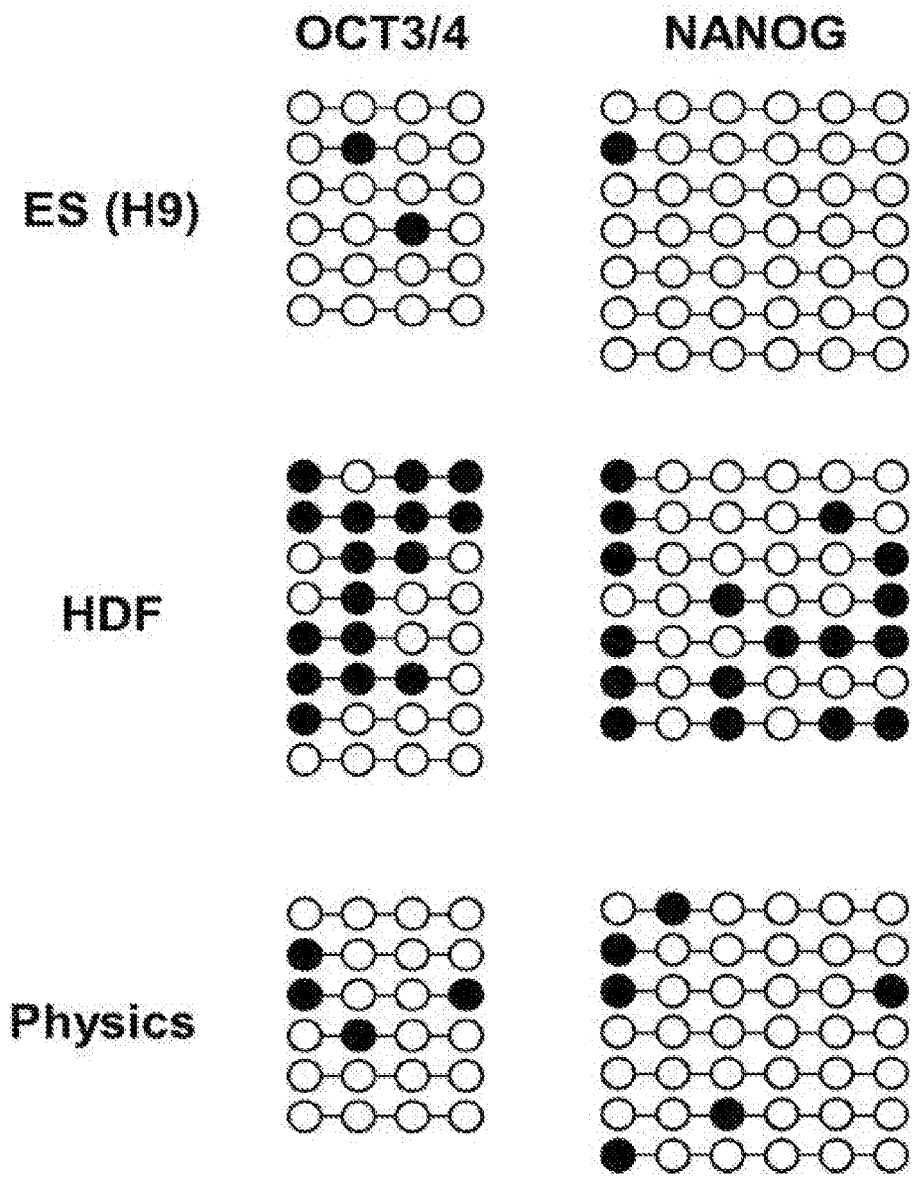
FIG. 18 shows bisulfite genomic sequencing results showing methylation states of COT3/4 and NANOG promoters.

In case of the methylation of cytosine-guanine dinucleotides (CpG) in the promoter regions of the pluripotency-specific OCT3/4 and NANOG genes evaluated by bisulfite genomic sequencing, the Physics cells were highly demethylated at a level similar to the ES cells, but the CpG dinucleotides of these regions in the original HDFs exhibited low demethylation (FIG. 18). These results suggest that the OCT3/4 and NANOG promoters were activated by the ultrasound treatment.

<Example 2> Proliferative Capacity and Pluripotent Capacity of Physics Cells

The proliferative capacity of the Physics cells was evaluated using a method of immunostaining a proliferation marker protein Ki-67 and differential nuclear staining using Hoechst 33342 and propidium iodide (PI).

Figure 19:
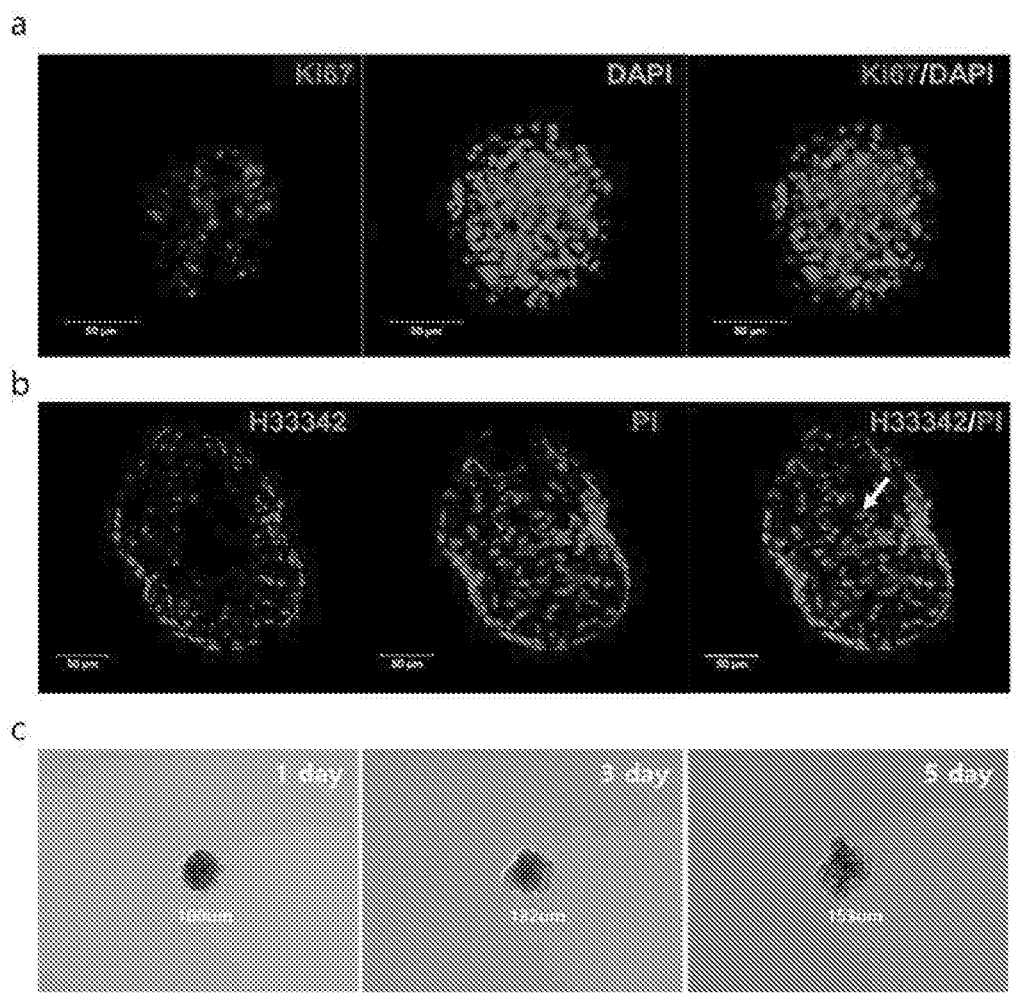
FIG. 19 shows experimental results of verifying the proliferative capacity of the human Physics cells: a) shows results showing expression of Ki67 which is a proliferation marker, b) shows results of staining increased cells using H33342 and PI, and c) show the sizes of the spheroids in different culture time.

As shown in FIG. 19, the expression of Ki-67 in the Physics cells was observed on day 5.

To verify the proliferative capacity of the Physics cells more clearly, cell proliferation was confirmed using a method as described below. The cultured Physics cells were stained on day 5 using Hoechst 33342 capable of staining the nuclei of the live cells due to good penetrability. After a staining reagent was completely removed, the Physics cells were cultured for 3 days. Thereafter, the cultured Physics cells were fixed with 4% paraformaldehyde for a total of 8 days, and the cell nuclei was further stained with PI. A non-overlapping red signal represents Physics cells newly formed by cell division after 5 days. Also, single spheroids were cultured for 5 days, and diameters of the spheroids were then measured on moving images. As a measurement result shows an increase in size, the proliferative capacity of the Physics cells was proven.

To evaluate the self-renewal capacity of the Physics cells, the Physics cells stained with Hoechst 33342 were cultured for another 5 days, fixed with 4% paraformaldehyde, and then stained again with PI and OCT3/4. PI signals represent the nuclei in the Physics cells. The nuclei counterstained with OCT3/4 nearly merging with Hoechst 33342 meant that the Physics cells were stained with Hoechst 33342 before day 5.

Figure 20:
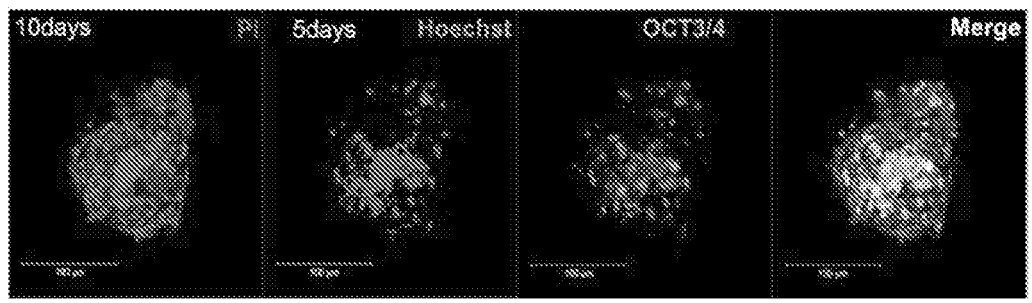
FIG. 20 shows experimental results of verifying the self-renewal capacity of the human Physics cells.

As shown in FIG. 20, the pluripotent characteristics (OCT3/4) were not inherited by daughter Physics cells during 5 days of further culture. These results suggest that the Physics cells were able to proliferate, but were not self-renewed after 5 days.

Figure 21A:
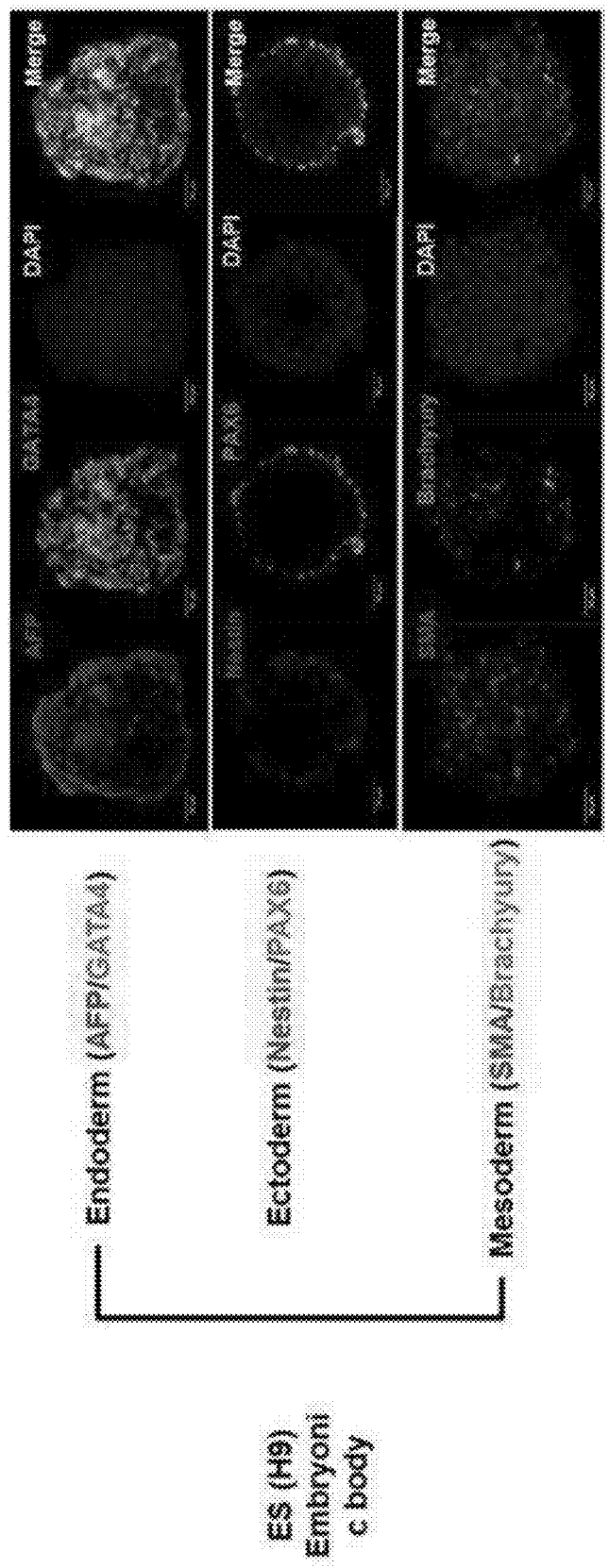
FIG. 21A shows immunocytochemical analysis results of a three germ layer marker expressed in human ES (H9) cells.
Figure 21B:
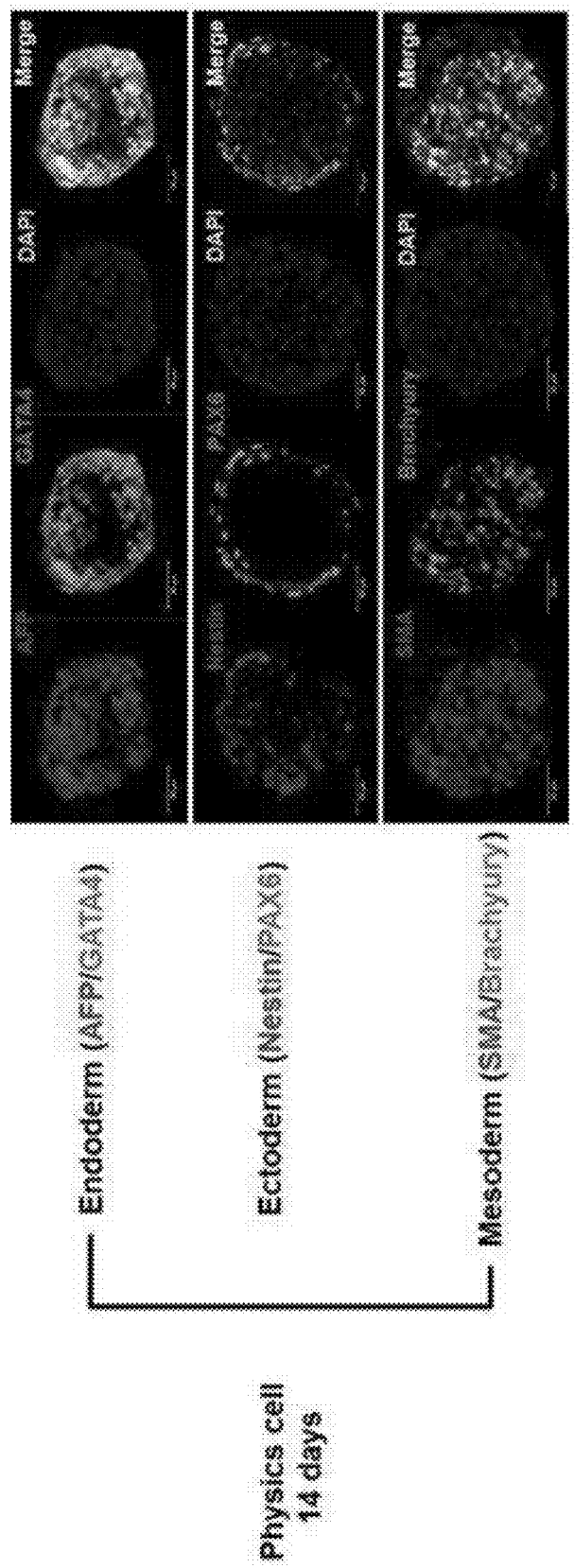
FIG. 21B shows immunocytochemical analysis results of the three germ layer marker expressed in human Physics cells.

Also, the expression of the specific marker genes in each of the germ layers was detected during an initial culture period of the Physics cells. A unique gene expression pattern of the Physics cells expressing both the undifferentiated and differentiated markers was comparable to embryoid body (EB) derived from human ESCs (FIG. 21). This is because the Physics cells and EB have a very similar shape.

Figure 22:
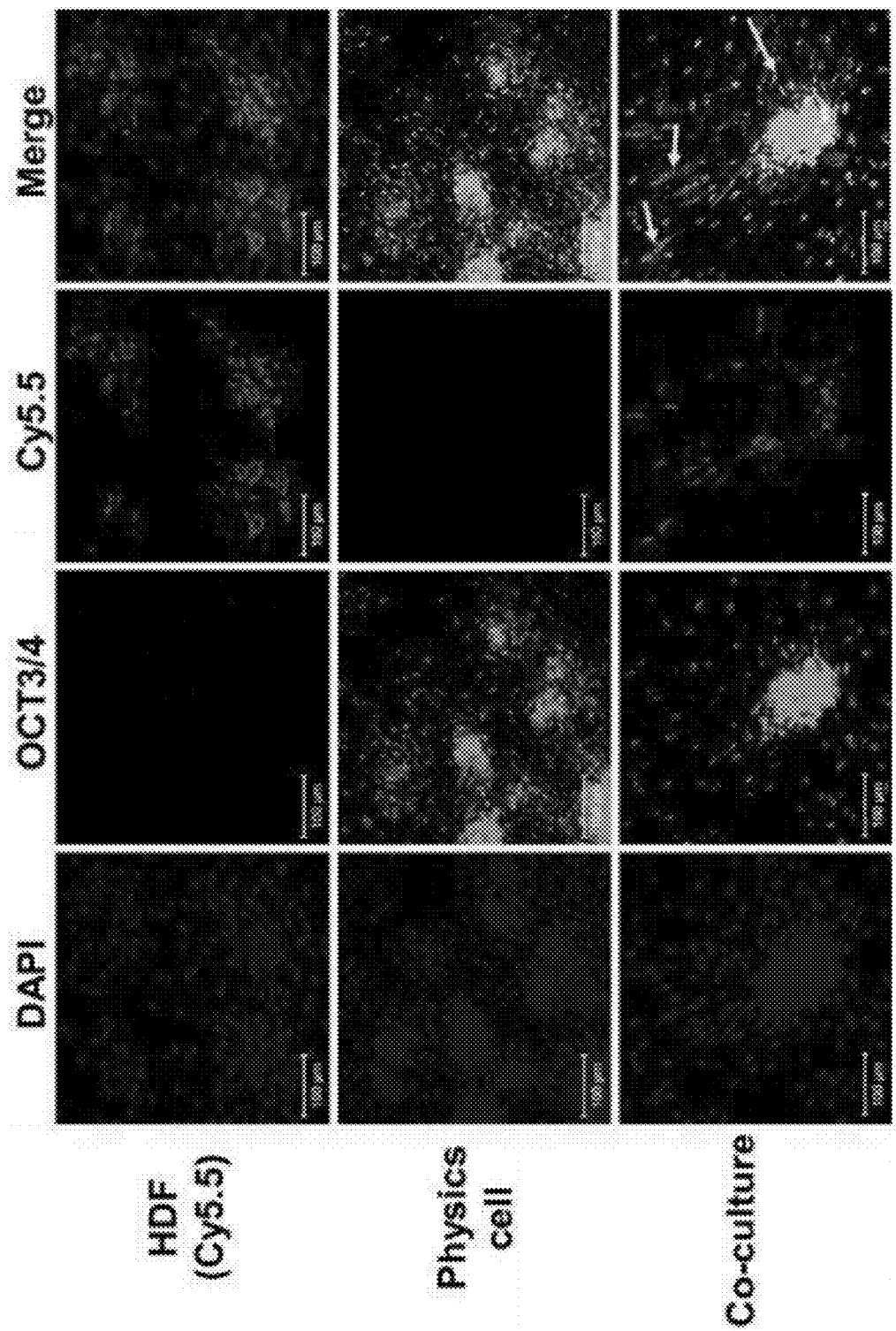
FIG. 22 shows immunocytochemical analysis results of expression patterns of OCT3/4 and the three germ layer marker during 15 days of culturing the human Physics cells.

From the immunocytochemical analysis results, it was revealed that the endoderm (GATA4 and AFP), ectoderm (PAX6 and Nestin), mesoderm (Brachyury and SMA) markers were expressed at a high level in the Physics cells and EB. In addition to the OCT3/4, the expression of PAX6 was also detected on the first day after the ultrasound treatment. The expression of the other genes of the three germ layers began on day 3 after formation of the Physics cells. The expression levels of the three germ layer markers gradually increased during the 15 days of culture. However, the OCT3/4 expression decreased after day 8 (FIG. 22).

<Example 3> Cellular Change by Ultrasound Stimulation

Different ultrasonic conditions were compared to evaluate the effect of ultrasonic stimuli to the HDFs during the generation of Physics cells. An SEM assay was directly performed after the ultrasound treatment and after 2 hours of culture of ultrasound-treated HDFs.

Figure 23:
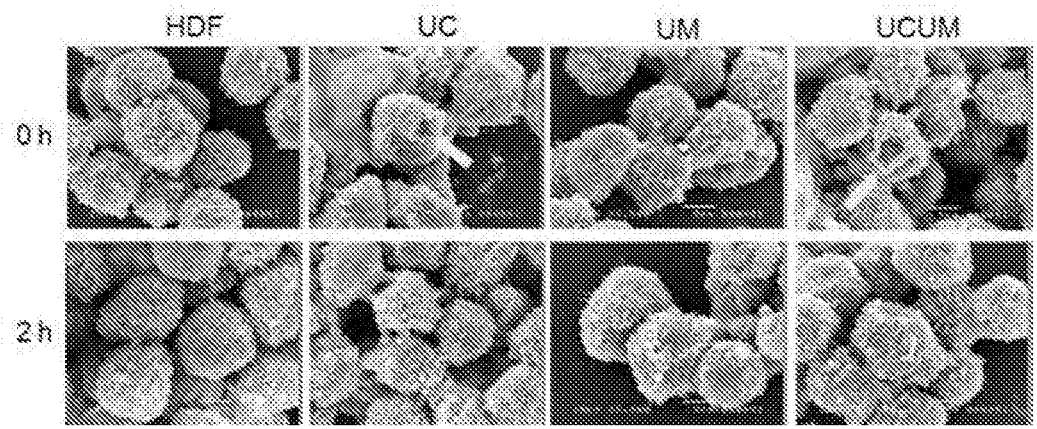
FIG. 23 shows an SEM image of the human Physics cells in different ultrasound stimulation conditions.

As shown in FIG. 23, some cell membrane pores were formed under both the UC and UCUM conditions. Perhaps, it appears to be because the HDFs were directly exposed to ultrasound. However, no pores were formed across the cell membranes in the HDFs under the UM conditions. This was because the cell membranes were not sufficiently damaged when only the culture medium was treated with ultrasound. In particular, after 2 hours of cell culture, the formed pores disappeared under both the UC and UCUM conditions. These results suggest that the ultrasound stimulation was not severe enough to induce apoptosis but was sufficient to induce transient permeation through the plasma membranes, and the damaged plasma membranes were then repaired during an initial cell culture period.

Figure 24:
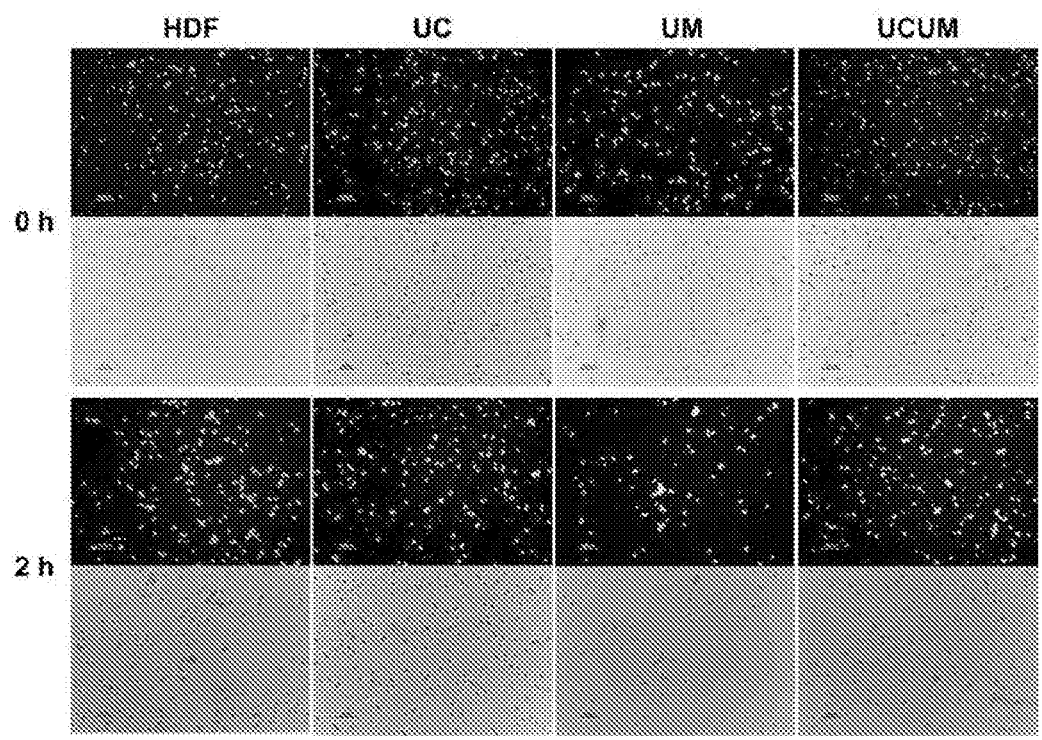
FIG. 24 shows results of live/dead cell assay of human Physics cells as viewed in a fluorescence image after ultrasound treatment and after 2 hours of culture under ultrasound stimulation conditions

The repair process of the damaged plasma membranes was also proven by cellular analysis using a live/dead kit (Green fluorescence in the case of cells whose cell membranes are not damaged/Red fluorescence in the case of dead cells or cells whose cell membranes are damaged). The HDFs were stained with a fluorescent reagent immediately after the ultrasound treatment and after 2 hours had elapsed. As a result, it was revealed that, since a percentage of the red fluorescence was reduced after 2 hours, the cell membranes damaged by ultrasound was repaired 2 hours after the ultrasound treatment, as shown in the SEM analysis results (FIG. 24).

Also, to determine the correlation between the cells stimulated with ultrasound and the formation of spheroids, using a reagent, ultrasound-treated HDFs were added to a live/dead kit, and green/red dually stained HDFs were traced for 24 hours using a live cell imaging apparatus.

Figure 25:
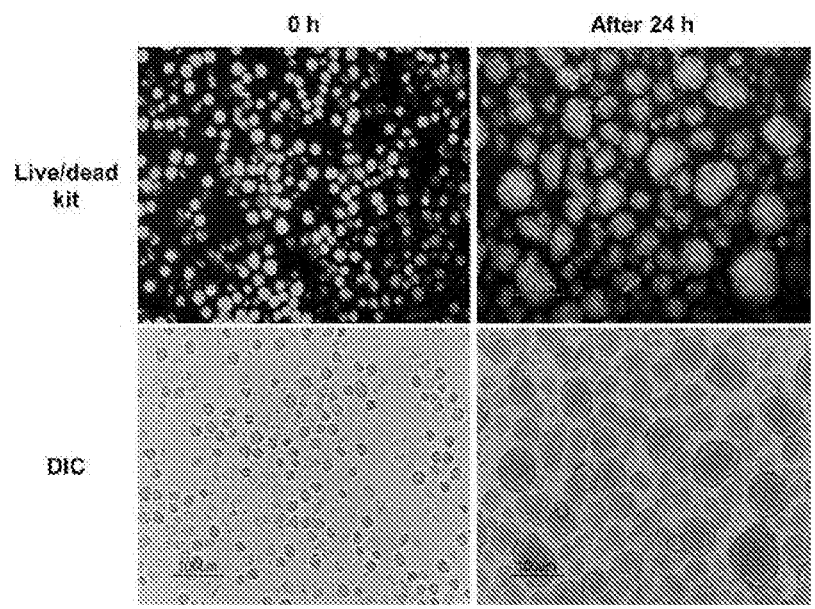
FIG. 25 shows results of the live/dead cell assay of human Physics cells after formation of the multicellular spheroids.

As shown in FIG. 25, the HDFs simply aggregated with other green-stained or red/green dually stained HDFs to form multicellular spheroids. After 24 hours, most of the slightly damaged HDFs formed stable Physics cells.

Figure 26:
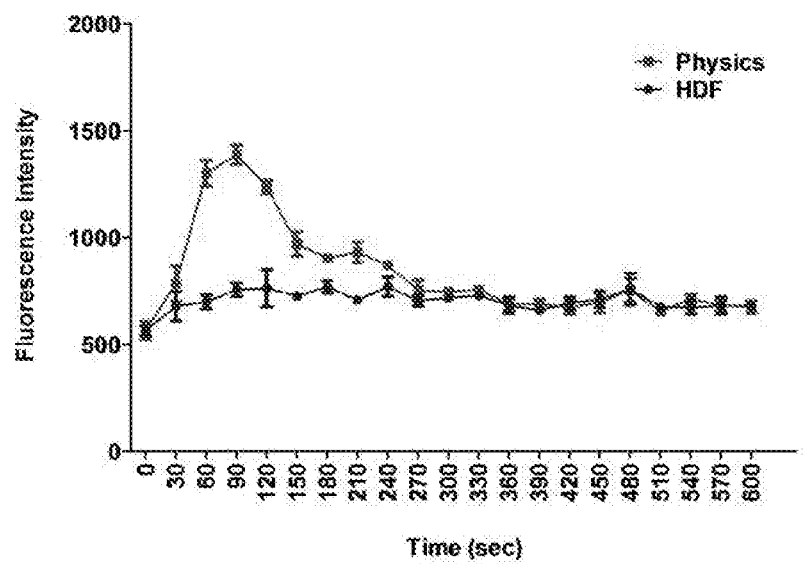
FIG. 26 shows changes in intracellular $Ca^{2+}$ concentrations by ultrasonic stimulus.
Figure 27:
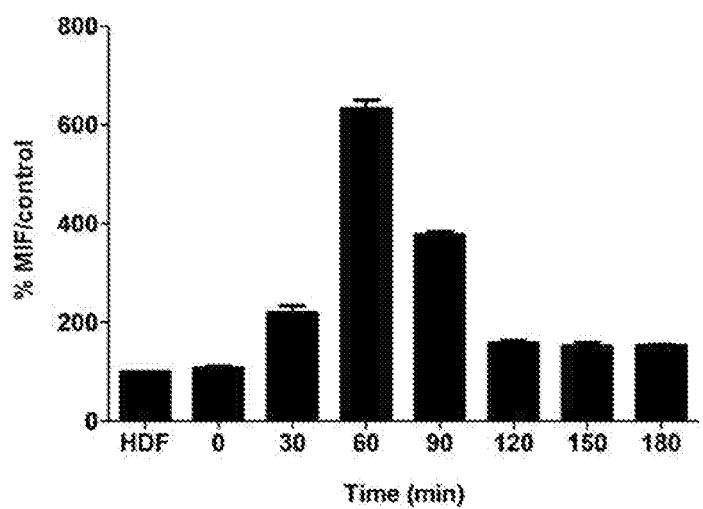
FIG. 27 shows results of analyzing generation of $H_2O_2$ by the ultrasonic stimulus.
Figure 28:
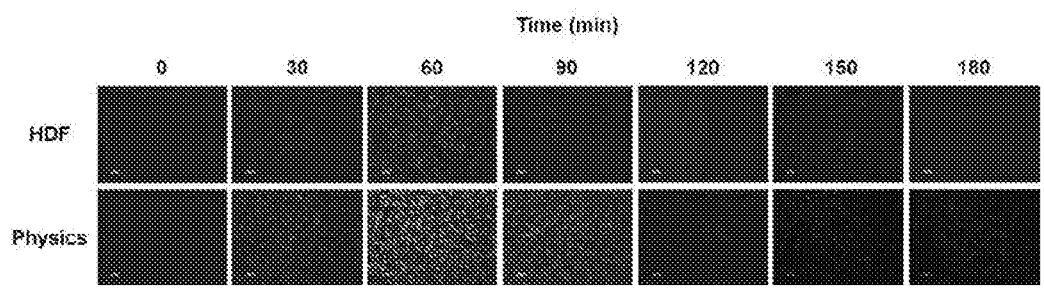
FIG. 28 is a fluorescence image of the human Physics cells stained with CM-H2DCFDA to analyze the generation of intracellular $H_2O_2$ by the ultrasound treatment as shown in FIG. 27.

The ultrasound-induced cell membrane damage and transient permeation were characterized by increased intracellular $Ca^{2+}$ concentration and intracellular $H_2O_2$ generation using a fluorescent dye (i.e., a Fluo-4 dye) and CM-H2DCFDA. As soon as the Physics cells were exposed to ultrasound, the $Ca^{2+}$ concentration in the Physics cells suddenly increased, and then decreased at 150 seconds (FIG. 26). The intracellular concentration of $H_2O_2$ in the Physics cells was six-fold higher than that of the untreated HDFs as the control after 60 minutes of ultrasound exposure (FIGS. 27 and 28).

Further, since ATP was used as a signal in response to various types of cellular stress, the concentration of ATP released from the cells was analyzed.

Figure 29:
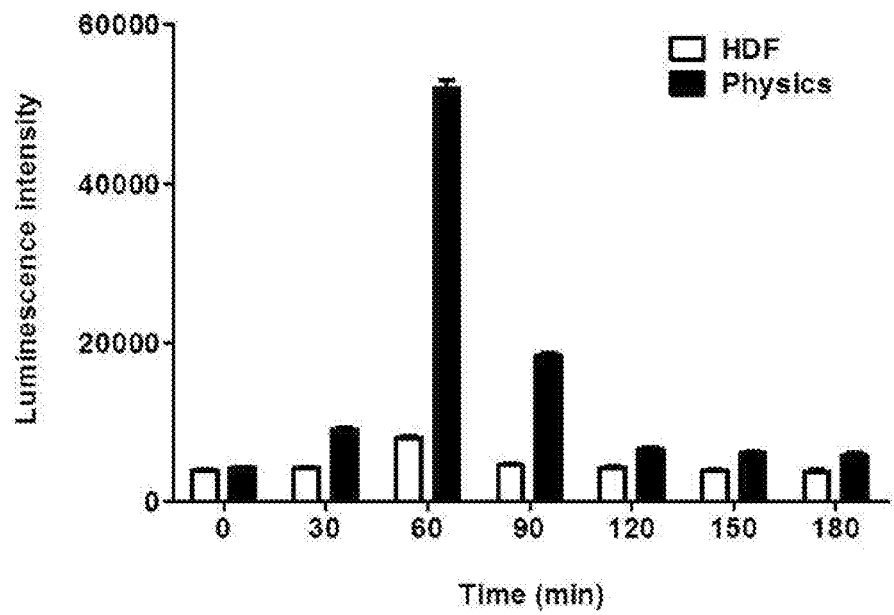
FIG. 29 shows results of analyzing release of intracellular ATP by the ultrasonic stimulus.

As shown in FIG. 29, the ultrasound stimulated the release of a 22-fold higher level of ATP from the Physics cells, compared to the untreated HDFs.

Because the expression of an ionotropic P2X receptor and a metabotropic P2Y receptor are known to be activated by the ATP release, expression levels of these receptors were compared.

Figure 30:
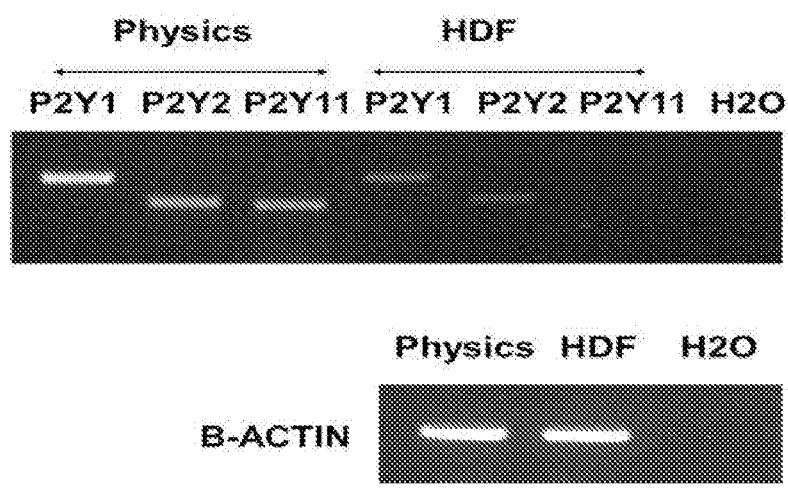
FIG. 30 shows expression patterns of P2X and P2Y receptors in the human Physics cells.

Higher levels of expression of P2X4, P2X7, P2Y1, P2Y2 and P2Y11 were detected in the Physics cells (FIG. 30). Improved cellular uptake into the Physics cells was further confirmed using Alexa-705-labeled quantum dots (QD705). QD705 was added to a culture dish, and confocal microscope images were obtained after 24 hours.

Figure 31:
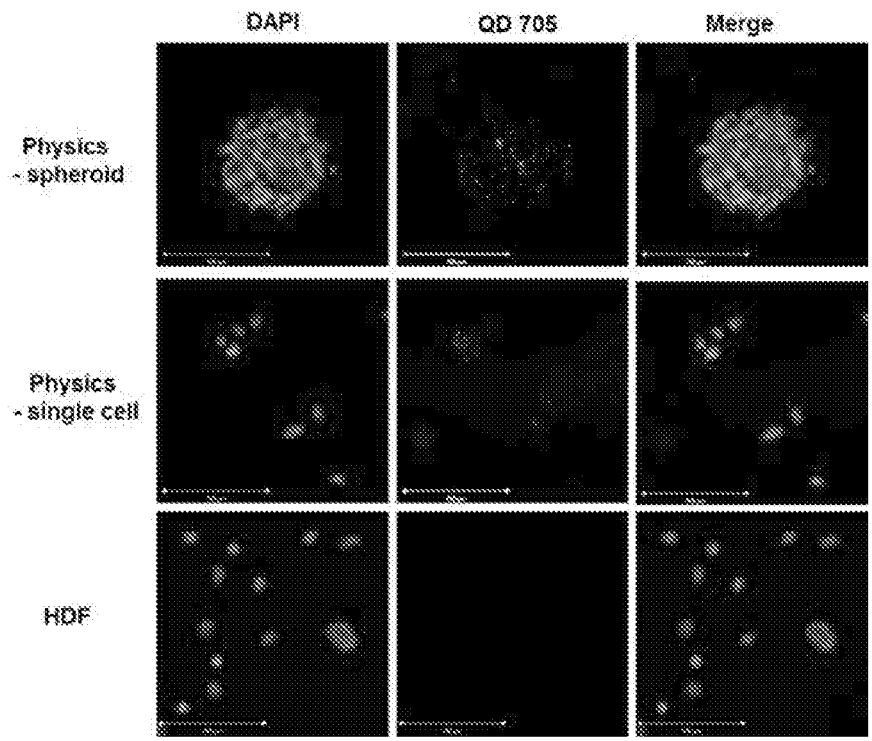
FIG. 31 is a confocal microscope image of proving a higher uptake capacity of the human Physics cells using Quantum dot 705.

Both a spheroid type of Physics cells and a single cell type of neighboring single Physics cells not aggregating with other Physics cells absorbed QD705. However, the normal HDFs did not absorb QD705 (FIG. 31). This proves that the cellular uptake of external elements was improved due to ultrasound stimulation.

Meanwhile, exosomal RNA was prepared from a Physics cell culture medium, and a gene expression pattern in a cell culture environment during Physics cell generation was studied through RT-PCR analysis. In general, an exosome includes several genetic elements, for example, RNA, microRNA, DNA, proteins. Also, an expression profile of the genetic elements in the exosome is cell status-dependent.

Figure 32:
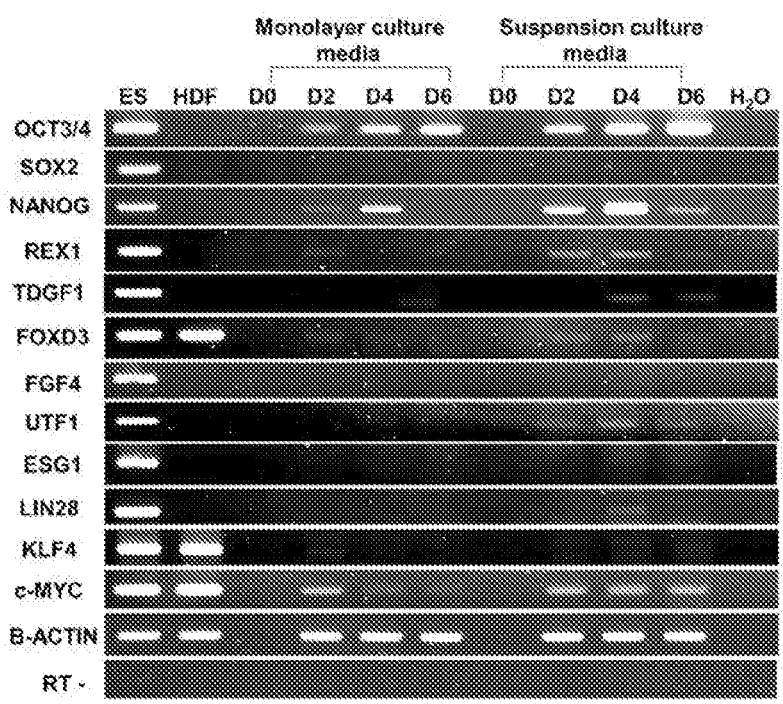
FIG. 32 shows RT-PCR analysis results of expression of pluripotent marker genes from an exosome in human Physics cell culture media.

As shown in FIG. 32, the highest expression level of the pluripotent marker genes was observed in a purified exosome from the Physics cell culture medium. The most outstanding gene expression was observed for OCT3/4 and NANOG. As culture time passed, the OCT3/4 expression remarkably increased. The NANOG expression dropped after 4 days. The c-MYC expression was constantly maintained under the suspension culture conditions, but dropped under the monolayer culture conditions after 2 days. The expression of all the pluripotent marker genes, for example, REX1, TDGF1, FOXD3, UTF1, and LIN28, was detected under the suspension culture conditions even when the pluripotent marker genes were expressed at a low expression level. However, these genes were not detected under the monolayer culture condition. These results suggest a probability of transferring the genetic elements in the ultrasound-treated HDFs.

To prove this hypothesis, HDFs not treated with ultrasound were co-cultured with the Physics cells. For imaging analysis, the HDFs were stained with a Cy5.5 red fluorescence dye using Lipofectamine. The Physics cells were prepared separately. After the Physics cells were maintained for 2 days, the Physics cells were added to a Cy5.5-stained HDF culture dish. During co-culturing, the culture medium was not treated with ultrasound. This is because the expression of the pluripotent marker genes was also induced under the UM condition.

Figure 33:
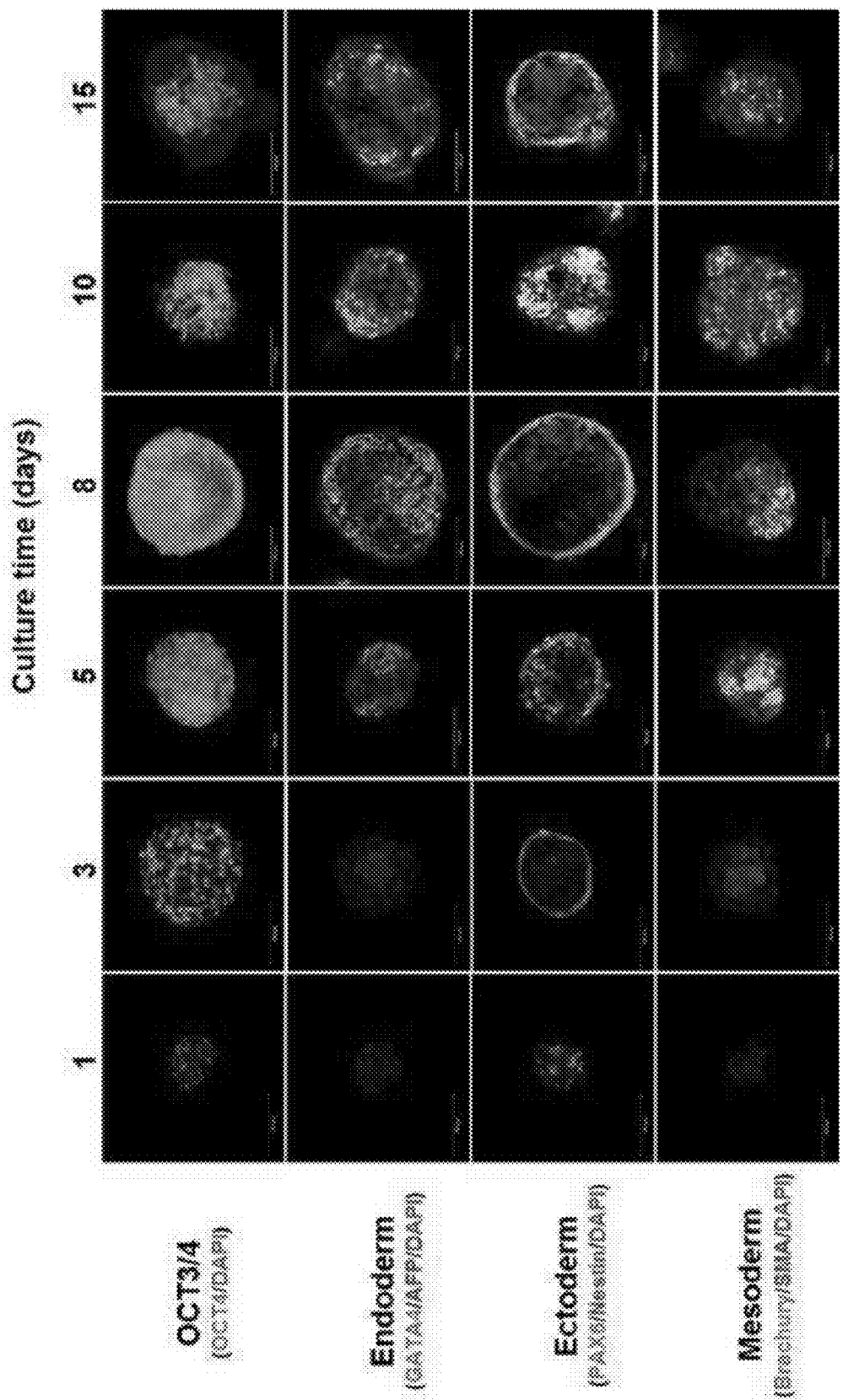
FIG. 33 shows immunocytochemical results showing a transport process into HDFs by exosomal OCT4 released from the human Physics cells: Yellow arrows indicate OCT3/4 expression in surrounding HDFs.

In the confocal microscope images, the OCT3/4 expression in the Cy5.5-stained HDFs was observed while being co-cultured with the Physics cells. The OCT3/4 expression was not detected when the Cy5.5-stained HDFs were cultured alone. These results strongly prove that the pluripotent characteristics of the Physics cells were inherited by neighboring normal cells, and the normal cells were then reprogrammed into the Physics cells. In general, the exosomes participated in transport of genetic elements in the cells (FIG. 33).

<Example 4> In Vitro Differentiation of Physics Cells

Figure 34:
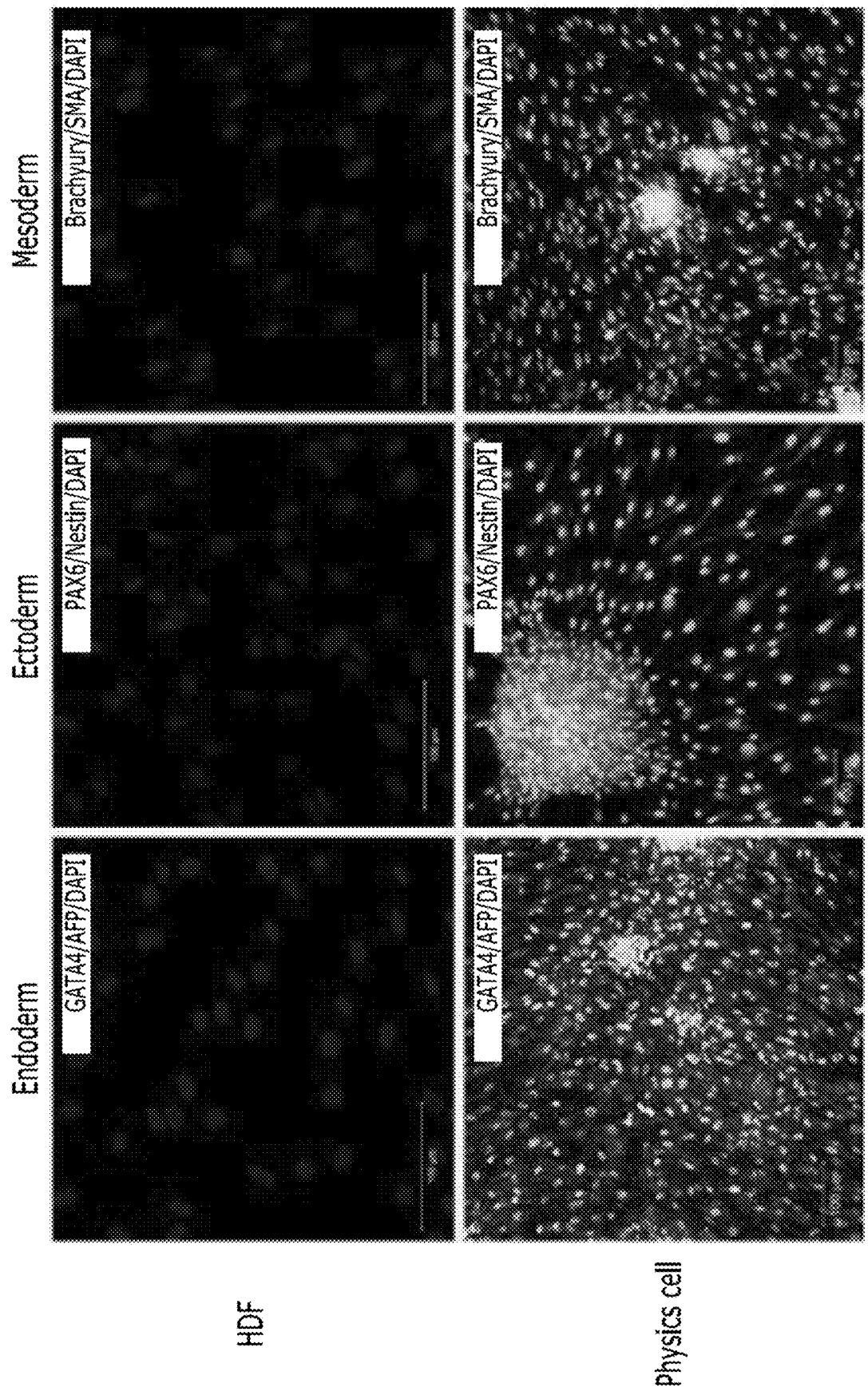
FIG. 34 shows immunocytochemical results of expression of the three germ layer marker after induction of in vitro differentiation of the human Physics cells.

For in vitro differentiation, Physics cells cultured for 5 days were transferred to a gelatin-coated tissue culture dish. The transferred cells were induced to differentiate into a neuronal or cardiac lineage using specific differentiation media. The specific differentiation media are listed in Table 3. Main three germ layer proteins (GATA4, AFP, PAX6, Nestin, Brachyury, and SMA) were expressed in the eight-day-old cells after the induction of differentiation (FIG. 34).

TABLE 3

| Type of media | Components | Content |
|---|---|---|
| Medium 1 | DMEM | |
| (ectoderm/astrocyte differentiation-inducing medium) | FBS | 1% |
| | N2 supplement | 1% |
| | Glutamax-I | 1% |
| Medium 2 | DMEM | |
| (mesoderm/myocardial cell differentiation-inducing medium) | FBS | 20% |
| | 2-Mercaptoethanol | |
| | Non-essential amino acids | 1% |
| | Penicillin/streptomycin | 1% |
| | Ascorbic acid | 100 μM |
| Medium 3 | DMEM | |
| (endoderm/nerve cell differentiation-inducing medium) | FBS | 20% |
| | 2-Mercaptoethanol | |
| | Non-essential amino acids | 1% |
| | Penicillin/streptomycin | 1% |

TABLE 4

| Gene names | Primer sequences (5' → 3') | |
|---|---|---|
| AFP | F GAATGCTGCAAACTGACCACGCTGGAAC | SEQ ID NO.: 27 |
| | R TGGCATTCAAGAGGGTTTTCAGTCTGGA | SEQ ID NO.: 28 |
| FOXA2 | F TGGGAGCGGTGAAGATGGAAGGGCAC | SEQ ID NO.: 29 |
| | R TCATGCCAGCGCCCACGTACGACGAC | SEQ ID NO.: 30 |
| Brachyury | F GCCCTCTCCCTCCCCTCCACGCACAG | SEQ ID NO.: 31 |
| | R CGGCGCCGTTGCTCACAGACCACAGG | SEQ ID NO.: 32 |
| MSX1 | F CGAGAGGACCCCGTGGATGCAGAG | SEQ ID NO.: 33 |

TABLE 4-continued

| Gene names | Primer sequences (5' → 3') | |
|---|---|---|
| | R GGCGGCCATCTTCAGCTTCTCCAG | SEQ ID NO.: 34 |
| ACTA2 (a-SMA) | F CTATGAGGGCTATGCCTTGCC | SEQ ID NO.: 35 |
| | R GCTCAGCAGTAGTAACGAAGGA | SEQ ID NO.: 36 |
| TnTc | F ATGAGCGGGAGAAGGAGCGGCAGAAC | SEQ ID NO.: 37 |
| | R TCAATGGCCAGCACCTTCCTCCTCTC | SEQ ID NO.: 38 |
| GATA4 | F CGACACCCCAATCTCGATATG | SEQ ID NO.: 39 |
| | R GTTGCACAGATAGTGACCCGT | SEQ ID NO.: 40 |
| NKX2.5 | F CCAAGGACCCTAGAGCCGAA | SEQ ID NO.: 41 |
| | R ATAGGCGGGTAGGCGTTAT | SEQ ID NO.: 42 |
| Nestin | F GAAACAGCCATAGAGGGCAAA | SEQ ID NO.: 43 |
| | R TGGTTTTCCAGAGTCTTCAGTGA | SEQ ID NO.: 44 |
| PAX6 | F ACCCATTATCCAGATGTGTTTGCCCGAG | SEQ ID NO.: 45 |
| | R ATGGTGAAGCTGGGCATAGGCGGCAG | SEQ ID NO.: 46 |
| Map2 | F CAGGTGGCGGACGTGTGAAAATTGAGAGTG | SEQ ID NO.: 47 |
| | R CACGCTGGATCTGCCTGGGGACTGTG | SEQ ID NO.: 48 |
| GFAP | F GGCCCGCCACTTGCAGGAGTACCAGG | SEQ ID NO.: 49 |
| | R CTTCTGCTCGGGCCCCTCATGAGACG | SEQ ID NO.: 50 |
| Sox1 | F TACAGCCCCATCTCCAACTC | SEQ ID NO.: 51 |
| | R GCTCCGACTTCACCAGAGAG | SEQ ID NO.: 52 |
| Chat | F GGAGGCGTGGAFCTCAGCGACACC | SEQ ID NO.: 53 |
| | R CGGGGAGCTCGCTGACGGAGTCTG | SEQ ID NO.: 54 |
| Aadc | F CGCCAGGATCCCCGCTTGAAATCTG | SEQ ID NO.: 55 |
| | R TCGGCCGCCAGCTCTTTGATGTGTTC | SEQ ID NO.: 56 |
| Dat | F ACAGAGGGGAGGTGCGCCAGTTCACG | SEQ ID NO.: 57 |
| | R ACGGGGTGGACCTCGCTGCACAGATC | SEQ ID NO.: 58 |
| Th | F CTGTGGCCTTTGAGGAGAAG | SEQ ID NO.: 59 |
| | R GGTGGATTTTGGCTTCAAAC | SEQ ID NO.: 60 |
| Tuj 1 | F GAGCGGATCAGCGTCTACTACAA | SEQ ID NO.: 61 |
| | R GATACTCCTCACGCACCTTGCT | SEQ ID NO.: 62 |
| Vglut1 | F CGACGACAGCCTTTTGTGGT | SEQ ID NO.: 63 |
| | R GCCGAGACGTAGAAAACAGAG | SEQ ID NO.: 64 |
| Vmat2 | F CTTTGGAGTTGGTTTTGC | SEQ ID NO.: 65 |
| | R GAGTTGTGGTCCATGAG | SEQ ID NO.: 66 |

Figure 35:
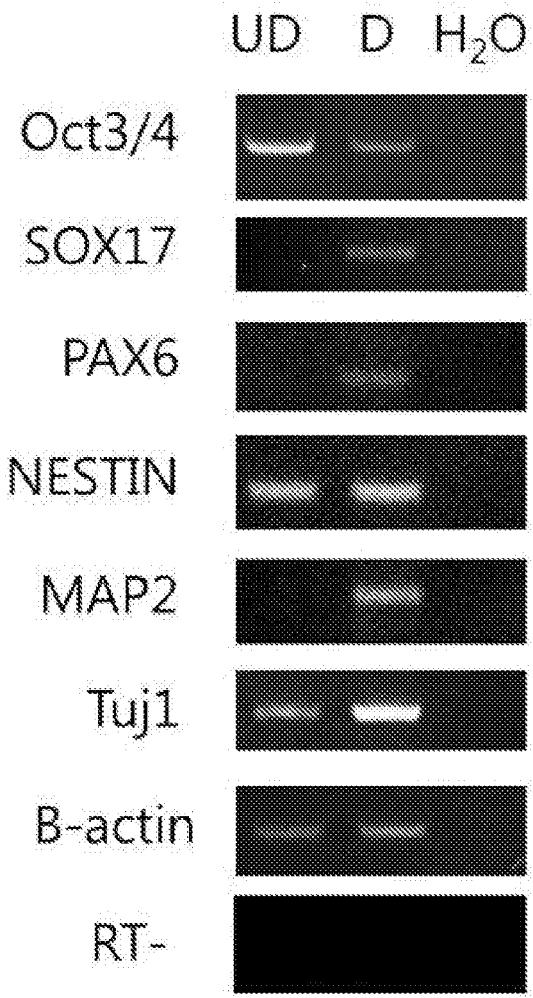
FIG. 35 shows RT-PCR analysis results of expression of neuronal lineage genes to check in vitro differentiation of the human Physics cells.
Figure 36:
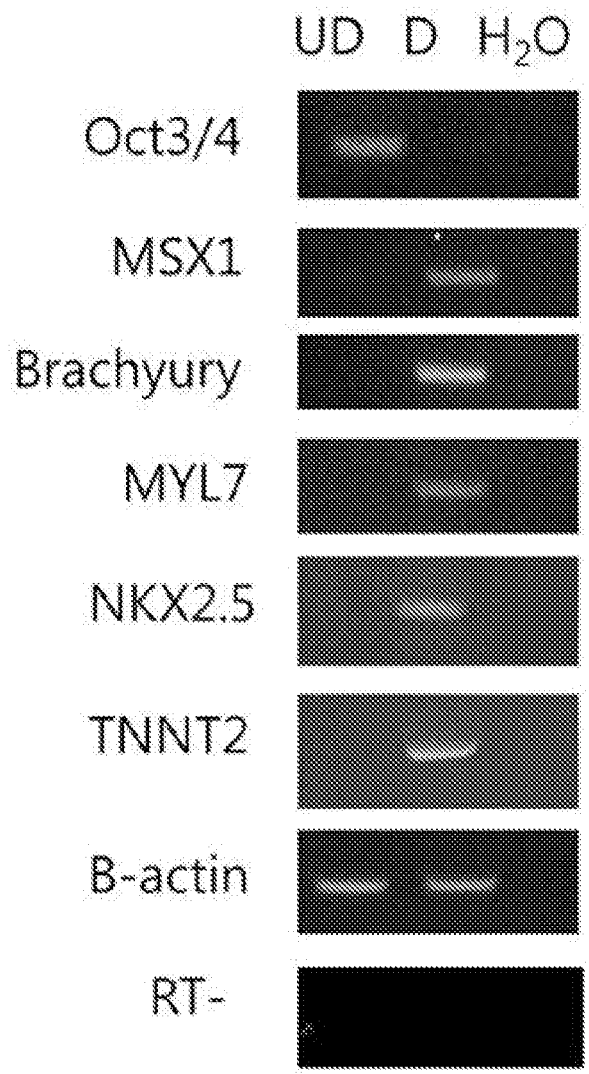
FIG. 36 shows RT-PCR analysis results of expression of cardiac lineage genes to check in vitro differentiation of the human Physics cells.

As shown in FIGS. 35 and 36, the expression of SRY-box including gene gene 17 (SOX17; the endoderm), paired box 6 (PAX6; the ectoderm), Nestin (a nerve cell marker), microtubule-associated protein 2 (MAP2; the ectoderm), class III beta-tubulin (TuJ1; a nerve cell marker), msh homeobox 1 (MSX1; the mesoderm), Brachyury (the mesoderm), myosin light chain 7 (MYL7; myocardial cells), NK2 homeobox 5 (NKX2.5; myocardial cells), and Troponin T type 2 (TnnT2; myocardial cells) was observed during a differentiation time of 1 to 2 weeks using RT-PCR.

In particular, the expression of OCT3/4 was significantly reduced after the induction of differentiation.

The differentiation into nerve cells or cardiac cells was also confirmed through immunocytochemistry.

Figure 37:
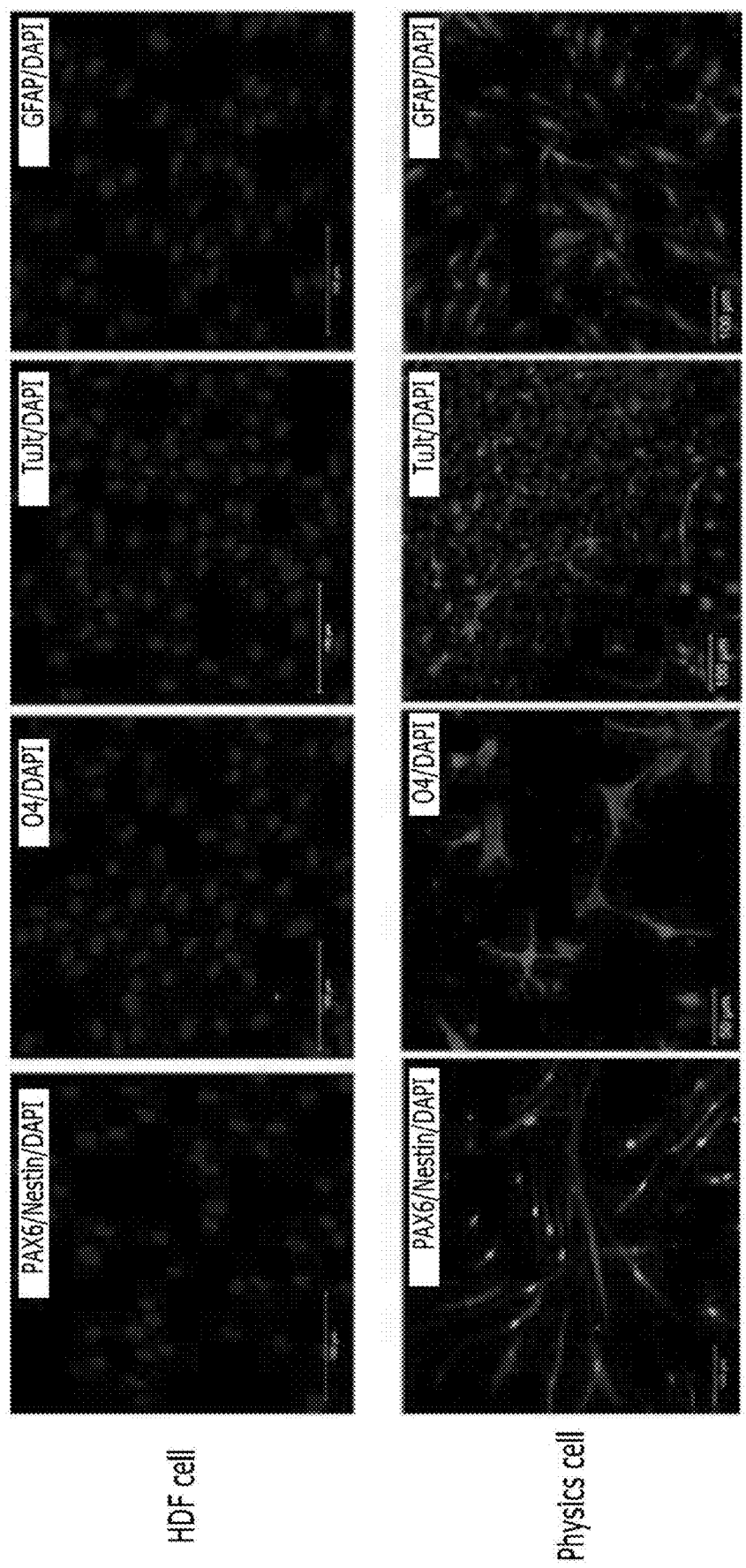
FIG. 37 shows immunocytochemical results of expression of a neuronal lineage marker to check in vitro differentiation of the human Physics cells.
Figure 38:
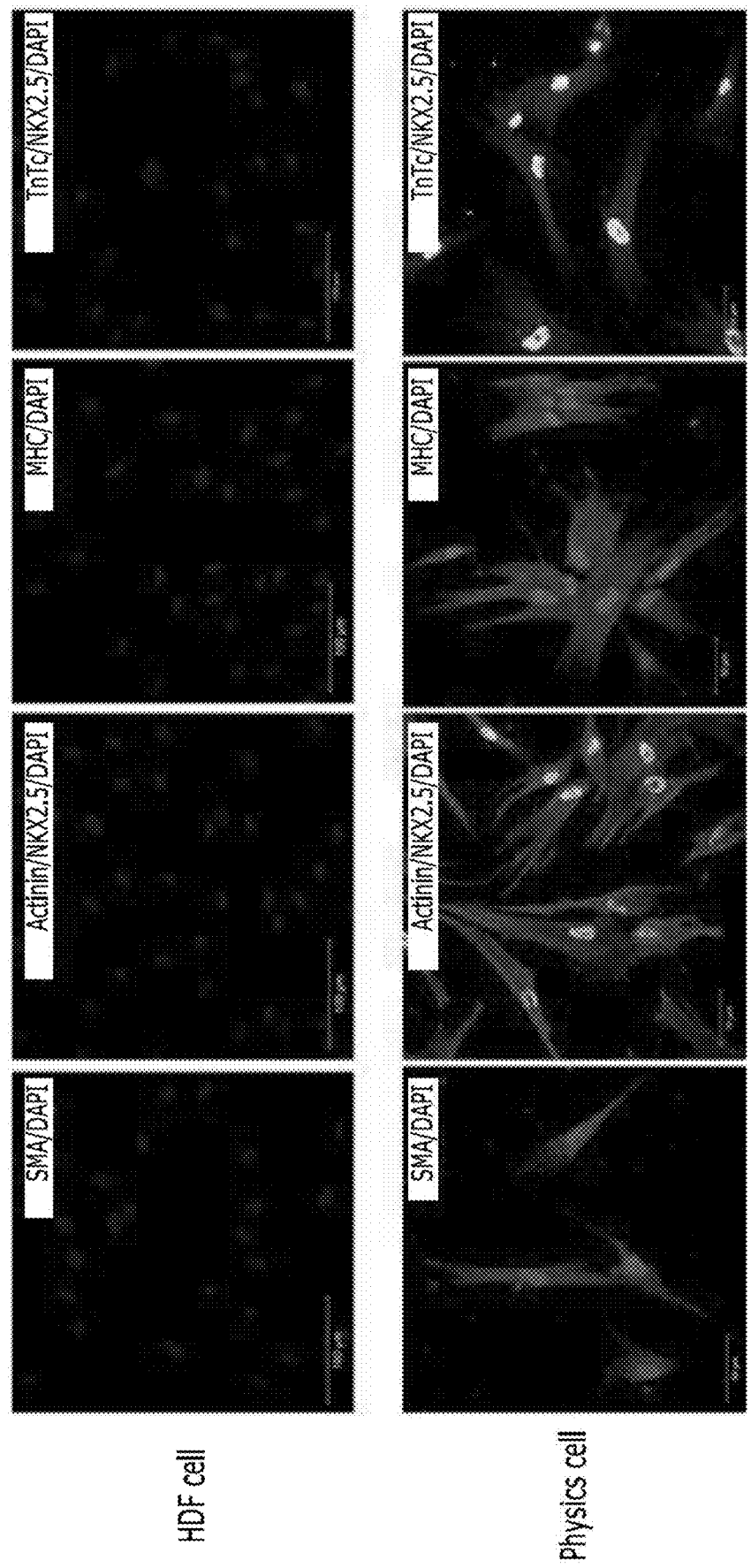
FIG. 38 shows immunocytochemical results of expression of a cardiac lineage marker to check in vitro differentiation of the human Physics cells.
Figure 39:
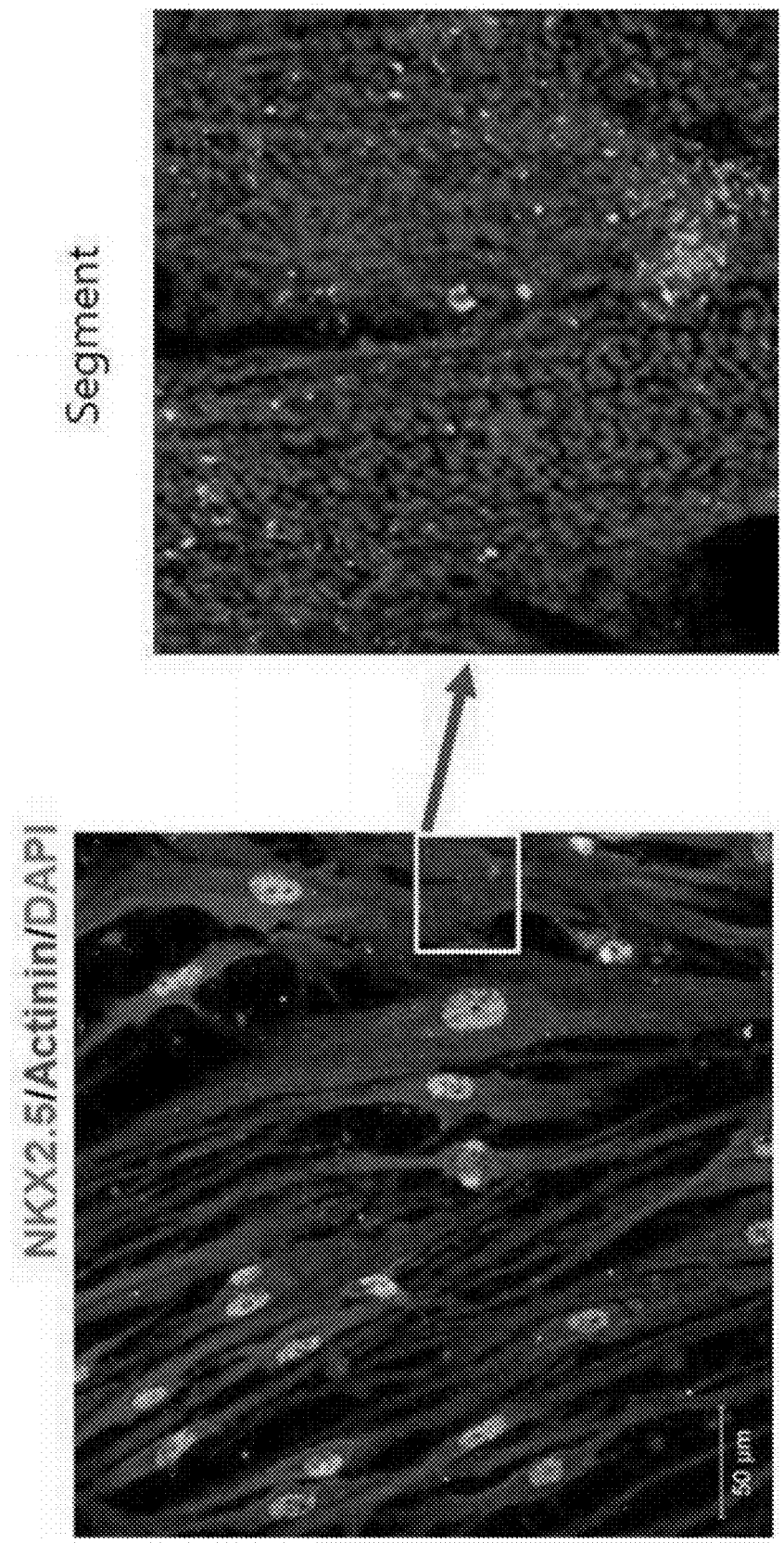
FIG. 39 is an immunocytochemical image of actinin.

As shown in FIGS. 37 to 39, the neural progenitor cell markers (PAX6 and Nestin) were observed in the Physics cells grown in an astrocyte medium. When additional differentiation of these differentiated Physics cells was induced for 2 weeks after the astrocyte medium was replaced with an oligodendrocyte medium or a neuronal medium, the expression of each of the oligodendrocyte markers (MAP2 and O4) or the neuronal markers (MAP2 and Tuj1) was observed. A differentiation time of 2 weeks was sufficient to detect the cardiac markers including MHC, SMA, Actinin, NKX2.5 and TnTc. In particular, a typical segmented actin pattern was detected in actinin. However, no neural or cardiac markers were expressed in the HDFs under the same culture conditions.

<Example 5> Stability Test

Figure 40:
FIG. 40 shows karyotyping analysis results of the human Physics cells of the present invention.

The ultrasound did not cause undesirable side-effects such as mutagenesis, genetic modifications, cancer generation, etc. The Physics cells had a normal karyotype (FIG. 40).

<Example 6> Evaluation of In Vivo Differentiation Capacity of Physics Cells

To evaluate the in vivo differentiation capacity of the Physics cells, $1 \times 10^6$ cells of the Physics cells cultured for 5 days were injected into testes and thigh muscles of 4- to 5-week-old immune-deficient mice (NOD/SCID mice), and raised for 4 weeks. Thereafter, the testes and muscles were recovered, fixed with 4% paraformaldehyde, and then cryosectioned to locate the injected cells through human nuclear antigen staining. Then, a variety of proliferation- and differentiation-associated protein markers (Ki67, CD44, and SMA) were stained to determine whether the injected cells had differentiated.

Figure 41:
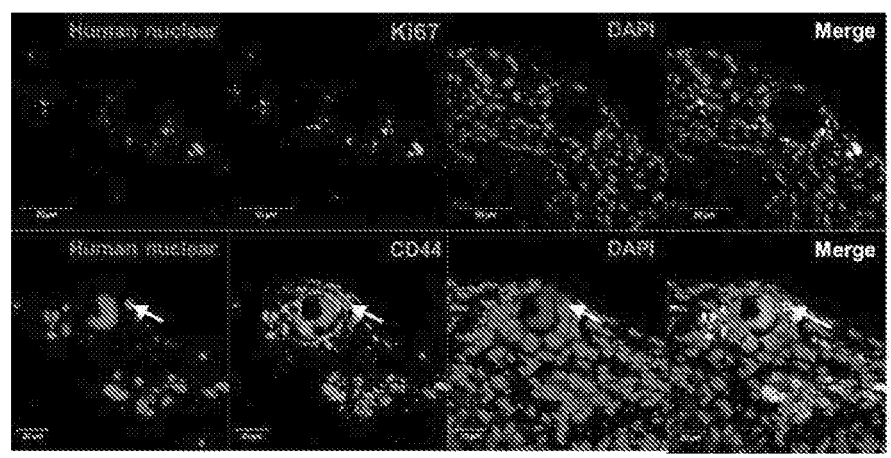
FIG. 41 shows fluorescent immunohistological staining results for determining in vivo differentiation of the human Physics cells in a mouse testis.

As shown in FIG. 41, it was confirmed that the Physics cells injected into the testes were observed in vascular endothelial cells in the testes after 4 weeks, and the Physics cells continued to proliferate, through Ki67 staining. Also, it was confirmed that CD44, which is a vascular endothelial marker, was stained, as observed in the cells indicated by arrows.

Figure 42:
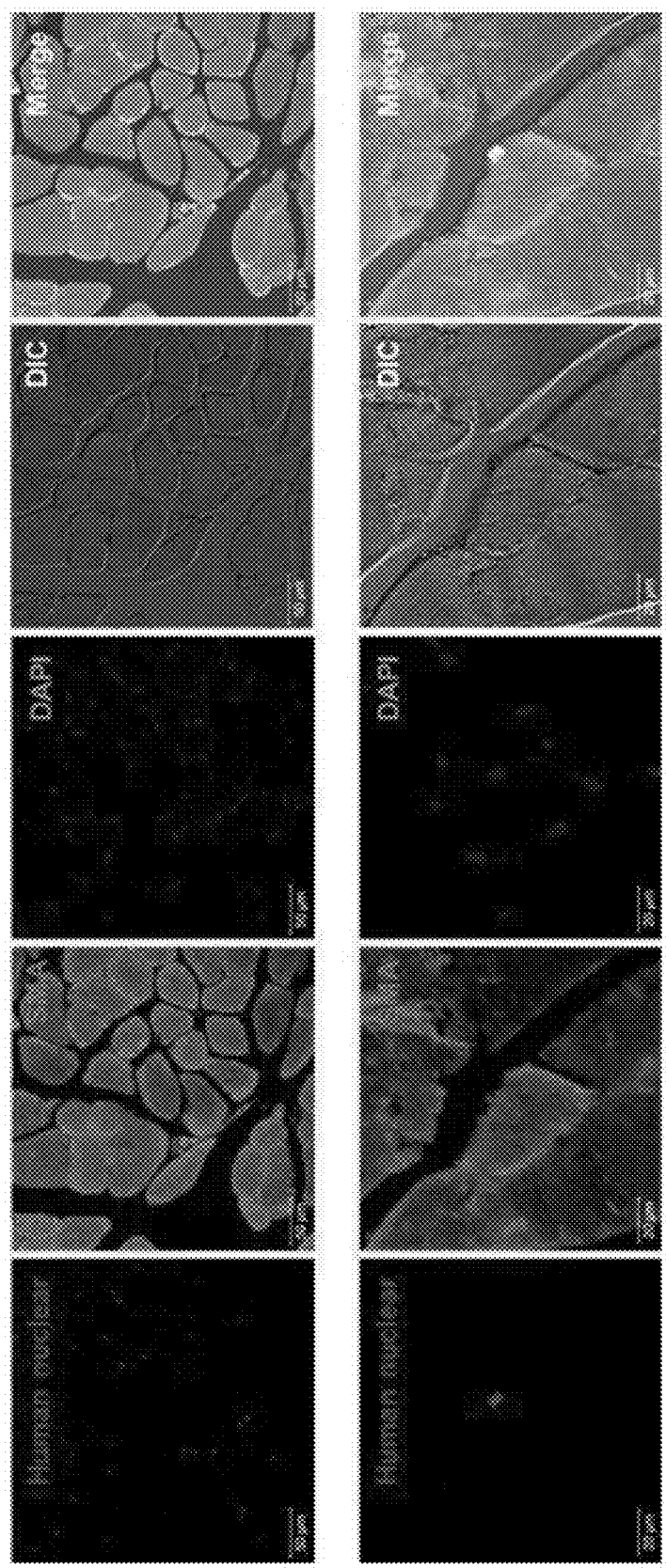
FIG. 42 shows fluorescent immunohistological staining results of the human Physics cells to check in vivo differentiation of muscle in mouse thighs.

It was confirmed that the cells injected into the mouse thighs were found in a laminar layer outside a fibromuscular layer, and SMA, which is a muscle protein marker, was stained (FIG. 42). Such results suggested that the Physics cells injected into the bodies differentiated in response to the surrounding cells and environments.

<Example 7> Effect of Cell Culture Medium

To generate Physics cells, a human ES cell culture medium was used. The ES cell culture medium was developed as a defined medium for maintaining and proliferating ES cells in an undifferentiated state. To examine an effect of the cell culture medium, a normal HDF culture medium was used to generate Physics cells.

Figure 43:
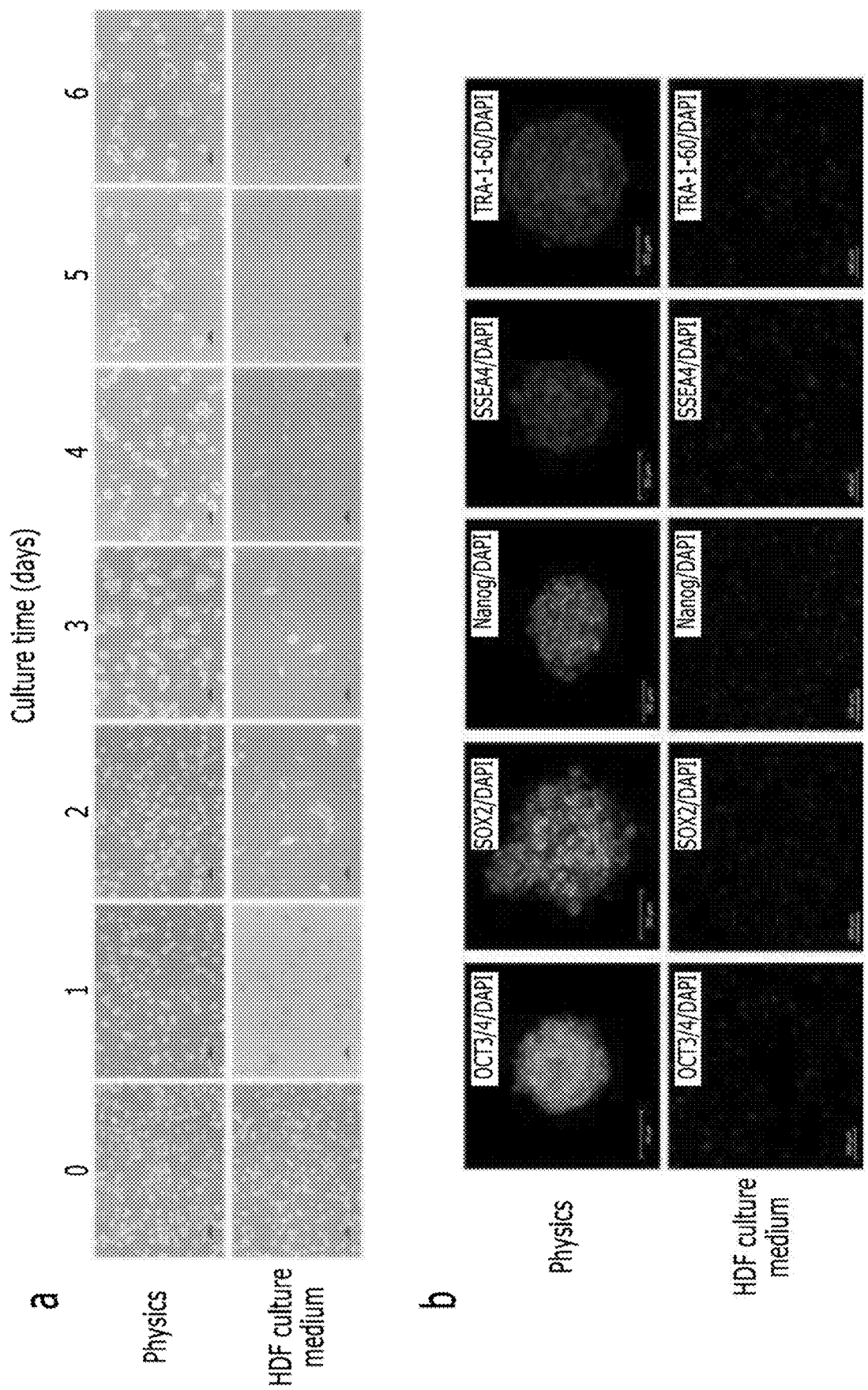
FIG. 43 shows an effect of cell culture media: a) shows results using an ES medium and an HDF culture medium, and b) shows results of inducing the human Physics cells in the ES medium and the HDF culture medium and determining the presence of an ES marker.

As shown in FIGS. 43A and 43B, the shape and spheroid-forming efficiency of the HDF culture medium ware quite different from those of the ES cell culture medium. On the first day after the Physics cells were seeded in an ultrasound-treated HDF medium, a small amount of multicellular spheroids were formed. However, most of the spheroids were attached to a surface of a dish after 2 days. On day 4 of culture, all the spheroids were attached to the surface of the dish to grow into typical fibroblast cells. Immunocytochemical results also showed that different gene expression patterns appeared between the two different culture medium conditions. The typical Physics cells formed using the ES cell culture medium showed a high expression level of OCT3/4, SOX2, NANOG, SSEA-4, and TRA-1-60. A DMEM medium had no effect on induction of expression of the undifferentiated marker genes and three germ layer marker genes. These results suggest that the formation of the spheroids and the expression of the specific marker genes were closely associated with the components of the cell culture medium.

<Example 8> Effect of Cell Line

To evaluate whether a method of generating the Physics cells was applicable to other cell lines and to clinical applications in the future, generation of the Physics cells were examined using other cell lines such as HeLa cells, L132 human pulmonary epithelial cells and patient-derived dermal fibroblast cells.

Figure 44A:
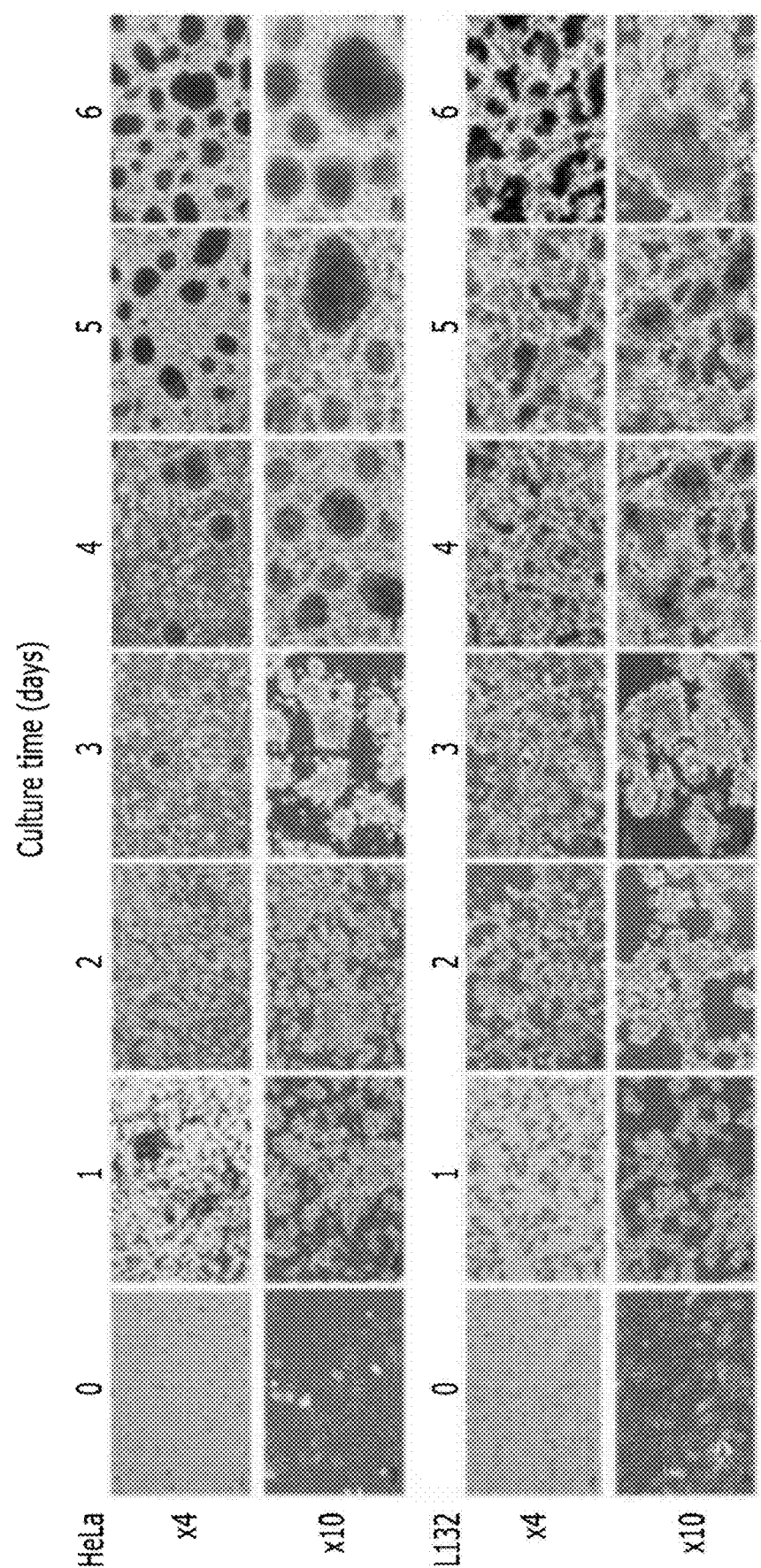
FIG. 44 shows results of inducing the human Physics cells from other cell lines: a) shows morphological changes of the cells, b) and c) shows results of inducing the human Physics cells from the other cell lines and determining the presence of b) an ES marker and c) a three germ layer marker.
Figure 44B:
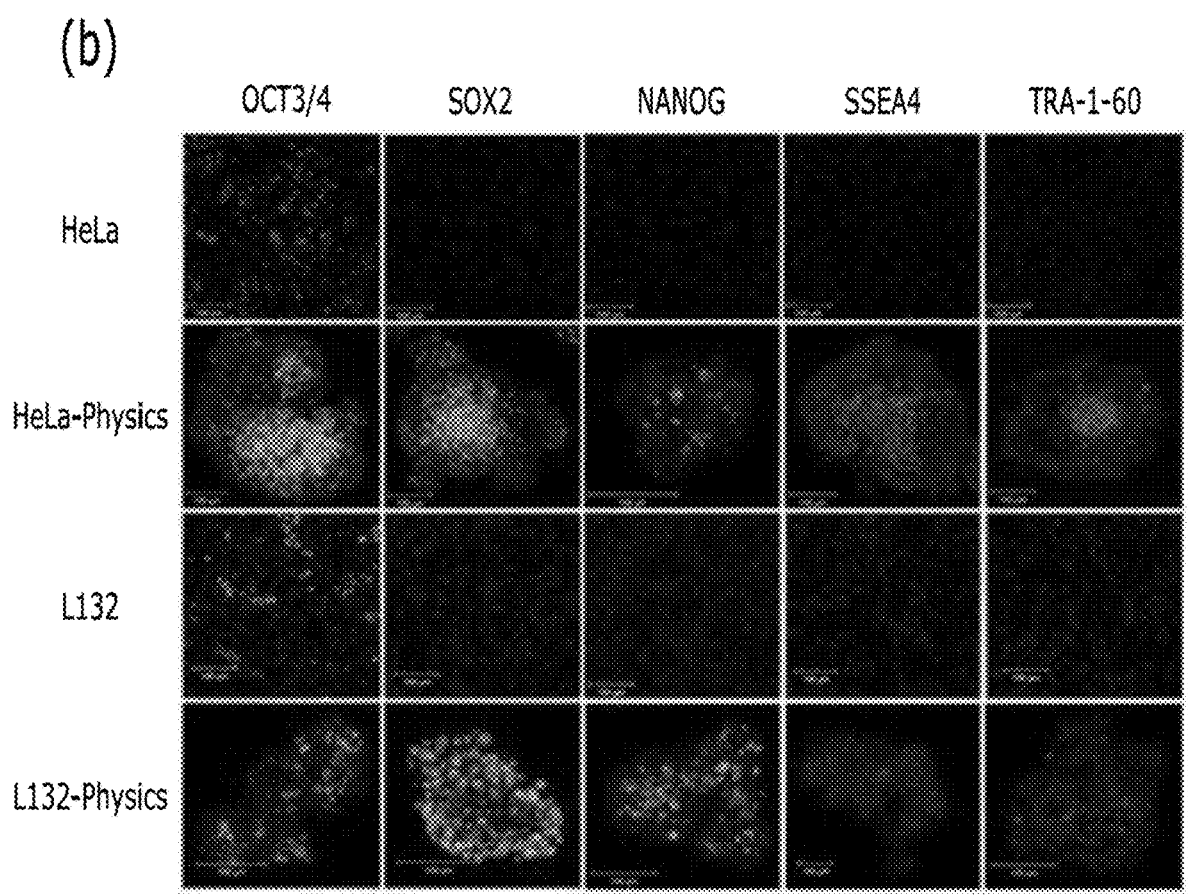
Figure 44C:
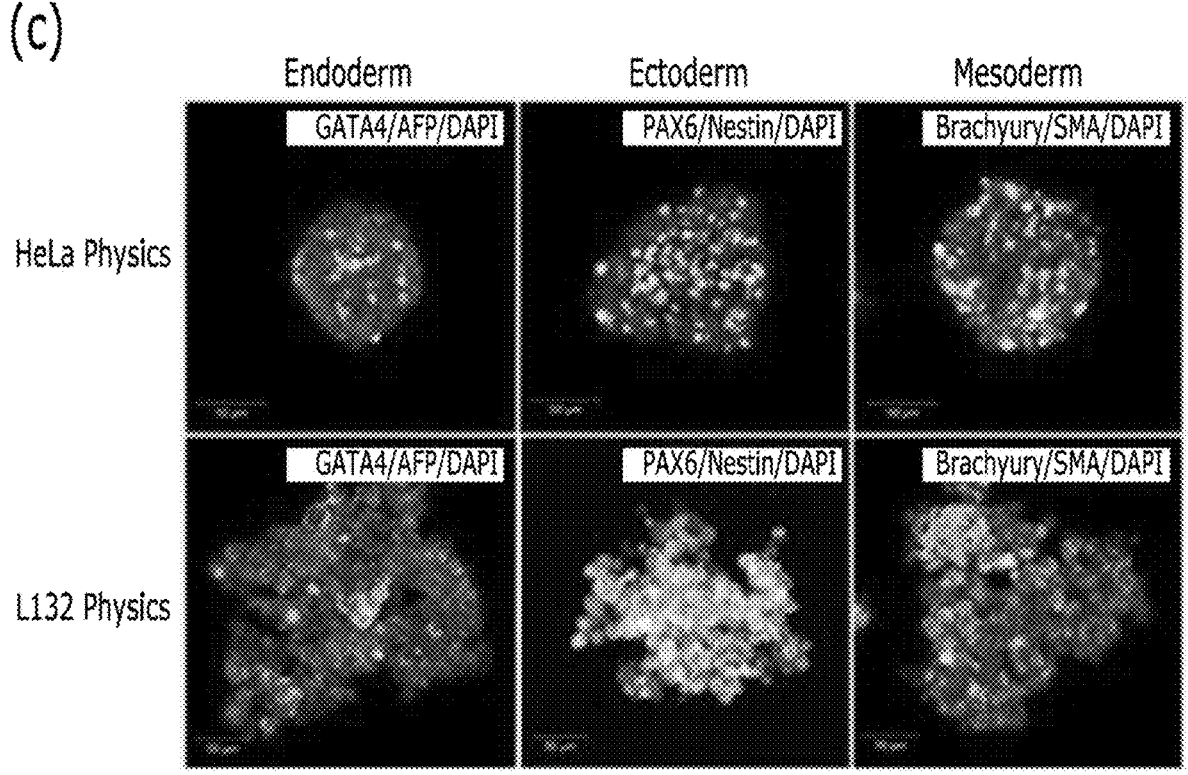

As shown in FIGS. 44A to 44C, when two cell lines were directly exposed to ultrasound and then cultured in an ultrasound-treated ES cell culture medium in a Petri dish for bacterial culture, the multicellular spheroids were formed. Interestingly, the novel Physics cells formed from the two cell lines had quite different shape and size distributions, compared to the Physics cells formed from the HDFs. The size distribution of the HeLa cell-derived Physics cells had no significant consistency and a very large size. The L132 cell-derived Physics cells had a more complicated aggregate shape. The respective spheroids were further fused to form a panel-like structure.

As shown in FIGS. 44B and 44C, the expression of the pluripotent marker including OCT3/4, SOX2, NANOG, SSEA4, and TRA-1-60 and the three germ layer marker genes including GATA4, AFP, PAX6, Nestin, Brachyury, and SMA in two types of different Physics cells were confirmed through immunocytochemistry.

Figure 45:
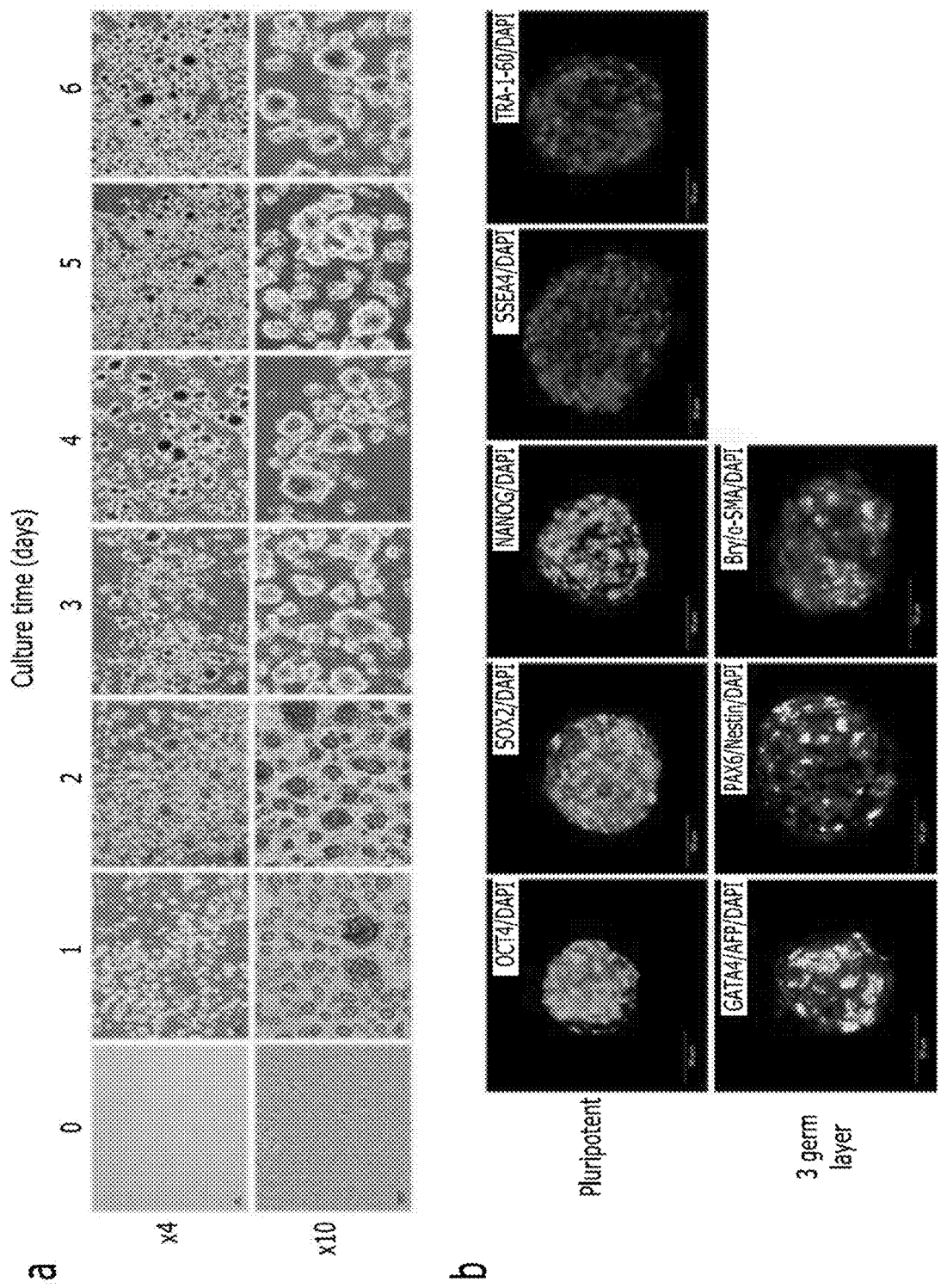
FIG. 45 shows results of inducing the human Physics cells from patient skin cells: a) shows morphological changes of the cells, and b) shows results of inducing the human Physics cells from the other cell lines and determining the presence of the ES marker and the three germ layer marker.

Also, the experimental results using patient skin cells also showed that the spheroids were formed like the Physics cells, and the expression of the pluripotent markers and the three germ layer markers were confirmed through immunocytochemistry (FIG. 45).

These results strongly prove that the ultrasound stimulation inducing the generation of the Physics cells was applicable to various cell lines, and showed the possibility of autologous cell therapy using patient cells.

<Example 9> Effect of Different Physical Stimuli

Additional external stimuli were applied to HDF and ES cell culture media to confirm and evaluate a mechanism of generating the Physics cells.

It was determined whether the Physics cells were formed through laser treatment instead of the ultrasound treatment. For this purpose, the same human dermal fibroblast cells as used for the ultrasound treatment were used, and laser treatment conditions were as follows: cells were irradiated with 808 nm laser beams for 5 seconds using a laser (Ndlux) for OCLA treatment, and then cultured.

For heat treatment, dermal fibroblast cells were exposed to 42° C. for 2 minutes, and then kept on ice for approximately 5 seconds.

Figure 46:
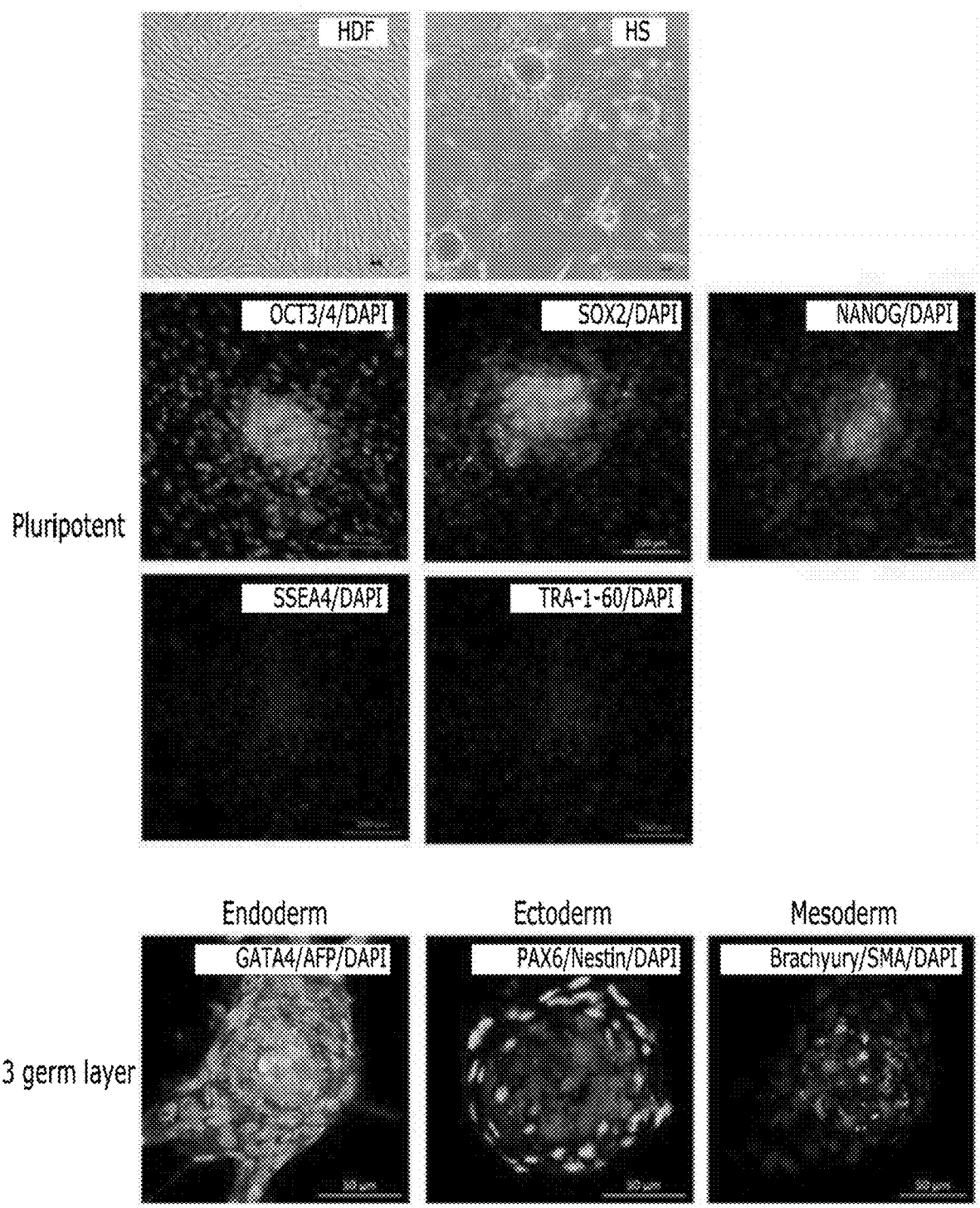
FIG. 46 shows results of inducing the human Physics cells using heat treatment as another energy source and determining the presence of the ES marker and the three germ layer markers.
Figure 47:
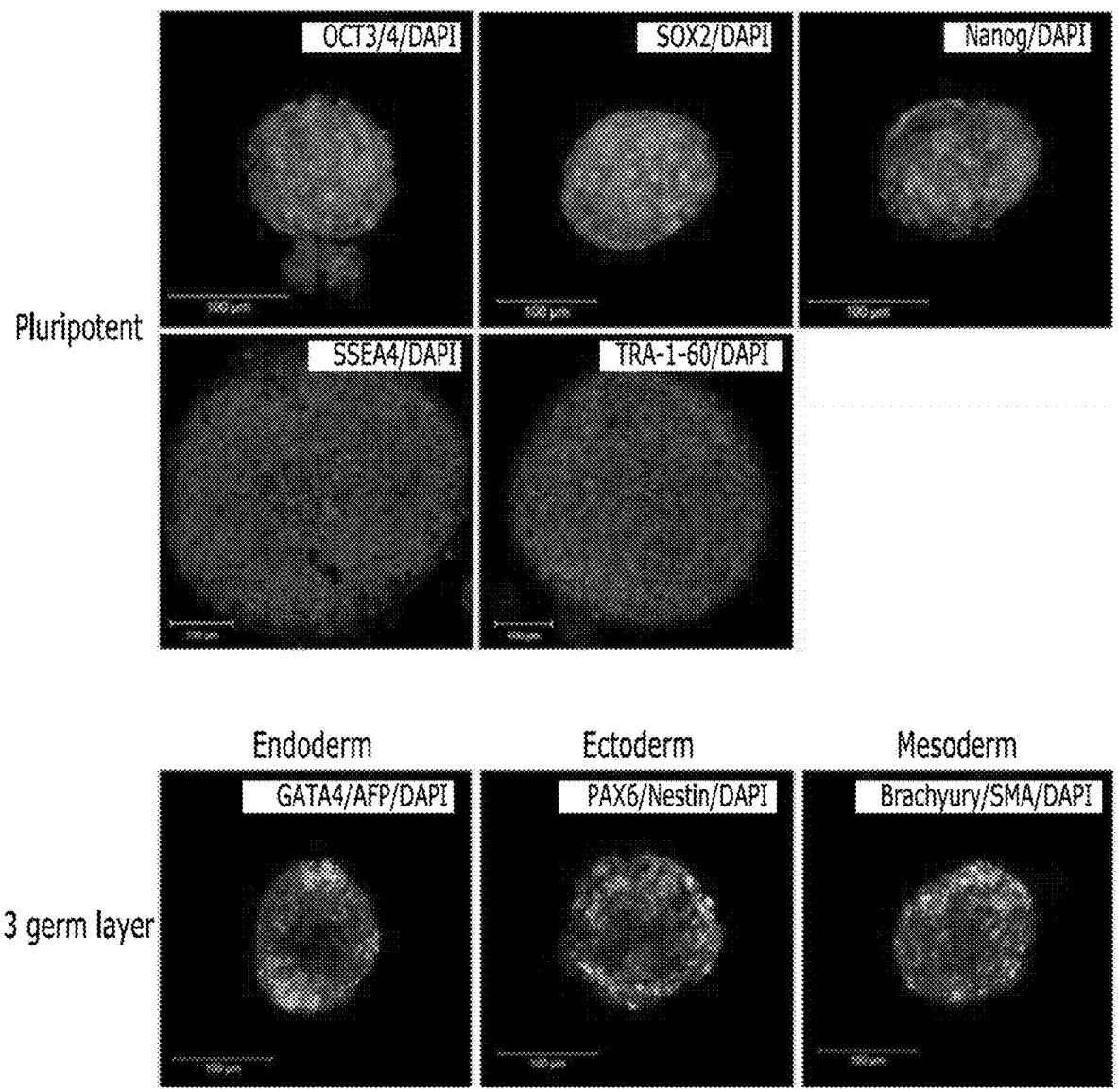
FIG. 47 shows results of inducing the human Physics cells using a laser as still another energy source and determining the presence of the ES marker and the three germ layer marker.

As shown in FIGS. 46 and 47, the multicellular spheroids were successfully formed after both of the HDF and ES cell culture media were subjected to the laser or heat treatment. The laser-treated HDFs also formed multicellular spheroids immediately after laser induction. Although the spheroids had an irregular shape and a non-uniform size distribution, it was observed that the pluripotent markers and three germ layer markers were expressed at a high level. The heat treatment also induced the spheroid formation. However, the efficiency of the heat treatment was lower than those of the ultrasound and laser treatment. At least half of the multicellular spheroids induced by heat were attached to a surface of the dish for 8 days of maintenance. Despite the lower spheroid-forming efficiency, high expression levels of the pluripotent markers and three germ layer markers were observed. These results strongly prove that the generation of the Physics cells is closely associated with physical stimuli.

<Example 10> Generation of Mouse Physics Cells

Figure 48:
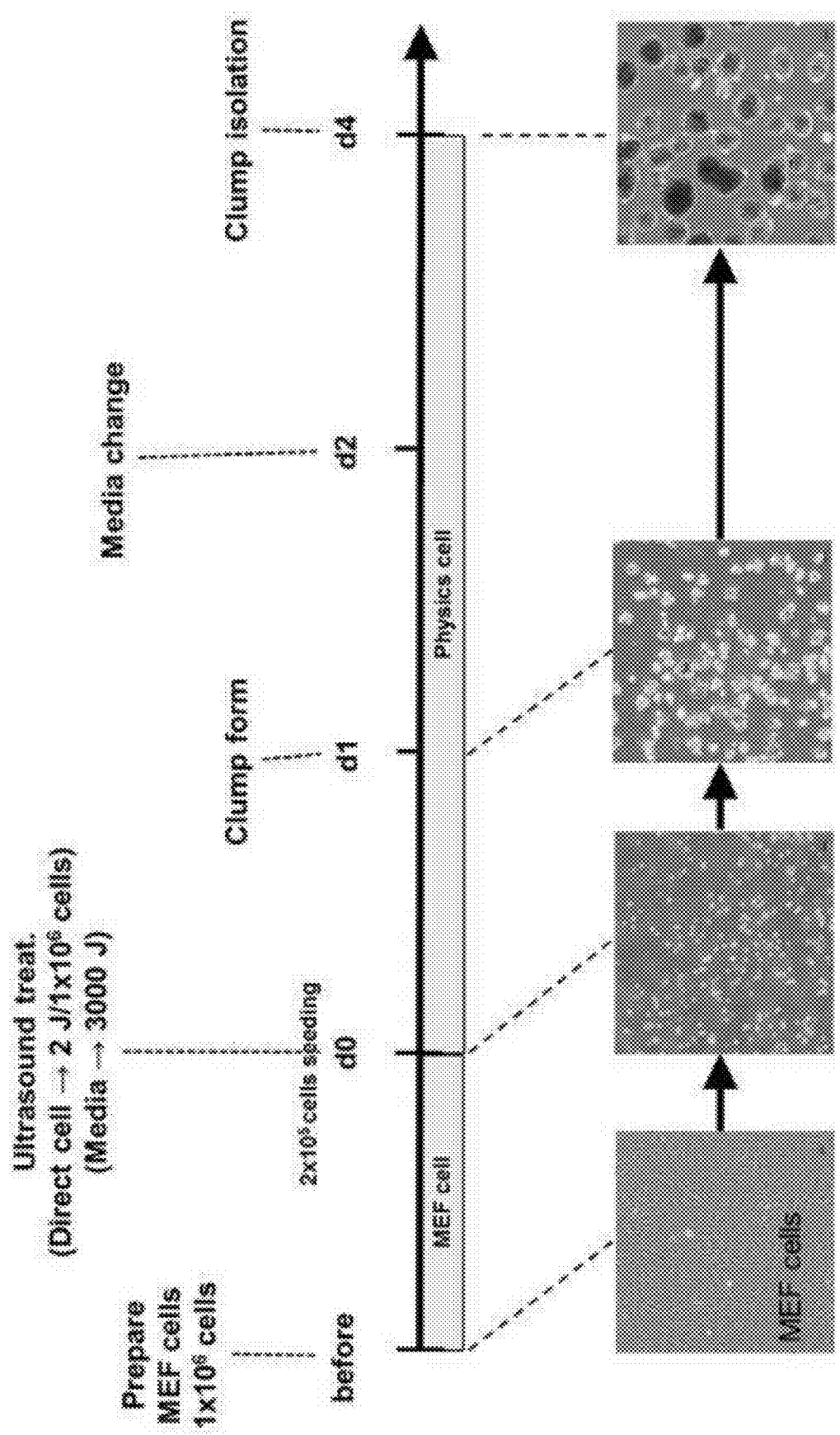
FIG. 48 shows a process of inducing the mouse Physics cells from mouse embryonic fibroblast cells.

Mouse Physics cells were prepared according to a method shown in FIG. 48. For this purpose, OG2 mouse embryonic fibroblast (MEF) were mixed with an ES cell culture medium which had been treated with 20 KHz ultrasound at an intensity of 5 W/cm$^2$ for 10 minutes. Thereafter, the cells were directly treated with ultrasound at an intensity of 1 W/cm$^2$ for 5 seconds, and then cultured. The cultured cells were observed at intervals of 1, 3, 5, 8 and 10 days under a fluorescence microscope to determine a morphological change of the cells and fluorescent GFP expression. The compositions of the media for ultrasound treatment are as listed in Table 1.

The MEF cells were embryonic fibroblasts of 13.5-day old mice transformed with a GFP gene into which an OCT4 promoter was inserted and typically did not express OCT4. However, when OCT4 was expressed, GFP was also expressed, thereby producing green fluorescence.

Figure 49:
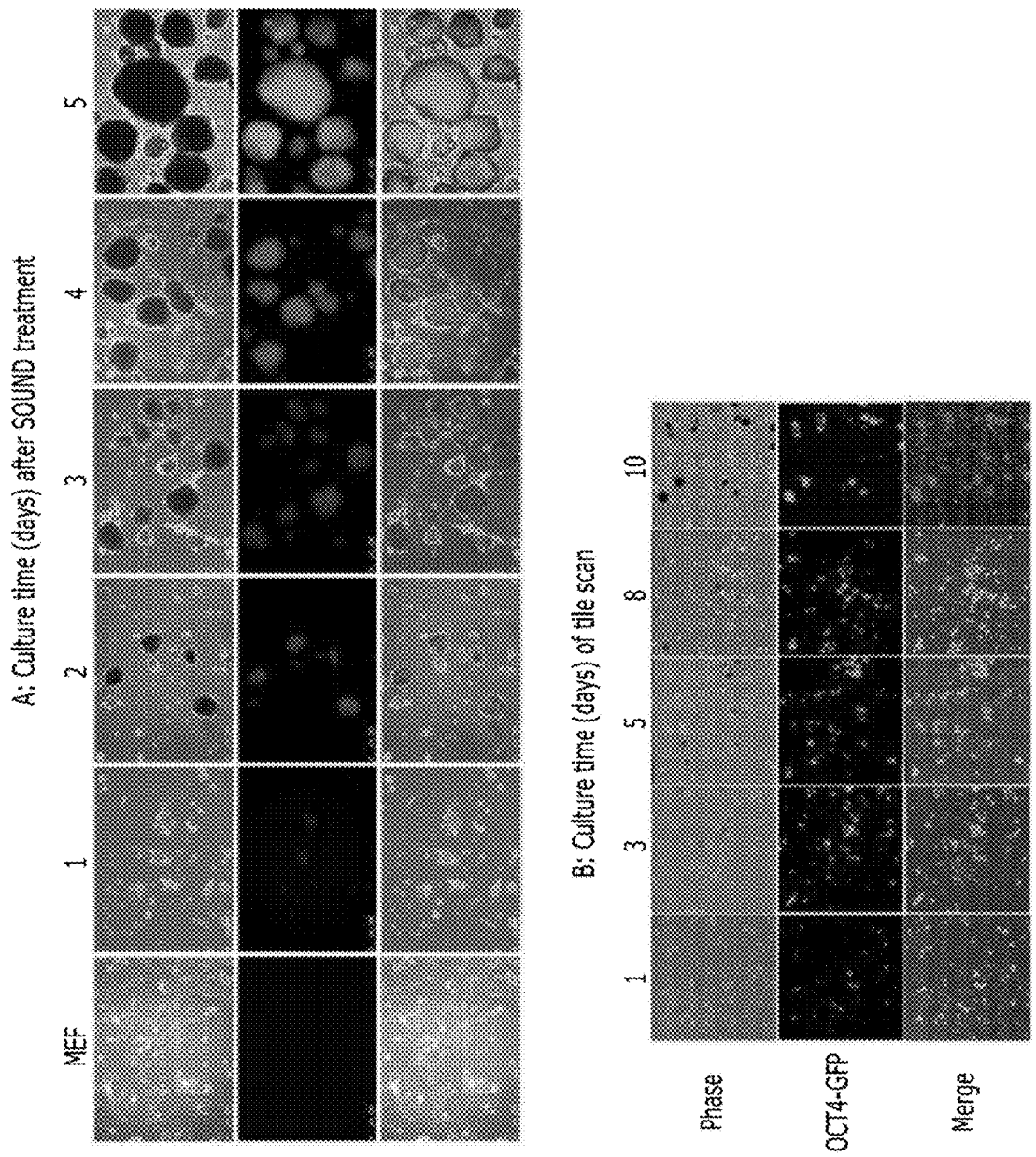
FIG. 49 shows results of determining morphological changes of and expression of Oct4 of transformed mouse embryonic fibroblast cells (OG2 MEF cells) in different culture time after ultrasound treatment: A shows results of determining GFP expression in mouse Physics spheroids, and B is a diagram of images merged as Tile scan images after multiple pictures were taken over a wide range.

As shown in FIG. 49A, the control did not produce green fluorescence in images of the OG2 MEF cells (OCT4 was not expressed). However, it can be seen that the size of cell spheres increased and the green fluorescence intensity increased as culture time passed in the case of OG2 MEFs treated with ultrasound. This indicates that the ultrasound treatment induced the OCT4 expression, and OCT4 had important characteristics of undifferentiated stem cells, indicating that the OG2 MEF cells reprogrammed into stem cells due to the ultrasound treatment.

Figure 50:
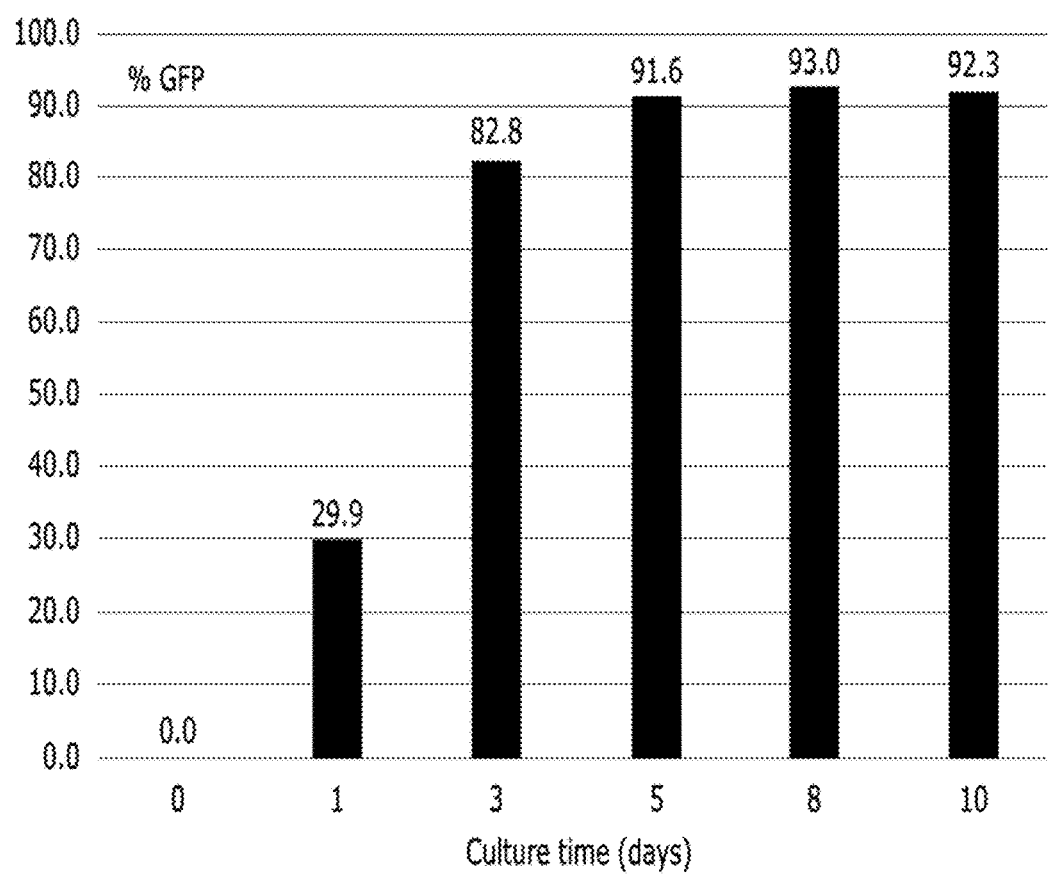
FIG. 50 is a graph plotted for a GFP expression rate of spheroids formed by ultrasound treatment, and a diagram showing results of analyzing a GFP expression rate in the entire ultrasound-treated cells using flow cytometry.
Figure 50:
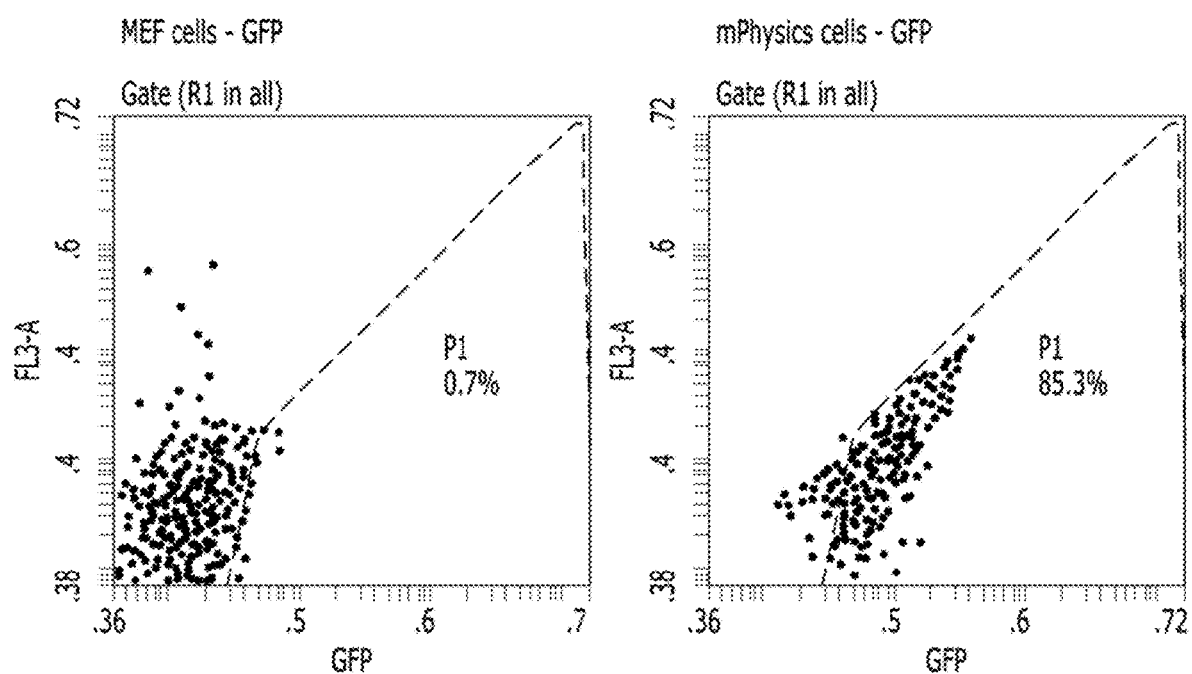
Figure 51:
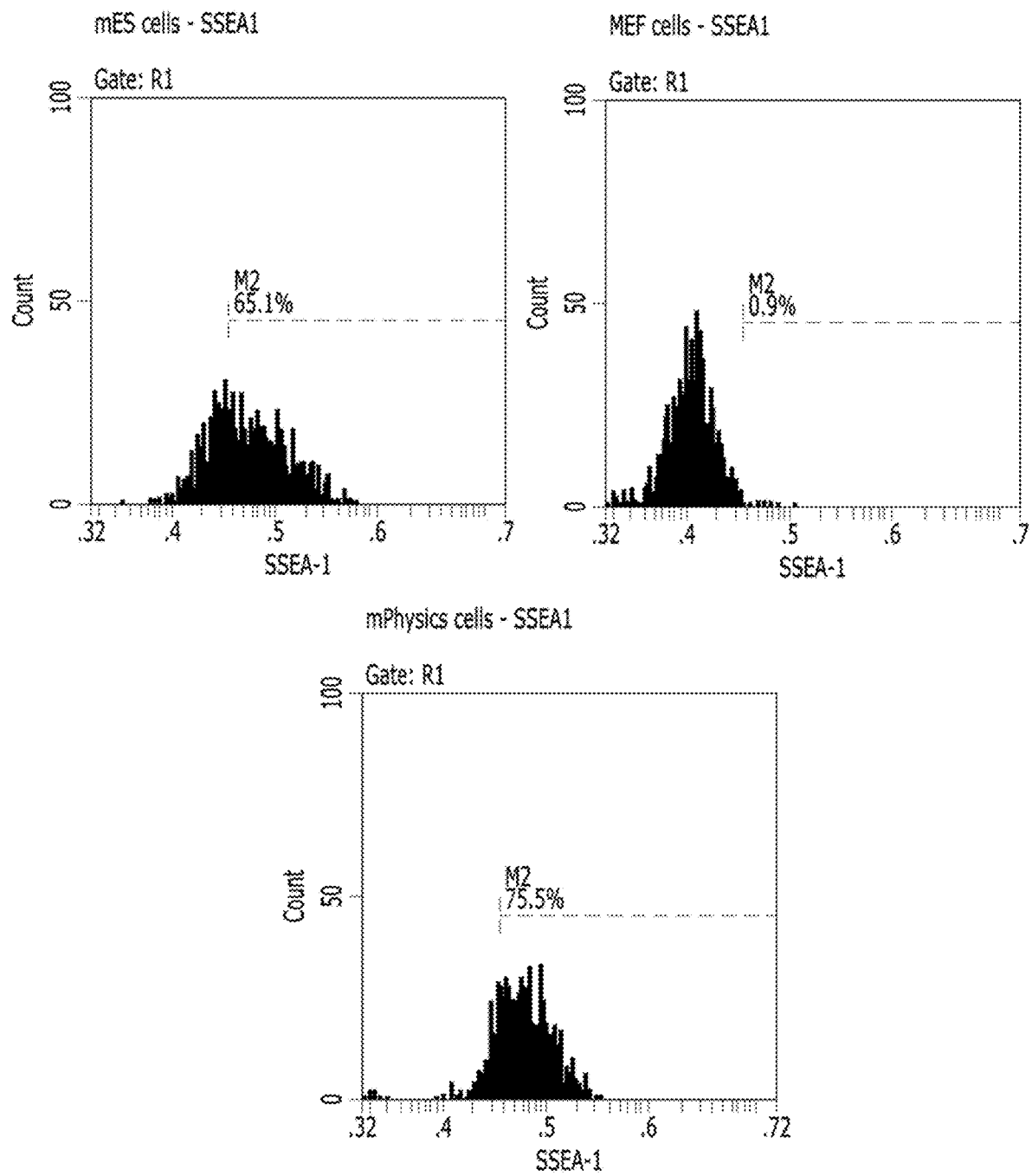
FIG. 51 shows results of analyzing expression of an undifferentiated cell surface marker (SSEA1) in the mouse Physics cells using flow cytometry.

FIG. 49B is a diagram of images merged as Tile scan images after multiple pictures were taken over a wide range, which shows an effect of ultrasound treatment. A large number of MEF cells reprogrammed due to the ultrasound treatment to express OCT4-GFP. The GFP expression efficiency of the spheroids formed as shown in FIG. 50 was analyzed. As a result, it was revealed that the spheroids had it was revealed that GFP was expressed in approximately 85.3% of the cells when the GFP expression in the whole cells was confirmed using flow cytometry. Further, it was revealed that SSEA1, which is an undifferentiated protein marker on the cell surface, was expressed in approximately 75.5% of the cells even when the SSEA1 expression was confirmed (FIG. 51). Such results suggest that the reprogramming efficiency was significantly increased due to the ultrasound treatment.

Next, the expression of the undifferentiated marker genes and protein markers (OCT4, SOX2, NANOG, and SSEA1) of the representative mouse embryonic stem cells (ESCs) was confirmed by RT-PCR and an immunocytochemical method using sets of primers as listed in the following Table 5.

Figure 52:
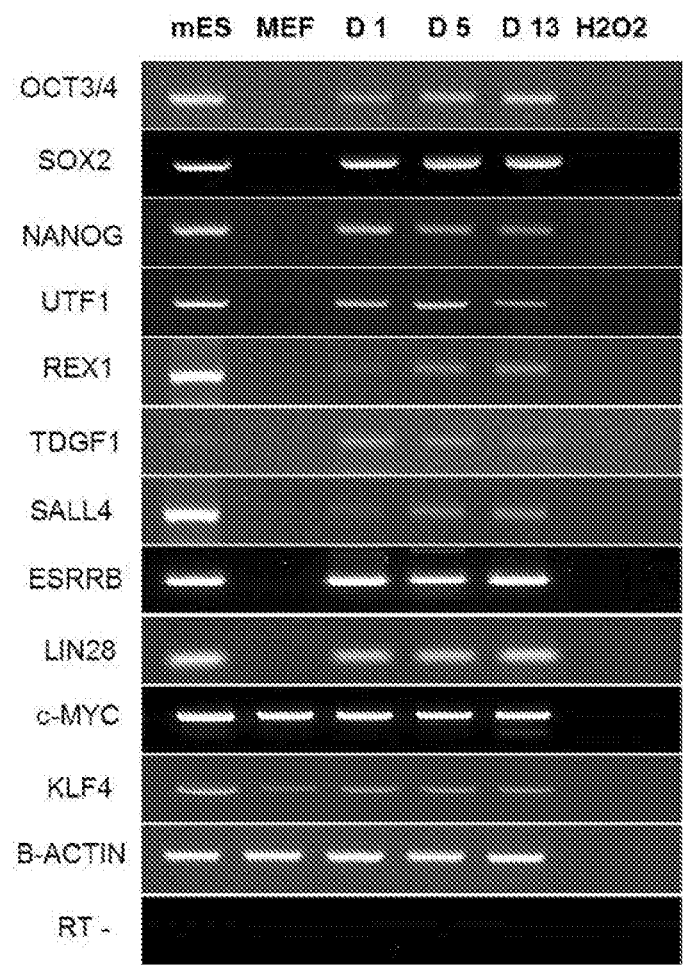
FIG. 52 shows RT-PCR analysis results of the pluripotent marker genes in the mouse Physics cells.
Figure 53:
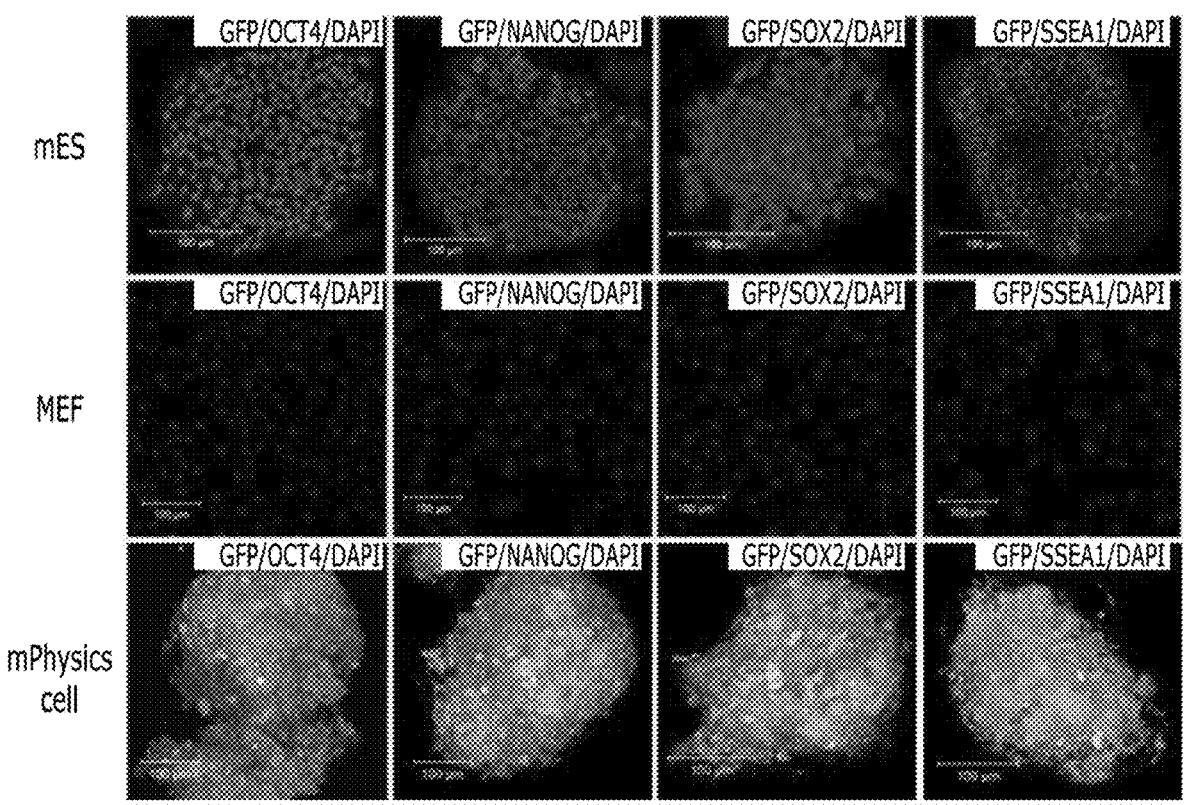
FIG. 53 shows results of analyzing the pluripotent protein markers in the mouse Physics cells.

As shown in FIGS. 52 and 53, it was confirmed that the undifferentiated markers were expressed in the mouse Physics cells.

Figure 54:
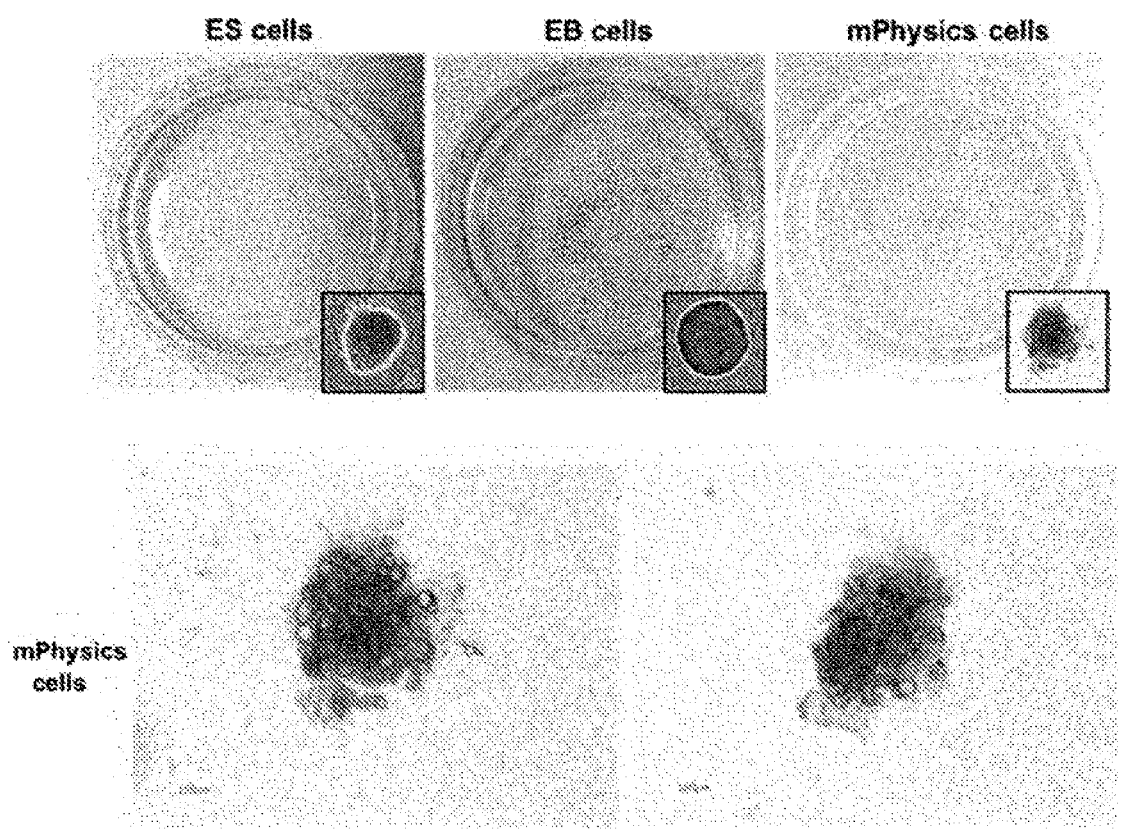
FIG. 54 shows alkaline phosphatase staining results for characterizing a pluripotent state of the mouse Physics cells.

Also, it was revealed that the undifferentiated markers were expressed through alkaline phosphatase staining (FIG. 54).

TABLE 5

RT-PCR primers used to check expression of undifferentiated markers in mouse ES

| Gene names | Primer sequences (5' → 3') | |
|---|---|---|
| Oct3/4 | F CTGAGGGCCAGGCAGGAGCACGAG | SEQ ID NO.: 67 |
| | R CTGTAGGGAGGGCTTCGGGCACTT | SEQ ID NO.: 68 |
| Sox2 | F TAGAGCTAGACTCCGGGCGATGA | SEQ ID NO.: 69 |
| | R TTGCCTTAAACAAGACCACGAAA | SEQ ID NO.: 70 |
| Nanog | F CAGGTGTTTGAGGGTAGCTC | SEQ ID NO.: 71 |
| | R CGGTTCATCATGGTACAGTC | SEQ ID NO.: 72 |
| c-Myc | F TGACCTAACTCGAGGAGGAGCTGGAATC | SEQ ID NO.: 73 |
| | R AAGTTTGAGGCAGTTAAAATTATGGCT-GAAGC | SEQ ID NO.: 74 |
| Klf4 | F GCGAACTCACACAGGCGAGAAACC | SEQ ID NO.: 75 |
| | R TCGCTTCCTCTTCCTCCGACACA | SEQ ID NO.: 76 |
| Esg1 | F GAAGTCTGGTTCCTTGGCAGGATG | SEQ ID NO.: 77 |
| | R ACTCGATACACTGGCCTAGC | SEQ ID NO.: 78 |
| Rex1 | F ACGAGTGGCAGTTTCTTCTTGGGA | SEQ ID NO.: 79 |
| | R TATGACTCACTTCCAGGGGCACT | SEQ ID NO.: 80 |
| Utf1 | F GGATGTCCCGGTGACTACGTCTG | SEQ ID NO.: 81 |
| | R GGCGGATCTGGTTATCGAAGGGT | SEQ ID NO.: 82 |
| TDGF1 | F ATGGACGCAACTGTGAACATGATGTTCGCA | SEQ ID NO.: 83 |
| | R CTTTGAGGTCCTGGTCCATCACGTGACCAT | SEQ ID NO.: 84 |
| Esrrb | F GTGGCTGAGGGCATCAATG | SEQ ID NO.: 85 |
| | R AACCGAATGTCGTCCGAAGAC | SEQ ID NO.: 86 |
| Sal14 | F TGGCAGACGAGAAGTTCTTTC | SEQ ID NO.: 87 |
| | R TCCAACATTTATCCGAGCACAG | SEQ ID NO.: 88 |
| LIN28a | F GGCATCTGTAAGTGGTTCAACG | SEQ ID NO.: 89 |
| | R GCCAGTGACACGGATGGATT | SEQ ID NO.: 90 |
| B-actin | F CTGGCTGGCCGGGACCTGAC | SEQ ID NO.: 91 |
| | R ACCGCTCGTTGCCAATAGTGATGA | SEQ ID NO.: 92 | approximately 93% OCT4-GFP expression efficiency. Also,

TABLE 6

RT-PCR primers used to check expression of mouse differentiation markers

| Gene names | Primer sequences (5' → 3') | |
|---|---|---|
| Tuj1 | F ATCCACCTTCATTGGCAACAGCAC | SEQ ID NO.: 93 |
| | R ACTCGGACACCAGGTCATTCATGT | SEQ ID NO.: 94 |
| Map2 | F AGCCGCAACGCCAATGGATT | SEQ ID NO.: 95 |
| | R TTTGTTCCGAGGCTGGCGAT | SEQ ID NO.: 96 |
| GATA4 | F AACCAGAAAACGGAAGCCCAAG | SEQ ID NO.: 97 |
| | R TACGCGGTGATTATGTCCCCAT | SEQ ID NO.: 98 |
| SOX7 | F AACACGCTGCCTGAGAAAAACG | SEQ ID NO.: 99 |
| | R AATAGGCTGGAGATGGGGGACA | SEQ ID NO.: 100 |
| Foxa2 | F TACACACACGCCAAACCTCCCT | SEQ ID NO.: 101 |
| | R GCTTCCTTCAGTGCCAGTTGCT | SEQ ID NO.: 102 |
| CER1 | F AGGCAGAAGACAAGCCGGATCT | SEQ ID NO.: 103 |
| | R TCTTCATGGGCAATGGTCTGGT | SEQ ID NO.: 104 |
| Brachyury | F CCCGGTGCTGAAGGTAAATGTG | SEQ ID NO.: 105 |
| | R ATGAACTGGGTCTCGGGAAAGC | SEQ ID NO.: 106 |
| FLT-1 | F TACGAAAAGTCCGTGTCCTCGC | SEQ ID NO.: 107 |
| | R TTTCAGGTCCTCTCCTTCGGCT | SEQ ID NO.: 108 |
| CAD11 | F AAGACCCAGATGCTGCCAACAG | SEQ ID NO.: 109 |
| | R GCATGATTTCAGGGGGTAGGCT | SEQ ID NO.: 110 |
| KDR | F TTTCCTGGGACTGTGGCGAA | SEQ ID NO.: 111 |
| | R TGGACTCAATGGGCCTTCCA | SEQ ID NO.: 112 |
| Nef1 | F CGGAAGACGCCACTAACGAGAA | SEQ ID NO.: 113 |
| | R CTTCGGCGTTCTGCATGTTCTT | SEQ ID NO.: 114 |
| Nestin | F GGCATCCCTGAATTACCCAA | SEQ ID NO.: 115 |
| | R AGCTCATGGGCATCTGTCAA | SEQ ID NO.: 116 |
| GATA6 | F ACCTTATGGCGTAGAAATGCTGAGGGTG | SEQ ID NO.: 117 |
| | R CTGAATACTTGAGGTCACTGTTCTCGGG | SEQ ID NO.: 118 |

Figure 55:
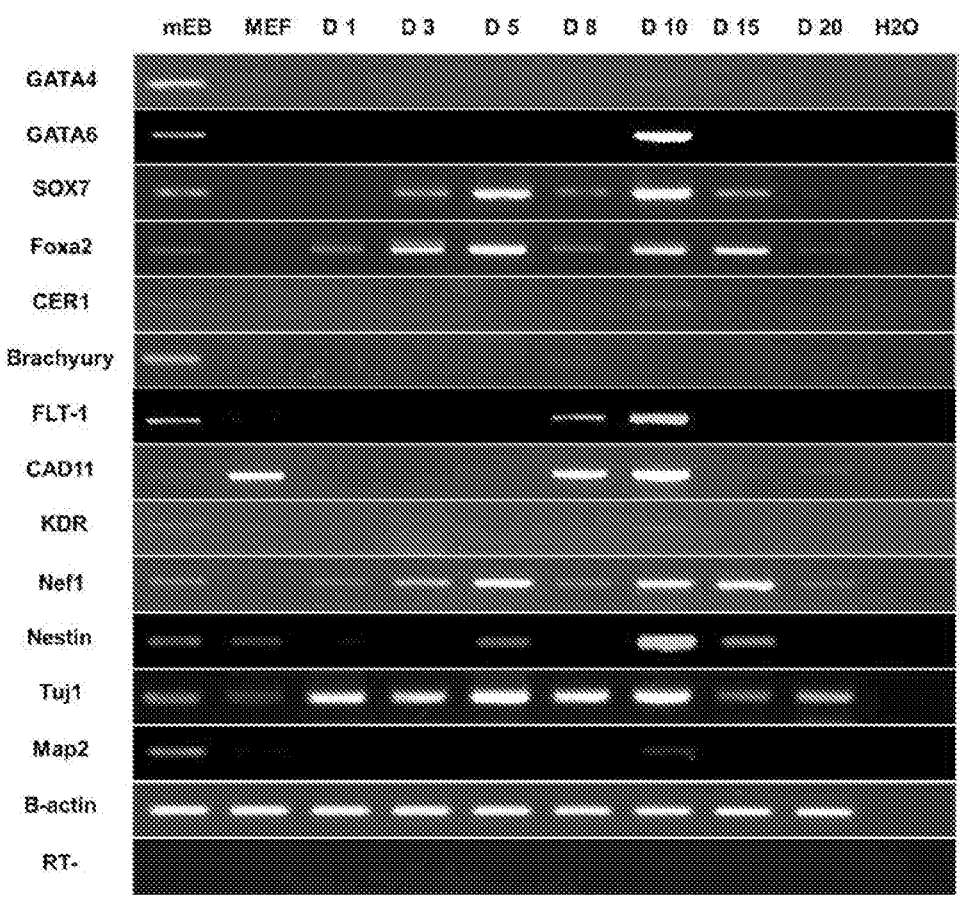
FIG. 55 shows RT-PCR analysis results of expression of the three germ layer marker in the mouse Physics cells.
Figure 56:
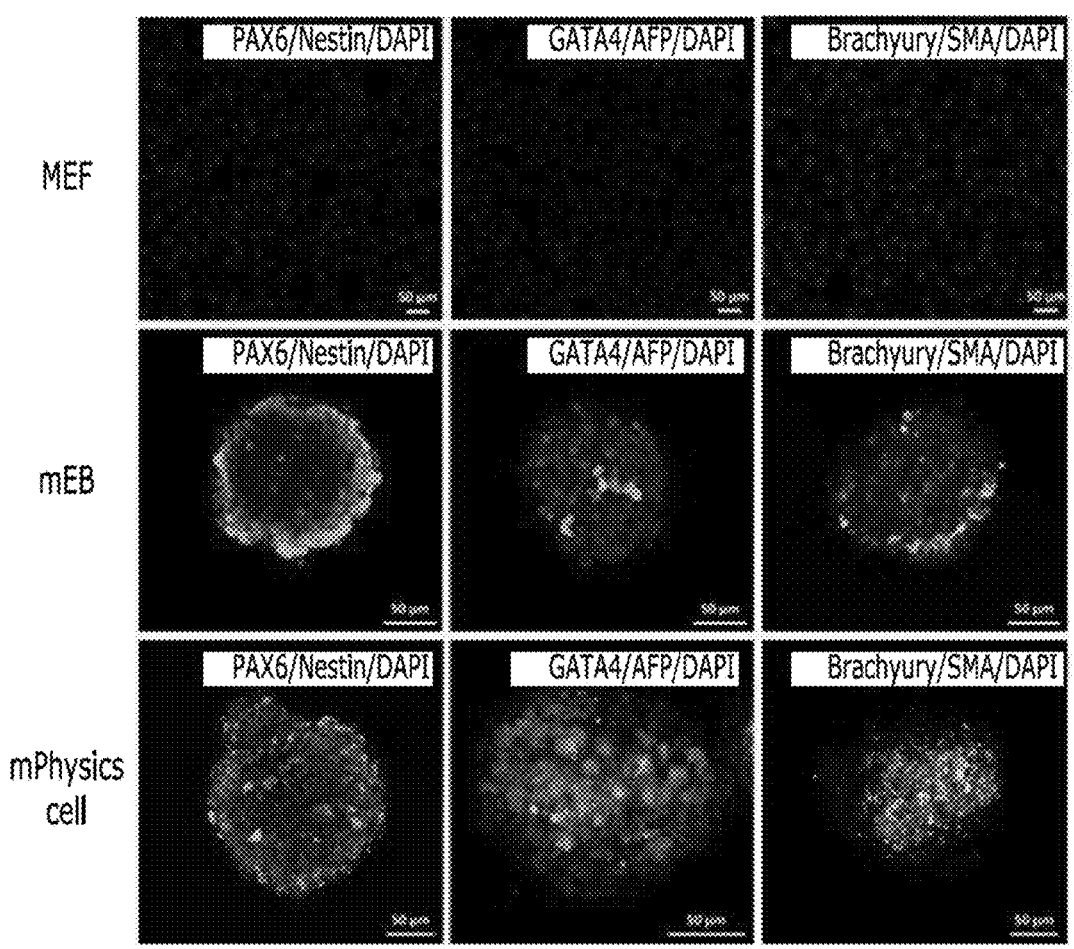
FIG. 56 shows results of analyzing expression of the three germ layer marker in the mouse Physics cells using an immunocytochemistry.

The expression of the three germ layer markers was checked. As a result, it was revealed that the markers of the endoderm (GATA6), the ectoderm (Nestin) and the mesoderm (Brachyury) were expressed at a high level. The other genes of the three germ layers started to be expressed on day 3 after formation of the Physics cells. The expression level of the three germ layer markers gradually increased for 20 days of culture (FIG. 55). Also, as shown in FIG. 56, the expression of the three germ layer protein markers was confirmed through immunostaining.

Figure 57:
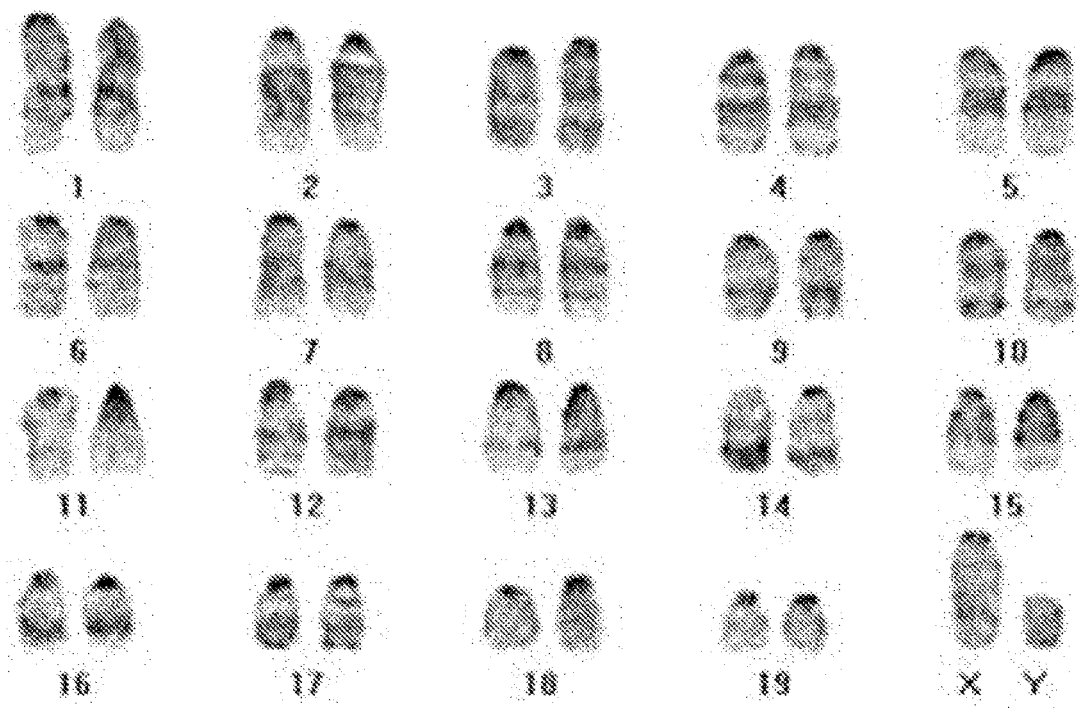
FIG. 57 shows results of karyotyping analysis of the mouse Physics cells.

Even in the mouse cells, the mPhysics cells formed by the ultrasound had a normal karyotype (FIG. 57).

The present invention has an effect of inducing a novel type of pluripotent cells, which has pluripotent characteristics and shows a stronger differentiation property than known induced pluripotent stem cells, from differentiated cells by applying suitable energy such as ultrasound, lasers, heat treatment, etc. without introduction of a reprogramming inducing factor into differentiated cells.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method of reprogramming differentiated cells into pluripotent cells, comprising:

treating a culture medium by applying energy to the culture medium to enhance spheroid-forming efficiency of differentiated cells prior to mixing the differentiated cells with the culture medium, wherein the energy applied to the culture medium is ultrasonic energy having an output intensity of 3 W/cm$^2$ to 7 W/cm$^2$ for 7 to 13 minutes;

mixing the differentiated cells with the treated culture medium;

applying ultrasonic energy to the mixture of the treated culture medium and the differentiated cells, and culturing the mixture for a predetermined time to form spheroids, wherein said spheroids have cells with pluripotent characteristics; wherein the differentiated cells are mammal-derived fibroblast cells;

wherein the culture medium is selected from the group consisting of an embryonic stem cell culture medium, and a stem cell differentiation-inducing medium;

wherein the applying ultrasonic energy to the mixture of the treated culture medium and the differentiated cells is performed at an output intensity of 0.5 W/cm$^2$ to 3 W/cm$^2$ for 1 to 5 seconds.

2. The method of claim 1, wherein the cells having pluripotent characteristics in the spheroids express one undifferentiated marker gene or a three germ layer marker gene selected from OCT3/4, SOX2, NANOG, c-MYC, KLF4, TDGF1, SSEA4, TRA-1-60, PAX6, Nestin, Brachyury, SMA, GATA4, and AFP.

3. The method of claim 1, wherein the culturing is carried out for 3 days to 10 days using a suspension culture method or a monolayer culture method.

* * * * *

SEQUENCE LISTING

<160> NUMBER OF SEQ ID NOS: 118

<210> SEQ ID NO 1
<211> LENGTH: 24
<212> TYPE: DNA
<213> ORGANISM: Artificial sequence
<220> FEATURE:
<223> OTHER INFORMATION: OCT3/4, forward primer

<400> SEQUENCE: 1
gacaggggga ggggaggagc tagg                                              24

<210> SEQ ID NO 2
<211> LENGTH: 26
<212> TYPE: DNA
<213> ORGANISM: Artificial sequence
<220> FEATURE:
<223> OTHER INFORMATION: OCT3/4, reverse primer

<400> SEQUENCE: 2
cttccctcca accagttgcc ccaaac                                            26

<210> SEQ ID NO 3
<211> LENGTH: 26
<212> TYPE: DNA
<213> ORGANISM: Artificial sequence
<220> FEATURE:
<223> OTHER INFORMATION: SOX-2, forward primer

<400> SEQUENCE: 3
gggaaatggg aggggtgcaa aagagg                                            26

<210> SEQ ID NO 4
<211> LENGTH: 26
<212> TYPE: DNA
<213> ORGANISM: Artificial sequence
<220> FEATURE:
<223> OTHER INFORMATION: SOX-2, reverse primer

<400> SEQUENCE: 4
ttgcgtgagt gtggatggga ttggtg                                            26

<210> SEQ ID NO 5
<211> LENGTH: 25
<212> TYPE: DNA
<213> ORGANISM: Artificial sequecne
<220> FEATURE:
<223> OTHER INFORMATION: NANOG, forward primer

<400> SEQUENCE: 5
cagccccgat tcttccacca gtccc                                             25

<210> SEQ ID NO 6
<211> LENGTH: 25
<212> TYPE: DNA
<213> ORGANISM: Artificial sequence
<220> FEATURE:
<223> OTHER INFORMATION: NANOG, reverse primer

<400> SEQUENCE: 6
cggaagattc ccagtcgggt tcacc                                             25

<210> SEQ ID NO 7
<211> LENGTH: 22
<212> TYPE: DNA
<213> ORGANISM: Artificial sequence

```
<220> FEATURE:
<223> OTHER INFORMATION: c-Myc, forward primer

<400> SEQUENCE: 7
aaacacaaac ttgaacagct ac                                           22

<210> SEQ ID NO 8
<211> LENGTH: 23
<212> TYPE: DNA
<213> ORGANISM: Artificial sequence
<220> FEATURE:
<223> OTHER INFORMATION: c-Myc, reverse primer

<400> SEQUENCE: 8
atttgaggca gtttacatta tgg                                          23

<210> SEQ ID NO 9
<211> LENGTH: 20
<212> TYPE: DNA
<213> ORGANISM: Artificial sequence
<220> FEATURE:
<223> OTHER INFORMATION: KLF4, forward primer

<400> SEQUENCE: 9
cccacatgaa gcgacttccc                                              20

<210> SEQ ID NO 10
<211> LENGTH: 21
<212> TYPE: DNA
<213> ORGANISM: Artificial sequence
<220> FEATURE:
<223> OTHER INFORMATION: KLF4, reverse primer

<400> SEQUENCE: 10
caggtccagg agatcgttga a                                            21

<210> SEQ ID NO 11
<211> LENGTH: 24
<212> TYPE: DNA
<213> ORGANISM: Artificial sequence
<220> FEATURE:
<223> OTHER INFORMATION: UTF1, forward primer

<400> SEQUENCE: 11
ccgtcgctga acaccgccct gctg                                         24

<210> SEQ ID NO 12
<211> LENGTH: 24
<212> TYPE: DNA
<213> ORGANISM: Artificial sequence
<220> FEATURE:
<223> OTHER INFORMATION: UTF1, reverse primer

<400> SEQUENCE: 12
cgcgctgccc agaatgaagc ccac                                         24

<210> SEQ ID NO 13
<211> LENGTH: 21
<212> TYPE: DNA
<213> ORGANISM: Artificial sequence
<220> FEATURE:
<223> OTHER INFORMATION: LIN28, forward primer

<400> SEQUENCE: 13
agcgcagatc aaaaggagac a                                            21
```

```
<210> SEQ ID NO 14
<211> LENGTH: 21
<212> TYPE: DNA
<213> ORGANISM: Artificial sequence
<220> FEATURE:
<223> OTHER INFORMATION: LIN28, reverse primer

<400> SEQUENCE: 14
cctctcgaaa gtaggttggc t                                             21

<210> SEQ ID NO 15
<211> LENGTH: 24
<212> TYPE: DNA
<213> ORGANISM: Artificial sequence
<220> FEATURE:
<223> OTHER INFORMATION: REX1, forward primer

<400> SEQUENCE: 15
cagatcctaa acagctcgca gaat                                          24

<210> SEQ ID NO 16
<211> LENGTH: 23
<212> TYPE: DNA
<213> ORGANISM: Artificial sequence
<220> FEATURE:
<223> OTHER INFORMATION: REX1, reverse primer

<400> SEQUENCE: 16
gcgtacgcaa attaaagtcc aga                                           23

<210> SEQ ID NO 17
<211> LENGTH: 23
<212> TYPE: DNA
<213> ORGANISM: Artificial sequence
<220> FEATURE:
<223> OTHER INFORMATION: FGF4, forward primer

<400> SEQUENCE: 17
ctacaacgcc tacgagtcct aca                                           23

<210> SEQ ID NO 18
<211> LENGTH: 24
<212> TYPE: DNA
<213> ORGANISM: Artificial sequence
<220> FEATURE:
<223> OTHER INFORMATION: FGF4, reverse primer

<400> SEQUENCE: 18
gttgcaccag aaaagtcaga gttg                                          24

<210> SEQ ID NO 19
<211> LENGTH: 20
<212> TYPE: DNA
<213> ORGANISM: Artificial sequence
<220> FEATURE:
<223> OTHER INFORMATION: FOXD3, forward primer

<400> SEQUENCE: 19
aagctggtcg agcaaactca                                               20

<210> SEQ ID NO 20
<211> LENGTH: 20
<212> TYPE: DNA
<213> ORGANISM: Artificial sequence
<220> FEATURE:
<223> OTHER INFORMATION: FOXD3, reverse primer
```

```
<400> SEQUENCE: 20
ctcccatccc cacggtacta                                              20

<210> SEQ ID NO 21
<211> LENGTH: 24
<212> TYPE: DNA
<213> ORGANISM: Artificial sequence
<220> FEATURE:
<223> OTHER INFORMATION: ESG1, forward primer

<400> SEQUENCE: 21
atatcccgcc gtgggtgaaa gttc                                         24

<210> SEQ ID NO 22
<211> LENGTH: 24
<212> TYPE: DNA
<213> ORGANISM: Artificial sequence
<220> FEATURE:
<223> OTHER INFORMATION: ESG1, reverse primer

<400> SEQUENCE: 22
actcagccat ggactggagc atcc                                         24

<210> SEQ ID NO 23
<211> LENGTH: 25
<212> TYPE: DNA
<213> ORGANISM: Artificial sequence
<220> FEATURE:
<223> OTHER INFORMATION: TDGF1, forward primer

<400> SEQUENCE: 23
ctgctgcctg aatgggggaa cctgc                                        25

<210> SEQ ID NO 24
<211> LENGTH: 27
<212> TYPE: DNA
<213> ORGANISM: Artificial sequence
<220> FEATURE:
<223> OTHER INFORMATION: TDGF1, reverse primer

<400> SEQUENCE: 24
gccacgaggt gctcatccat cacaagg                                      27

<210> SEQ ID NO 25
<211> LENGTH: 21
<212> TYPE: DNA
<213> ORGANISM: Artificial sequence
<220> FEATURE:
<223> OTHER INFORMATION: B-ACTN, forward primer

<400> SEQUENCE: 25
catgtacgtt gctatccagg c                                            21

<210> SEQ ID NO 26
<211> LENGTH: 21
<212> TYPE: DNA
<213> ORGANISM: Artificial sequence
<220> FEATURE:
<223> OTHER INFORMATION: B-ACTN, reverse primer

<400> SEQUENCE: 26
ctccttaatg tcacgcacga t                                            21

<210> SEQ ID NO 27
```

```
<211> LENGTH: 28
<212> TYPE: DNA
<213> ORGANISM: Artificial sequence
<220> FEATURE:
<223> OTHER INFORMATION: AFP, forward primer

<400> SEQUENCE: 27
gaatgctgca aactgaccac gctggaac                                      28

<210> SEQ ID NO 28
<211> LENGTH: 28
<212> TYPE: DNA
<213> ORGANISM: Artificial sequence
<220> FEATURE:
<223> OTHER INFORMATION: AFP, reverse primer

<400> SEQUENCE: 28
tggcattcaa gagggttttc agtctgga                                      28

<210> SEQ ID NO 29
<211> LENGTH: 26
<212> TYPE: DNA
<213> ORGANISM: Artificial sequence
<220> FEATURE:
<223> OTHER INFORMATION: FOXA2, forward primer

<400> SEQUENCE: 29
tgggagcggt gaagatggaa gggcac                                        26

<210> SEQ ID NO 30
<211> LENGTH: 26
<212> TYPE: DNA
<213> ORGANISM: Artificial sequence
<220> FEATURE:
<223> OTHER INFORMATION: FOXA2, reverse primer

<400> SEQUENCE: 30
tcatgccagc gcccacgtac gacgac                                        26

<210> SEQ ID NO 31
<211> LENGTH: 26
<212> TYPE: DNA
<213> ORGANISM: Artificial sequence
<220> FEATURE:
<223> OTHER INFORMATION: Brachyury, forward primer

<400> SEQUENCE: 31
gccctctccc tccctccac gcacag                                         26

<210> SEQ ID NO 32
<211> LENGTH: 26
<212> TYPE: DNA
<213> ORGANISM: Artificial sequence
<220> FEATURE:
<223> OTHER INFORMATION: Brachyury, reverse primer

<400> SEQUENCE: 32
cggcgccgtt gctcacagac cacagg                                        26

<210> SEQ ID NO 33
<211> LENGTH: 24
<212> TYPE: DNA
<213> ORGANISM: Artificial sequence
<220> FEATURE:
<223> OTHER INFORMATION: MSX1, forward primer

<400> SEQUENCE: 33
```

```
cgagaggacc ccgtggatgc agag                                           24
```

<210> SEQ ID NO 34
<211> LENGTH: 24
<212> TYPE: DNA
<213> ORGANISM: Artificial sequence
<220> FEATURE:
<223> OTHER INFORMATION: MSX1, reverse primer
<400> SEQUENCE: 34

```
ggcggccatc ttcagcttct ccag                                           24
```

<210> SEQ ID NO 35
<211> LENGTH: 21
<212> TYPE: DNA
<213> ORGANISM: Artificial sequence
<220> FEATURE:
<223> OTHER INFORMATION: ACTA2(a-SMA), forward primer
<400> SEQUENCE: 35

```
ctatgagggc tatgccttgc c                                              21
```

<210> SEQ ID NO 36
<211> LENGTH: 22
<212> TYPE: DNA
<213> ORGANISM: Artificial sequence
<220> FEATURE:
<223> OTHER INFORMATION: ACTA2(a-SMA), reverse primer
<400> SEQUENCE: 36

```
gctcagcagt agtaacgaag ga                                             22
```

<210> SEQ ID NO 37
<211> LENGTH: 26
<212> TYPE: DNA
<213> ORGANISM: Artificial sequence
<220> FEATURE:
<223> OTHER INFORMATION: TnTc, forward primer
<400> SEQUENCE: 37

```
atgagcggga gaaggagcgg cagaac                                         26
```

<210> SEQ ID NO 38
<211> LENGTH: 26
<212> TYPE: DNA
<213> ORGANISM: Artificial sequence
<220> FEATURE:
<223> OTHER INFORMATION: TnTc, reverse primer
<400> SEQUENCE: 38

```
tcaatggcca gcaccttcct cctctc                                         26
```

<210> SEQ ID NO 39
<211> LENGTH: 21
<212> TYPE: DNA
<213> ORGANISM: Artificial sequence
<220> FEATURE:
<223> OTHER INFORMATION: GATA4, forward primer
<400> SEQUENCE: 39

```
cgacacccca atctcgatat g                                              21
```

<210> SEQ ID NO 40
<211> LENGTH: 21
<212> TYPE: DNA

```
<213> ORGANISM: Artificial sequence
<220> FEATURE:
<223> OTHER INFORMATION: GATA4, reverse primer

<400> SEQUENCE: 40
gttgcacaga tagtgacccg t                                        21

<210> SEQ ID NO 41
<211> LENGTH: 20
<212> TYPE: DNA
<213> ORGANISM: Artificial sequence
<220> FEATURE:
<223> OTHER INFORMATION: NKX2.5, forward primer

<400> SEQUENCE: 41
ccaaggaccc tagagccgaa                                          20

<210> SEQ ID NO 42
<211> LENGTH: 20
<212> TYPE: DNA
<213> ORGANISM: Artificial sequence
<220> FEATURE:
<223> OTHER INFORMATION: NKX2.5, reverse primer

<400> SEQUENCE: 42
ataggcgggg taggcgttat                                          20

<210> SEQ ID NO 43
<211> LENGTH: 21
<212> TYPE: DNA
<213> ORGANISM: Artificial sequence
<220> FEATURE:
<223> OTHER INFORMATION: Nestin, forward primer

<400> SEQUENCE: 43
gaaacagcca tagagggcaa a                                        21

<210> SEQ ID NO 44
<211> LENGTH: 23
<212> TYPE: DNA
<213> ORGANISM: Artificial sequence
<220> FEATURE:
<223> OTHER INFORMATION: Nestin, reverse primer

<400> SEQUENCE: 44
tggttttcca gagtcttcag tga                                      23

<210> SEQ ID NO 45
<211> LENGTH: 28
<212> TYPE: DNA
<213> ORGANISM: Artificial sequence
<220> FEATURE:
<223> OTHER INFORMATION: PAX6, forward primer

<400> SEQUENCE: 45
acccattatc cagatgtgtt tgcccgag                                 28

<210> SEQ ID NO 46
<211> LENGTH: 26
<212> TYPE: DNA
<213> ORGANISM: Artificial sequence
<220> FEATURE:
<223> OTHER INFORMATION: PAX6, reverse primer

<400> SEQUENCE: 46
atggtgaagc tgggcatagg cggcag                                   26
```

<210> SEQ ID NO 47
<211> LENGTH: 30
<212> TYPE: DNA
<213> ORGANISM: Artificial sequence
<220> FEATURE:
<223> OTHER INFORMATION: Map2, forward primer

<400> SEQUENCE: 47
caggtggcgg acgtgtgaaa attgagagtg                              30

<210> SEQ ID NO 48
<211> LENGTH: 26
<212> TYPE: DNA
<213> ORGANISM: Artificial sequence
<220> FEATURE:
<223> OTHER INFORMATION: Map2, reverse primer

<400> SEQUENCE: 48
cacgctggat ctgcctgggg actgtg                                  26

<210> SEQ ID NO 49
<211> LENGTH: 26
<212> TYPE: DNA
<213> ORGANISM: Artificial sequence
<220> FEATURE:
<223> OTHER INFORMATION: GFAP, forward primer

<400> SEQUENCE: 49
ggcccgccac ttgcaggagt accagg                                  26

<210> SEQ ID NO 50
<211> LENGTH: 26
<212> TYPE: DNA
<213> ORGANISM: Artificial sequence
<220> FEATURE:
<223> OTHER INFORMATION: GFAP, reverse primer

<400> SEQUENCE: 50
cttctgctcg ggcccctcat gagacg                                  26

<210> SEQ ID NO 51
<211> LENGTH: 20
<212> TYPE: DNA
<213> ORGANISM: Artificial sequence
<220> FEATURE:
<223> OTHER INFORMATION: Sox1, forward primer

<400> SEQUENCE: 51
tacagcccca tctccaactc                                         20

<210> SEQ ID NO 52
<211> LENGTH: 20
<212> TYPE: DNA
<213> ORGANISM: Artificial sequence
<220> FEATURE:
<223> OTHER INFORMATION: Sox1, reverse primer

<400> SEQUENCE: 52
gctccgactt caccagagag                                         20

<210> SEQ ID NO 53
<211> LENGTH: 24
<212> TYPE: DNA
<213> ORGANISM: Artificial sequence
<220> FEATURE:

```
<223> OTHER INFORMATION: Chat, forward primer

<400> SEQUENCE: 53
ggaggcgtgg atctcagcga cacc                                              24

<210> SEQ ID NO 54
<211> LENGTH: 24
<212> TYPE: DNA
<213> ORGANISM: Artificial sequence
<220> FEATURE:
<223> OTHER INFORMATION: Chat, reverse primer

<400> SEQUENCE: 54
cggggagctc gctgacggag tctg                                              24

<210> SEQ ID NO 55
<211> LENGTH: 25
<212> TYPE: DNA
<213> ORGANISM: Artificial sequence
<220> FEATURE:
<223> OTHER INFORMATION: Aadc, forward primer

<400> SEQUENCE: 55
cgccaggatc cccgcttgaa atctg                                             25

<210> SEQ ID NO 56
<211> LENGTH: 26
<212> TYPE: DNA
<213> ORGANISM: Artificial sequence
<220> FEATURE:
<223> OTHER INFORMATION: Aadc, reverse primer

<400> SEQUENCE: 56
tcggccgcca gctctttgat gtgttc                                            26

<210> SEQ ID NO 57
<211> LENGTH: 26
<212> TYPE: DNA
<213> ORGANISM: Artificial sequence
<220> FEATURE:
<223> OTHER INFORMATION: Dat, forward primer

<400> SEQUENCE: 57
acagagggga ggtgcgccag ttcacg                                            26

<210> SEQ ID NO 58
<211> LENGTH: 26
<212> TYPE: DNA
<213> ORGANISM: Artificial sequence
<220> FEATURE:
<223> OTHER INFORMATION: Dat, reverse primer

<400> SEQUENCE: 58
acggggtgga cctcgctgca cagatc                                            26

<210> SEQ ID NO 59
<211> LENGTH: 20
<212> TYPE: DNA
<213> ORGANISM: Artificial sequence
<220> FEATURE:
<223> OTHER INFORMATION: Th, forward primer

<400> SEQUENCE: 59 ctgtggccttt tgaggagaag                                                  20
```

```
<210> SEQ ID NO 60
<211> LENGTH: 20
<212> TYPE: DNA
<213> ORGANISM: Artificial sequence
<220> FEATURE:
<223> OTHER INFORMATION: Th, reverse primer

<400> SEQUENCE: 60
ggtggatttt ggcttcaaac                                        20

<210> SEQ ID NO 61
<211> LENGTH: 23
<212> TYPE: DNA
<213> ORGANISM: Artificial sequence
<220> FEATURE:
<223> OTHER INFORMATION: Tuj1, forward primer

<400> SEQUENCE: 61
gagcggatca gcgtctacta caa                                    23

<210> SEQ ID NO 62
<211> LENGTH: 22
<212> TYPE: DNA
<213> ORGANISM: Artificial sequence
<220> FEATURE:
<223> OTHER INFORMATION: Tuj1, reverse primer

<400> SEQUENCE: 62
gatactcctc acgcaccttg ct                                     22

<210> SEQ ID NO 63
<211> LENGTH: 20
<212> TYPE: DNA
<213> ORGANISM: Artificial sequence
<220> FEATURE:
<223> OTHER INFORMATION: Vglut1, forward primer

<400> SEQUENCE: 63
cgacgacagc cttttgtggt                                        20

<210> SEQ ID NO 64
<211> LENGTH: 21
<212> TYPE: DNA
<213> ORGANISM: Artificial sequence
<220> FEATURE:
<223> OTHER INFORMATION: Vglut1, reverse primer

<400> SEQUENCE: 64
gccgagacgt agaaaacaga g                                      21

<210> SEQ ID NO 65
<211> LENGTH: 18
<212> TYPE: DNA
<213> ORGANISM: Artificial sequence
<220> FEATURE:
<223> OTHER INFORMATION: Vmat2, forward primer

<400> SEQUENCE: 65
ctttggagtt ggttttgc                                          18

<210> SEQ ID NO 66
<211> LENGTH: 17
<212> TYPE: DNA
<213> ORGANISM: Artificial sequence
<220> FEATURE:
<223> OTHER INFORMATION: Vmat2, reverse primer
```

```
<400> SEQUENCE: 66
gagttgtggt ccatgag                                                  17

<210> SEQ ID NO 67
<211> LENGTH: 24
<212> TYPE: DNA
<213> ORGANISM: Artificial sequence
<220> FEATURE:
<223> OTHER INFORMATION: OCT3/4, forward primer

<400> SEQUENCE: 67
ctgagggcca ggcaggagca cgag                                          24

<210> SEQ ID NO 68
<211> LENGTH: 24
<212> TYPE: DNA
<213> ORGANISM: Artificial sequence
<220> FEATURE:
<223> OTHER INFORMATION: OCT3/4, reverse primer

<400> SEQUENCE: 68
ctgtagggag ggcttcgggc actt                                          24

<210> SEQ ID NO 69
<211> LENGTH: 23
<212> TYPE: DNA
<213> ORGANISM: Artificial sequence
<220> FEATURE:
<223> OTHER INFORMATION: Sox2, forward primer

<400> SEQUENCE: 69
tagagctaga ctccgggcga tga                                           23

<210> SEQ ID NO 70
<211> LENGTH: 23
<212> TYPE: DNA
<213> ORGANISM: Artificial sequence
<220> FEATURE:
<223> OTHER INFORMATION: Sox2, reverse primer

<400> SEQUENCE: 70
ttgccttaaa caagaccacg aaa                                           23

<210> SEQ ID NO 71
<211> LENGTH: 20
<212> TYPE: DNA
<213> ORGANISM: Artificial sequence
<220> FEATURE:
<223> OTHER INFORMATION: Nanog, forward primer

<400> SEQUENCE: 71
caggtgtttg agggtagctc                                               20

<210> SEQ ID NO 72
<211> LENGTH: 20
<212> TYPE: DNA
<213> ORGANISM: Artificial sequence
<220> FEATURE:
<223> OTHER INFORMATION: Nanog, reverse primer

<400> SEQUENCE: 72
cggttcatca tggtacagtc                                               20

<210> SEQ ID NO 73
<211> LENGTH: 28
```

<212> TYPE: DNA
<213> ORGANISM: Artificial sequence
<220> FEATURE:
<223> OTHER INFORMATION: c-Myc, forward primer

<400> SEQUENCE: 73
tgacctaact cgaggaggag ctggaatc                                          28

<210> SEQ ID NO 74
<211> LENGTH: 32
<212> TYPE: DNA
<213> ORGANISM: Artificial sequence
<220> FEATURE:
<223> OTHER INFORMATION: c-Myc, reverse primer

<400> SEQUENCE: 74
aagtttgagg cagttaaaat tatggctgaa gc                                     32

<210> SEQ ID NO 75
<211> LENGTH: 24
<212> TYPE: DNA
<213> ORGANISM: Artificial sequence
<220> FEATURE:
<223> OTHER INFORMATION: Klf4, forward primer

<400> SEQUENCE: 75
gcgaactcac acaggcgaga aacc                                              24

<210> SEQ ID NO 76
<211> LENGTH: 23
<212> TYPE: DNA
<213> ORGANISM: Artificial sequence
<220> FEATURE:
<223> OTHER INFORMATION: Klf4, reverse primer

<400> SEQUENCE: 76
tcgcttcctc ttcctccgac aca                                               23

<210> SEQ ID NO 77
<211> LENGTH: 24
<212> TYPE: DNA
<213> ORGANISM: Artificial sequence
<220> FEATURE:
<223> OTHER INFORMATION: Esg1, forward primer

<400> SEQUENCE: 77
gaagtctggt tccttggcag gatg                                              24

<210> SEQ ID NO 78
<211> LENGTH: 20
<212> TYPE: DNA
<213> ORGANISM: Artificial sequence
<220> FEATURE:
<223> OTHER INFORMATION: Esg1, reverse primer

<400> SEQUENCE: 78
actcgataca ctggcctagc                                                   20

<210> SEQ ID NO 79
<211> LENGTH: 24
<212> TYPE: DNA
<213> ORGANISM: Artificial sequence
<220> FEATURE:
<223> OTHER INFORMATION: Rex1, forward primer

<400> SEQUENCE: 79
acgagtggca gtttcttctt ggga                                              24

<210> SEQ ID NO 80
<211> LENGTH: 24
<212> TYPE: DNA
<213> ORGANISM: Artificial sequence
<220> FEATURE:
<223> OTHER INFORMATION: Rex1, reverse primer

<400> SEQUENCE: 80
tatgactcac ttccaggggg cact                                              24

<210> SEQ ID NO 81
<211> LENGTH: 23
<212> TYPE: DNA
<213> ORGANISM: Artificial sequence
<220> FEATURE:
<223> OTHER INFORMATION: Utf1, forward primer

<400> SEQUENCE: 81
ggatgtcccg gtgactacgt ctg                                               23

<210> SEQ ID NO 82
<211> LENGTH: 23
<212> TYPE: DNA
<213> ORGANISM: Artificial sequence
<220> FEATURE:
<223> OTHER INFORMATION: Utf1, reverse primer

<400> SEQUENCE: 82
ggcggatctg gttatcgaag ggt                                               23

<210> SEQ ID NO 83
<211> LENGTH: 30
<212> TYPE: DNA
<213> ORGANISM: Artificial sequence
<220> FEATURE:
<223> OTHER INFORMATION: TDGF1, forward primer

<400> SEQUENCE: 83
atggacgcaa ctgtgaacat gatgttcgca                                        30

<210> SEQ ID NO 84
<211> LENGTH: 30
<212> TYPE: DNA
<213> ORGANISM: Artificial sequence
<220> FEATURE:
<223> OTHER INFORMATION: TDGF1, reverse primer

<400> SEQUENCE: 84
ctttgaggtc ctggtccatc acgtgaccat                                        30

<210> SEQ ID NO 85
<211> LENGTH: 19
<212> TYPE: DNA
<213> ORGANISM: Artificial sequence
<220> FEATURE:
<223> OTHER INFORMATION: Esrrb, forward primer

<400> SEQUENCE: 85
gtggctgagg gcatcaatg                                                    19

<210> SEQ ID NO 86
<211> LENGTH: 21
<212> TYPE: DNA
<213> ORGANISM: Artificial sequence

```
<220> FEATURE:
<223> OTHER INFORMATION: Esrrb, reverse primer

<400> SEQUENCE: 86
aaccgaatgt cgtccgaaga c                                          21

<210> SEQ ID NO 87
<211> LENGTH: 21
<212> TYPE: DNA
<213> ORGANISM: Artificial sequence
<220> FEATURE:
<223> OTHER INFORMATION: Sall4, forward primer

<400> SEQUENCE: 87
tggcagacga gaagttcttt c                                          21

<210> SEQ ID NO 88
<211> LENGTH: 22
<212> TYPE: DNA
<213> ORGANISM: Artificial sequence
<220> FEATURE:
<223> OTHER INFORMATION: Sall4, reverse primer

<400> SEQUENCE: 88
tccaacattt atccgagcac ag                                         22

<210> SEQ ID NO 89
<211> LENGTH: 22
<212> TYPE: DNA
<213> ORGANISM: Artificial sequence
<220> FEATURE:
<223> OTHER INFORMATION: LIN28a, forward primer

<400> SEQUENCE: 89
ggcatctgta agtggttcaa cg                                         22

<210> SEQ ID NO 90
<211> LENGTH: 20
<212> TYPE: DNA
<213> ORGANISM: Artificial sequence
<220> FEATURE:
<223> OTHER INFORMATION: LIN28a, reverse primer

<400> SEQUENCE: 90
gccagtgaca cggatggatt                                            20

<210> SEQ ID NO 91
<211> LENGTH: 20
<212> TYPE: DNA
<213> ORGANISM: Artificial sequence
<220> FEATURE:
<223> OTHER INFORMATION: B-actin, forward primer

<400> SEQUENCE: 91
ctggctggcc gggacctgac                                            20

<210> SEQ ID NO 92
<211> LENGTH: 24
<212> TYPE: DNA
<213> ORGANISM: Artificial sequence
<220> FEATURE:
<223> OTHER INFORMATION: B-actin, reverse primer

<400> SEQUENCE: 92
accgctcgtt gccaatagtg atga                                       24
```

```
<210> SEQ ID NO 93
<211> LENGTH: 24
<212> TYPE: DNA
<213> ORGANISM: Artificial sequence
<220> FEATURE:
<223> OTHER INFORMATION: Tuj1, forward primer

<400> SEQUENCE: 93
atccaccttc attggcaaca gcac                                              24

<210> SEQ ID NO 94
<211> LENGTH: 24
<212> TYPE: DNA
<213> ORGANISM: Artificial sequence
<220> FEATURE:
<223> OTHER INFORMATION: Tuj1, reverse primer

<400> SEQUENCE: 94
actcggacac caggtcattc atgt                                              24

<210> SEQ ID NO 95
<211> LENGTH: 20
<212> TYPE: DNA
<213> ORGANISM: Artificial sequence
<220> FEATURE:
<223> OTHER INFORMATION: Map2, forward primer

<400> SEQUENCE: 95
agccgcaacg ccaatggatt                                                   20

<210> SEQ ID NO 96
<211> LENGTH: 20
<212> TYPE: DNA
<213> ORGANISM: Artificial sequence
<220> FEATURE:
<223> OTHER INFORMATION: Map2, reverse primer

<400> SEQUENCE: 96
tttgttccga ggctggcgat                                                   20

<210> SEQ ID NO 97
<211> LENGTH: 22
<212> TYPE: DNA
<213> ORGANISM: Artificial sequence
<220> FEATURE:
<223> OTHER INFORMATION: GATA4, forward primer

<400> SEQUENCE: 97
aaccagaaaa cggaagccca ag                                                22

<210> SEQ ID NO 98
<211> LENGTH: 22
<212> TYPE: DNA
<213> ORGANISM: Artificial sequence
<220> FEATURE:
<223> OTHER INFORMATION: GATA4, reverse primer

<400> SEQUENCE: 98
tacgcggtga ttatgtcccc at                                                22

<210> SEQ ID NO 99
<211> LENGTH: 22
<212> TYPE: DNA
<213> ORGANISM: Artificial sequence
<220> FEATURE:
<223> OTHER INFORMATION: SOX7, forward primer
```

<400> SEQUENCE: 99
aacacgctgc ctgagaaaaa cg                                           22

<210> SEQ ID NO 100
<211> LENGTH: 22
<212> TYPE: DNA
<213> ORGANISM: Artificial sequence
<220> FEATURE:
<223> OTHER INFORMATION: SOX7, reverse primer

<400> SEQUENCE: 100
aataggctgg agatggggga ca                                           22

<210> SEQ ID NO 101
<211> LENGTH: 22
<212> TYPE: DNA
<213> ORGANISM: Artificial sequence
<220> FEATURE:
<223> OTHER INFORMATION: Foxa2, forward primer

<400> SEQUENCE: 101
tacacacacg ccaaacctcc ct                                           22

<210> SEQ ID NO 102
<211> LENGTH: 22
<212> TYPE: DNA
<213> ORGANISM: Artificial sequence
<220> FEATURE:
<223> OTHER INFORMATION: Foxa2, reverse primer

<400> SEQUENCE: 102
gcttccttca gtgccagttg ct                                           22

<210> SEQ ID NO 103
<211> LENGTH: 22
<212> TYPE: DNA
<213> ORGANISM: Artificial sequence
<220> FEATURE:
<223> OTHER INFORMATION: CER1, forward primer

<400> SEQUENCE: 103
aggcagaaga caagccggat ct                                           22

<210> SEQ ID NO 104
<211> LENGTH: 22
<212> TYPE: DNA
<213> ORGANISM: Artificial sequence
<220> FEATURE:
<223> OTHER INFORMATION: CER1, reverse primer

<400> SEQUENCE: 104
tcttcatggg caatggtctg gt                                           22

<210> SEQ ID NO 105
<211> LENGTH: 22
<212> TYPE: DNA
<213> ORGANISM: Artificial sequence
<220> FEATURE:
<223> OTHER INFORMATION: Brachyury, forward primer

<400> SEQUENCE: 105
cccggtgctg aaggtaaatg tg                                           22

<210> SEQ ID NO 106

```
<211> LENGTH: 22
<212> TYPE: DNA
<213> ORGANISM: Artificial sequence
<220> FEATURE:
<223> OTHER INFORMATION: Brachyury, reverse primer

<400> SEQUENCE: 106
atgaactggg tctcgggaaa gc                                              22

<210> SEQ ID NO 107
<211> LENGTH: 22
<212> TYPE: DNA
<213> ORGANISM: Artificial sequence
<220> FEATURE:
<223> OTHER INFORMATION: FLT-1, forward primer

<400> SEQUENCE: 107
tacgaaaagt ccgtgtcctc gc                                              22

<210> SEQ ID NO 108
<211> LENGTH: 22
<212> TYPE: DNA
<213> ORGANISM: Artificial sequence
<220> FEATURE:
<223> OTHER INFORMATION: FLT-1, reverse primer

<400> SEQUENCE: 108
tttcaggtcc tctccttcgg ct                                              22

<210> SEQ ID NO 109
<211> LENGTH: 22
<212> TYPE: DNA
<213> ORGANISM: Artificial sequence
<220> FEATURE:
<223> OTHER INFORMATION: CAD11, forward primer

<400> SEQUENCE: 109
aagacccaga tgctgccaac ag                                              22

<210> SEQ ID NO 110
<211> LENGTH: 22
<212> TYPE: DNA
<213> ORGANISM: Artificial sequence
<220> FEATURE:
<223> OTHER INFORMATION: CAD11, reverse primer

<400> SEQUENCE: 110
gcatgatttc aggggggtagg ct                                             22

<210> SEQ ID NO 111
<211> LENGTH: 20
<212> TYPE: DNA
<213> ORGANISM: Artificial sequence
<220> FEATURE:
<223> OTHER INFORMATION: KDR, forward primer

<400> SEQUENCE: 111
tttcctggga ctgtggcgaa                                                 20

<210> SEQ ID NO 112
<211> LENGTH: 20
<212> TYPE: DNA
<213> ORGANISM: Artificial sequence
<220> FEATURE:
<223> OTHER INFORMATION: KDR, reverse primer

<400> SEQUENCE: 112
```

```
tggactcaat gggccttcca                                               20

<210> SEQ ID NO 113
<211> LENGTH: 22
<212> TYPE: DNA
<213> ORGANISM: Artificial sequence
<220> FEATURE:
<223> OTHER INFORMATION: Nef1, forward primer

<400> SEQUENCE: 113
cggaagacgc cactaacgag aa                                            22

<210> SEQ ID NO 114
<211> LENGTH: 22
<212> TYPE: DNA
<213> ORGANISM: Artificial sequence
<220> FEATURE:
<223> OTHER INFORMATION: Nef1, reverse primer

<400> SEQUENCE: 114
cttcggcgtt ctgcatgttc tt                                            22

<210> SEQ ID NO 115
<211> LENGTH: 20
<212> TYPE: DNA
<213> ORGANISM: Artificial sequence
<220> FEATURE:
<223> OTHER INFORMATION: Nestin, forward primer

<400> SEQUENCE: 115
ggcatccctg aattacccaa                                               20

<210> SEQ ID NO 116
<211> LENGTH: 20
<212> TYPE: DNA
<213> ORGANISM: Artificial sequence
<220> FEATURE:
<223> OTHER INFORMATION: Nestin, reverse primer

<400> SEQUENCE: 116
agctcatggg catctgtcaa                                               20

<210> SEQ ID NO 117
<211> LENGTH: 28
<212> TYPE: DNA
<213> ORGANISM: Artificial sequence
<220> FEATURE:
<223> OTHER INFORMATION: GATA6, forward primer

<400> SEQUENCE: 117
accttatggc gtagaaatgc tgagggtg                                      28

<210> SEQ ID NO 118
<211> LENGTH: 28
<212> TYPE: DNA
<213> ORGANISM: Artificial sequence
<220> FEATURE:
<223> OTHER INFORMATION: GATA6, reverse primer

<400> SEQUENCE: 118
ctgaatactt gaggtcactg ttctcggg                                      28
```